United States Patent
Spruit et al.

(10) Patent No.: US 9,814,552 B2
(45) Date of Patent: Nov. 14, 2017

(54) GUM DETECTION USING AN OPTICAL DETECTOR IN A DENTAL HYGIENE DETECTION APPARATUS

(71) Applicant: KONINKLIJKE PHILIPS N.V., Eindhoven (NL)

(72) Inventors: Johannes Hendrikus Maria Spruit, Waalre (NL); Petrus Theodorus Jutte, Weert (NL); Olaf Thomas Johan Antonie Vermeulen, Oss (NL); Adrianus Wilhelmus Dionisius Maria Van Den Bijgaart, Helvoirt (NL); Martin John Edwards, Solihull (GB); Steven Charles Deane, Cambridge (GB); Edgar Martinus Van Gool, Veghel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/648,269

(22) PCT Filed: Dec. 20, 2013

(86) PCT No.: PCT/IB2013/061187
§ 371 (c)(1),
(2) Date: May 29, 2015

(87) PCT Pub. No.: WO2014/097240
PCT Pub. Date: Jun. 26, 2014

(65) Prior Publication Data
US 2015/0305670 A1    Oct. 29, 2015

Related U.S. Application Data

(60) Provisional application No. 61/746,361, filed on Dec. 27, 2012, provisional application No. 61/740,904, filed on Dec. 21, 2012.

(51) Int. Cl.
*A61C 3/00* (2006.01)
*A61C 1/00* (2006.01)
(Continued)

(52) U.S. Cl.
CPC .......... *A61C 19/04* (2013.01); *A46B 15/0036* (2013.01); *A61B 5/0013* (2013.01);
(Continued)

(58) Field of Classification Search
USPC .............................................. 433/20, 27, 29
See application file for complete search history.

(56) References Cited

U.S. PATENT DOCUMENTS

| 4,479,499 A | 10/1984 | Alfano |
| 5,894,620 A | 4/1999 | Polaert et al. |

(Continued)

FOREIGN PATENT DOCUMENTS

WO    2014097238 A1    6/2014

*Primary Examiner* — Nicole F Johnson

(57) ABSTRACT

A detection apparatus enables detection of a substance that may be present on the surface based on measurement of a stream probe signal correlating a substance at least partially obstructing the passage of fluid through a stream probe includes a distal optical gum detector transmission portion and a distal optical gum detector reception portion in a position to transmit and to receive, respectively, an optical signal controlled by a controller, enables the controller to determine if an open port of a distal tip of the stream probe is in contact with a substance at least partially obstructing the passage of fluid through the open port and not in contact with the gums of a subject or of a user of the detection apparatus to override false positive signals.

28 Claims, 29 Drawing Sheets

(51) Int. Cl.
    *A61C 19/04*     (2006.01)
    *A61C 17/22*     (2006.01)
    *G01N 7/00*     (2006.01)
    *A61B 5/00*     (2006.01)
    *A46B 15/00*     (2006.01)

(52) U.S. Cl.
CPC .......... *A61B 5/0088* (2013.01); *A61B 5/4547* (2013.01); *A61B 5/4552* (2013.01); *A61B 5/6891* (2013.01); *A61B 5/742* (2013.01); *A61B 5/7405* (2013.01); *A61B 5/746* (2013.01); *A61C 17/22* (2013.01); *A61C 17/227* (2013.01); *G01N 7/00* (2013.01); *A61B 2562/0233* (2013.01); *A61B 2562/0247* (2013.01); *A61B 2562/0261* (2013.01); *A61B 2576/02* (2013.01)

(56) References Cited

U.S. PATENT DOCUMENTS

| | | |
|---|---|---|
| 6,862,771 B1 | 3/2005 | Muller |
| 7,413,567 B2 | 8/2008 | Weckwerth et al. |
| 2001/0012605 A1 | 8/2001 | Kawamura |
| 2004/0023184 A1 | 2/2004 | de Josselin de Jong et al. |
| 2006/0281042 A1* | 12/2006 | Rizoiu .................. A46B 5/002 433/29 |
| 2010/0253773 A1 | 10/2010 | Oota et al. |
| 2011/0314618 A1 | 12/2011 | Binner et al. |
| 2012/0251971 A1 | 10/2012 | Fish et al. |

\* cited by examiner

GUM DETECTION USING AN OPTICAL DETECTOR IN A DENTAL HYGIENE DETECTION APPARATUS

CROSS-REFERENCE TO PRIOR APPLICATIONS

This application is the U.S. National Phase application under 35 U.S.C. §371 of International Application No. PCT/IB2013/061187, filed on Dec. 20, 2013, which claims the benefit of U.S. Provisional Patent Application No. 61/746,361, filed on Dec. 27, 2012, and U.S. Provisional Application No. 61/740,904, filed on Dec. 21, 2012. These applications are hereby incorporated by reference herein.

CROSS-REFERENCE TO RELATED APPLICATIONS

This application claims the benefit of, and priority to, U.S. Provisional Patent Application No. 61/740,904 filed on Dec. 21, 2012 entitled "PLAQUE DETECTION USING A STREAM PROBE" and, U.S. Provisional Patent Application No. 61/746,361 filed on Dec. 27, 2012 entitled "PLAQUE DETECTION USING A STREAM PROBE", the entire contents of both applications hereby being incorporated herein by reference.

TECHNICAL FIELD

The present disclosure relates to apparatuses used for detecting the state of a dental surface. More particularly, the present disclosure relates to a stream probe that is utilized to detect the state of a dental surface.

BACKGROUND OF THE INVENTION

Caries or periodontal diseases are thought to be infectious diseases caused by bacteria present in dental plaques. Removal of dental plaques is highly important for the health of oral cavities. Dental plaques, however, are not easy to identify by the naked eye. A variety of plaque detection apparatuses have been produced to aid in the detection of dental plaque and/or caries.

Most of the dental plaque detection apparatuses are configured for use by trained professionals and make use of the fact that the visible luminescence spectra from dental plaque (and/or caries) and non-decayed regions of a tooth are substantially different. Some dental plaque detection apparatuses are configured for use by consumers (most of whom are, typically, not trained dental professionals) in their own homes in helping consumers achieve good oral hygiene.

For example, one known type of dental plaque apparatus utilizes irradiated light to illuminate tooth material and gums to identify areas infected by biofilms and areas of dental plaque. This type of plaque detection apparatus may utilize a monochromatic excitation light and may be configured to detect fluorescent light in 2 bands 440-470 nm (e.g., blue light) and 560-640 nm (e.g., red light); the intensities are subtracted to reveal the dental plaque and/or caries regions.

While the aforementioned dental plaque apparatus are suitable for their intended use, they exhibit one or more shortcomings. Specifically, it is known that each area of the eye absorbs different wavelengths of light and, if too much light is absorbed by the eye, the eye may be damaged. As can be appreciated, to avoid possible eye injury, it is imperative that a user not switch on the plaque detection apparatus until the plaque detection apparatus is appropriately placed inside the mouth. The aforementioned devices, however, are not configured to automatically detect when the plaque detection apparatus are placed inside the mouth. As a result thereof, potentially harmful radiation that could damage the eyes, or cause uncomfortable glare if exposed to the eyes, may result if proper handling precautions are not followed, e.g., consumer misuse. Furthermore, this technique is especially suitable to detect old plaque; a distinction between teeth fluorescence and young (1 day old) plaque fluorescence is not made.

SUMMARY OF THE INVENTION

It is an object of the invention to provide an improved detection of a substance (e.g. plaque) on a surface (e.g. a dental surface).

Accordingly, an aspect of the present disclosure includes an apparatus for detecting the presence of a substance on a surface. The apparatus includes a proximal body portion comprising a proximal pump (e.g., syringe) portion and a proximal probe portion and at least one distal probe portion configured to be immersed in a first fluid. The proximal pump portion and the distal probe portion are in fluid communication with one another. The distal probe portion defines a distal tip having an open port to enable the passage of a second fluid (e.g. a gas or a liquid) therethrough. The apparatus is configured such that passage of the second fluid through the distal tip enables detection of a substance that may be present on the surface based on measurement of a signal correlating to a substance at least partially obstructing the passage of fluid through the open port of the distal tip.

In one aspect, the signal may be a pressure signal and the detection apparatus further includes a pressure sensor configured and disposed to detect the pressure signal. The proximal pump portion may include the pressure sensor.

In one aspect, the apparatus may further include a pressure sensing portion disposed between the proximal pump portion and the distal probe portion wherein the pressure sensor is disposed in fluid communication with the pressure sensing portion to detect the pressure signal. The proximal pump portion, the pressure sensing portion and the distal probe portion may each define internal volumes summing to a total volume of the detection apparatus such that the detection apparatus forms an acoustical low pass filter.

In another aspect, the proximal pump portion may include a moveable plunger disposed therewithin and configured and disposed such that the moveable plunger is reciprocally moveable away from a proximal end of the proximal pump portion towards a distal end of the proximal pump portion. The movement of the plunger induces thereby a volumetric or mass flow in the distal probe portion or wherein the proximal pump portion comprises a moveable diaphragm, the movement of the diaphragm inducing thereby a change in volumetric or mass flow in the distal probe portion.

The apparatus may further include a controller. The controller may process pressure readings sensed by the pressure sensor and determine whether the pressure readings are indicative of a substance obstructing the passage of fluid through the open port of the distal tip. The substance may be dental plaque.

In yet another aspect of the apparatus, the signal represents strain of the probe portion. The detection apparatus may further include a strain gauge configured and disposed on the distal probe portion to enable the strain gauge to detect and measure the signal representing strain of the probe portion.

In one aspect, the distal tip having an open port may be chamfered at an angle such that passage of the second fluid through the distal tip is enabled when the distal tip touches the surface. The angle of the chamfer of the open port may be such that passage of the second fluid through the distal tip is at least partially obstructed when the distal tip touches the surface and a substance at least partially obstructs the passage of fluid through the open port of the distal tip.

Yet another aspect of the present disclosure includes a proximal body portion that includes a pump portion, a proximal probe portion wherein the pump portion and the proximal probe portion are in fluid communication with one another, and a connector wherein the proximal probe portion can be connected via the connector to a distal probe portion of a distal probe portion of the detection apparatus to establish fluid communication between the proximal probe portion and the distal probe portion. The detection apparatus includes a distal probe portion configured to be immersed in a first fluid. The distal probe portion defines a distal tip having an open port to enable the passage of a second fluid therethrough. The apparatus is configured such that passage of the second fluid through the distal tip enables detection of a substance that may be present on the surface based on measurement of a signal, correlating to a substance at least partially obstructing the passage of fluid through the open port of the distal tip.

Yet another aspect of the present disclosure includes a system for detecting the presence of a substance on a surface. The system includes a first detection apparatus as described above and at least a second detection configured in the manner as the first detection apparatus as described above.

Yet another aspect of the present disclosure includes a method of detecting the presence of a substance on a surface that includes, via a stream probe tubular member or stream probe defining a proximal end and an interior channel that includes a distal probe tip having an open port enabling the passage of a fluid medium therethrough, disposing the probe tip in proximity to a surface and such that the stream probe tubular member is immersed in a first fluid medium, causing a second fluid medium to flow through the interior channel and the distal probe tip and causing the distal probe tip to touch the surface in an interaction zone occurring in the first fluid medium, and probing the properties of the interaction zone via detection of at least partial obstruction of flow of the second fluid medium through the interior channel or the distal probe tip or combinations thereof.

Yet another aspect of the present disclosure includes a method of detecting the presence of a substance on a surface that includes, via at least two stream probe tubular members or stream probes each defining a proximal end and an interior channel that includes a distal probe tip having an open port enabling the passage of a fluid medium therethrough, disposing the two probe tips in proximity to a surface and such that the two stream probe tubular members or stream probes are immersed in a first fluid medium, causing a second fluid medium to flow through the interior channels and the distal probe tips and causing the distal probe tips to touch the surface in an interaction zone occurring in the first fluid medium, and probing the properties of the interaction zone via detection of at least partial obstruction of flow of the second fluid medium through the interior channels or the distal probe tips or combinations thereof.

In one aspect, the detection of at least partial obstruction of flow of the second fluid medium through the interior channels and the distal probe tips may include detection of a difference between a pressure signal detected in one of the two stream probe tubular members and another one of the two stream probe tubular members.

In another aspect, the detection of at least partial obstruction of flow of the second fluid medium through the interior channels and the distal probe tips may include detection of a difference between a strain signal detected in one of the two stream probe tubular members and another one of the two stream probe tubular members.

In yet a another aspect, the distal tip has an open port that may be chamfered at an angle such that the step of causing a second fluid medium to flow through the interior channels and the distal probe tips is enabled when the distal tip touches the surface and the second fluid medium is enabled to flow through the chamfered open port.

In a further aspect, the step of detecting at least partial obstruction of flow of the second fluid medium through at least one of the interior channels and the distal probe tips is enabled via the angle of the chamfer of the open port being such that passage of the second fluid through the distal tip is at least partially obstructed when the distal tip touches the surface and a substance at least partially obstructs the passage of the second fluid medium through the open port of the distal tip.

In one aspect, the probing of the properties of the interaction zone may include measuring a property of dental plaque derived from the surface in the interaction zone.

In still another aspect, the causing a second fluid medium to flow through the interior channels and the distal probe tips may be performed either by causing the second fluid medium to flow distally from the proximal ends of the at least two stream probe tubular members through the distal probe tips or by causing the second fluid medium to flow proximally from the distal probe tips through the interior channels towards the proximal ends of the stream probe tubular members.

The present disclosure describes a method of probing a dental surface by recording the outflow properties of a fluid medium through a probe tip. The properties of the fluid outflowing from the probe tip can for example be measured by recording the pressure of the fluid medium as a function of time. The release properties of fluid, including bubbles, from the tip-surface region can characterize the dental surface and/or the viscoelastic properties of dental material present at the probe tip. The fluid, including bubbles, may also improve the plaque removal rate of the tooth brush.

Novel features of exemplary embodiments of the present disclosure are:

(a) a fluid medium is brought in contact with a surface at a probe tip, generating an interaction zone between the tip and the surface; and (b) the shape and/or dynamics of the medium in the interaction zone depend on the properties of the surface and/or on materials derived from the surface; and (c) the pressure and/or shape and/or dynamics of the medium in the interaction zone are detected.

A determination is made by a controller as to whether a level of plaque is detected at a particular dental surface of a tooth that exceeds a predetermined maximum acceptable or permissible level of plaque.

If a negative detection is made, a signal is transmitted to the user of the electric toothbrush having an integrated stream probe plaque detection system to advance the brush to an adjacent tooth or other teeth.

Alternatively, if a positive detection is made, a signal is transmitted to the user of the electric toothbrush having an integrated stream probe plaque detection system to continue brushing the particular tooth.

Accordingly, the embodiments of the present disclosure relate to an apparatus that is configured such that passage of a fluid through an open port of a distal tip enables detection of a substance that may be present on a surface, e.g., a surface of a tooth, based on measurement of a signal correlating to a substance at least partially obstructing the passage of fluid through the open port. The apparatus includes a proximal pump portion and at least one distal probe portion configured to be immersed in another fluid. The apparatus may be included within a corresponding system that includes at least two apparatuses. A method includes probing an interaction zone for at least partial obstruction of flow.

In one exemplary embodiment, the first fluid may also pass through the open port of the distal tip of the distal probe portion, e. g., when the pressure within the distal probe portion is below ambient pressure.

To enhance the effectiveness of the method to reduce the occurrence of false positive signals when the stream probe tubular member is positioned on the gums, it is beneficial to distinguish between gums and plaque. Consequently, according to one exemplary embodiment of the present disclosure, a detection apparatus such as a toothbrush with plaque detection features includes a first stream probe to detect the plaque and a second stream probe to detect only gums. By comparing both signals, the detection apparatus is able to distinguish between gums versus plaque. The detection apparatus for detecting the presence of a substance on a surface includes a distal probe portion of a first stream probe. The distal probe portion is configured to be immersed in a first fluid. The distal probe portion of the first stream probe defines a distal tip having an open port to enable the passage of a second fluid therethrough. The distal tip has a size and shape configured to detect a substance that may be present on a surface by a subject or of a user of the detection apparatus. The detection apparatus includes a distal probe portion of a second stream probe. The first distal probe portion of the second stream probe is configured to be immersed in the first fluid and defines a distal tip having an open port to enable the passage therethough of the second fluid. The distal tip has a size and shape configured to detect placement of the distal tip on the gums of a subject or a user of the detection apparatus. The detection apparatus is configured such that passage of the second fluid through the distal tip of the distal probe portion of the first stream probe and passage of the second fluid through the distal tip of the distal probe portion of the second stream probe enables detection of a substance that may be present on the surface based on measurement of a signal, correlating to a substance at least partially obstructing the passage of the second fluid through the open port of the distal tip of the distal probe portion of the first stream probe and confirmation that the substance is not the gums of a subject or a user of the detection apparatus and not the generation of a false alarm signal that the substance is the gums of the subject or of the user of the detection apparatus. The confirmation is effected by comparison between the measurement of a signal correlating to a substance at least partially obstructing the passage of fluid through the open port of the distal tip of the distal probe portion of the first stream probe and measurement of a signal correlating to an object not obstructing the passage of fluid through the open port of the distal tip of the distal probe portion of the second stream probe.

In one exemplary embodiment, the distal probe portion of the first stream probe defines a longitudinal axis and the distal probe portion of the second stream probe defines a longitudinal axis and each define a circular cross-section in a direction transverse to the respective longitudinal axes. The open port of the distal tip of the distal probe portion of the second stream probe may be arranged concentrically around the open port of the distal tip of the distal probe portion of the first stream probe. The distal probe portion of the first stream probe and the distal probe portion of the second stream probe may define the common longitudinal axis and the distal tip of the distal probe portion of the first steam probe and the distal tip of the distal probe portion of the second stream probe may each define a concave profile in a direction transverse to the common longitudinal axis and with respect to respective proximal ends defined with respect to the common longitudinal axis, of the distal probe portion of the first stream probe and the distal probe portion of the second stream probe.

In another exemplary embodiment, the distal probe portion of the first stream probe and the distal probe portion of the second stream probe define the common longitudinal axis, and the distal tip of the distal probe portion of the first stream probe and the distal tip of the distal probe portion of the second stream probe may each define a convex profile in a direction transverse to the common longitudinal axis and with respect to respective proximal ends, defined with respect to the common longitudinal axis, of the distal probe portion of the first stream probe and the distal probe portion of the second stream probe.

In still another exemplary embodiment, the distal probe portion of the first stream probe and the distal probe portion of the second stream probe define the common longitudinal axis, and the distal tip of the distal probe portion of the first stream probe may define a concave profile with respect to the distal tip along the common longitudinal axis and the distal tip of the distal probe portion of the second stream probe may define a convex profile with respect to the distal tip along the common longitudinal axis and with respect to respective proximal ends, defined with respect to the common longitudinal axis, of the distal probe portion of the first stream probe and the distal probe portion of the second stream probe.

In one exemplary embodiment, the distal probe portion of the first stream probe and the distal probe portion of the second stream probe may be disposed in proximity to one another and such that the longitudinal axes are parallel to one another.

In a further aspect, in one exemplary embodiment, the detection apparatus may further include a proximal body portion including a pump portion, a proximal probe portion of the first stream probe and a proximal probe portion of the second stream probe wherein the proximal pump portion, the proximal probe portion of the first stream probe the distal probe portion of the first stream probe, the proximal probe portion of the second stream probe and the distal probe portion of the second stream probe are in fluid communication with one another.

In another exemplary embodiment, the signal may be a pressure signal and the detection apparatus may further include a pressure sensor configured and disposed to detect a pressure signal in the proximal portion of the first stream probe; and a pressure sensor configured and disposed to detect a pressure signal in the proximal portion of the second stream probe. The detection apparatus may further include a restriction orifice disposed in the proximal portion of the first stream probe: and a restriction orifice disposed in the proximal portion of the second stream probe. In one exemplary embodiment, the proximal probe portion of the second stream probe is arranged concentrically around the proximal probe portion of the first stream probe.

In a still further exemplary embodiment, the pump portion the proximal probe portion of the first stream probe; and the proximal probe portion of the second stream probe are removably attachable to the distal probe portion of the first stream probe and to the distal probe portion of the second stream probe, respectively.

Alternatively, in another exemplary embodiment, the distal probe portion of first stream probe is integrally joined with the proximal probe portion of the first stream probe, and the distal probe portion of second stream probe is integrally joined with the proximal probe portion of the second stream probe.

In a further aspect, in one exemplary embodiment, the detection apparatus may further include a controller wherein the controller processes pressure readings sensed by the pressure sensor and determines whether the pressure readings are indicative of detection of a substance that may be present on the surface based on measurement of a signal, correlating to a substance at least partially obstructing the passage of second fluid through the open port of the distal tip of the distal probe portion of the first stream probe and confirmation that the substance is not the gums of the subject or of the user of the detection apparatus or generation of a false positive alarm signal that the substance is the gums of the subject or of the user of the detection apparatus, the confirmation effected by comparison between the measurement of the signal correlating to a substance at least partially obstructing the passage of second fluid through the open port of the distal tip of the distal probe portion of the first stream probe and measurement of a signal correlating to an object not obstructing the passage of second fluid through the open port of the distal tip of the distal probe portion of the second stream probe.

Other exemplary embodiments of a detection apparatus for detecting the presence of a substance on a surface according to the present disclosure to override false positive signals triggered by the first stream probe being placed on the gums of the user or of the subject and falsely signaling the presence of plaque. More particularly, an optical gum detector according to embodiments of the present disclosure provides a solution for false positive signals using the stream probes for plaque detection as described above, i.e., the false positive signals occur due to blocking of the stream probe on gum that may be interpreted as plaque.

The basis for applying an optical gum detector is to measure the ratio in reflected light for wavelengths below and above the sharp transition at 600 nm wavelength in the reflectivity of gums. This reflectivity ratio displays a good contrast between gum and teeth. A threshold can be set to distinguish between a stream probe position on gum and a stream probe position on a tooth or teeth, thereby overriding false positive signals for plaque detection by the stream probe.

Accordingly, a dental hygiene detection apparatus for detecting the presence of a substance on a surface according the present disclosure includes a distal oral insertion portion defining a proximal end and a distal end and includes a distal probe portion of a stream probe that is configured to be immersed in a first fluid. The distal probe portion defines a distal tip having an open port to enable passage of a second fluid therethrough The distal tip has a size and shape configured to detect a substance that may be present on a surface. The distal oral insertion portion includes a distal optical gum detector transmission portion that defines a proximal end and a distal tip. The distal tip of the distal optical gum detector transmission portion extends to the vicinity of the distal end of the distal oral insertion portion. The distal oral insertion portion includes a distal optical gum detector reception portion that defines a proximal end and a distal tip. The distal optical gum detector reception portion extends to the vicinity of the distal end of the distal oral insertion portion. The detection apparatus is configured such that passage of the second fluid through the distal tip of the distal probe portion enables detection of a substance that may be present on the surface based on measurement of a stream probe signal correlating a substance at least partially obstructing the passage of fluid through the open port of the distal tip of the distal probe portion. The detection apparatus is also configured such that the distal optical gum detector transmission portion and the distal optical gum detector reception portion are in a position to transmit and to receive, respectively, an optical signal that upon transmission of the optical signal and reception of the optical signal by a controller enables the controller to determine if the open port of the distal tip of the distal probe portion is in contact with a substance at least partially obstructing the passage of fluid through the open port and not in contact with the gums of a subject or of a user of the detection apparatus.

In one exemplary embodiment, the distal optical gum detector transmission portion may include a first distal transmitting optical fibre defining a proximal end and a distal tip extending to the vicinity of the distal end of the distal oral insertion portion and the distal optical gum detector transmission portion may further include a second distal transmitting optical fibre defining a proximal end and a distal tip wherein the distal tip of the second distal transmitting optical fibre extends to the vicinity of the distal end of the distal oral insertion portion.

In yet another exemplary embodiment, the dental hygiene detection apparatus further includes a proximal body portion that includes a proximal optical gum detector transmission portion that is optically coupled to the distal optical gum detector transmitting portion.

In one exemplary embodiment, the proximal optical gum detector transmission portion includes a dichroic cube defining a light transmitting surface and the dichroic cube is optically coupled to the first proximal transmitting fibre via an optical lens that is disposed to focus light emitted from the light transmitting surface of the dichroic cube through the first proximal transmitting fibre. The dichroic cube may further include a first light receiving surface and a second light receiving surface. The proximal optical gum detector transmission portion may further include a first light emitting diode and another optical lens disposed between the first light emitting diode and the first light receiving surface to focus light emitted from the first light emitting diode into the first light receiving surface and a second light emitting diode and yet another optical lens disposed between the second light emitting diode and the second light receiving surface to focus light emitted from the second light emitting diode into the second light receiving surface.

In a still further exemplary embodiment, the proximal optical gum detector transmission portion includes a first proximal optical transmitting fibre wherein the proximal body portion may further include an optical combiner that is optically coupled to the first proximal optical transmitting fibre.

The proximal optical gum detector transmission portion may further include a first light emitting diode and a second light emitting diode. Each diode may be optically coupled to the optical combiner to transmit light from the first and second light emitting diodes to the distal optical gum detector transmission portion in the distal oral insertion portion.

In yet another exemplary embodiment, the proximal optical gum detector transmission portion includes a first proximal transmitting optical fiber and the proximal optical gum detector transmission portion further includes a light emitting diode that is optically coupled to the first proximal transmitting optical fibre.

In a still further exemplary embodiment, the proximal body portion may further include a proximal optical gum detector reception portion that is optically coupled to the distal optical gum detector receiving portion.

In another exemplary embodiment, the distal optical gum detector reception portion comprises a first distal receiving optical fibre and the proximal optical gum detector reception portion includes a first proximal receiving fibre that is optically coupled to the first distal receiving optical fibre.

In a still further exemplary embodiment, the proximal optical gum detector reception portion further includes an optical detector that is optically coupled to the first proximal receiving optical fibre. The proximal optical gum detector reception portion may further include a second optical detector optically coupled to the first proximal receiving optical fibre.

In yet another exemplary embodiment, the proximal optical gum detector transmission portion includes a first proximal optical transmitting fibre and a light emitting diode that is optically coupled to the first proximal transmitting optical fibre.

In another exemplary embodiment, the proximal optical gum detector transmission portion may further include a second proximal optical transmitting fibre and a light emitting diode that is optically coupled to the second proximal transmitting optical fibre.

In a further exemplary embodiment, the stream probe signal is a pressure signal and the detection apparatus further includes a pressure sensor that is configured and disposed to detect the pressure signal in the proximal probe portion of the stream probe.

In one exemplary embodiment, the dental hygiene detection apparatus may further include a controller wherein the controller processes pressure readings sensed by the pressure sensor and determines whether the pressure readings are indicative of detection of a substance that may be present on the surface based on measurement of a signal correlating to a substance at least partially obstructing the passage of the second fluid through the open port of the distal tip of the distal probe portion of the stream probe and confirmation via the distal optical gum detector transmission portion and the distal optical gum detector reception portion transmitting and receiving, respectively, an optical signal that upon transmission of the optical signal and reception of the optical signal by the controller, enables the controller to determine if the open port of the distal tip of the distal probe portion is in contact with a substance at least partially obstructing the passage of fluid through the open port of the distal tip of the distal probe portion and not in contact with the gums of a subject or of a user of the detection apparatus.

These and other aspects of the present disclosure will be apparent from and elucidated with reference to the embodiment(s) described hereinafter.

BRIEF DESCRIPTION OF THE DRAWINGS

The aspects of the present disclosure may be better understood with reference to the following figures. The components in the figures are not necessarily to scale, emphasis instead being placed upon clearly illustrating the principles of the disclosure. Moreover, in the figures, like reference numerals designate corresponding parts throughout the several views.

In the figures:

FIG. 28 illustrates another alternate exemplary embodiment of the distal probe portions of the first and second stream probes of FIG. 27 except that the distal probe portion of the second stream probe defines an arcuate, non-circular cross section in the direction transverse to its longitudinal axis in a similar manner to the second stream probes of FIGS. 26A-26C;

DETAILED DESCRIPTION OF EMBODIMENTS

The present disclosure describes various embodiments of systems, devices, and methods related to assisting users to clean their teeth, in particular by informing users if they are indeed removing plaque from their teeth and if they have fully removed the plaque, providing both reassurance and coaching them into good habits. In one exemplary embodiment, the information is provided in real time during brushing, as otherwise consumer acceptance is likely to be low. For example, it is useful if a toothbrush gives the user a signal when the position at which they are brushing is clean, so they can move to the next tooth. This may reduce their brushing time, but will also lead to a better, more conscious brushing routine.

A particular goal of utilization of the exemplary embodiments of the present disclosure is to be able to detect plaque within a vibrating brush system surrounded with toothpaste foam, e.g., a Philips Sonicare toothbrush. The detection system should provide contrast between a surface with the thicker, removable plaque layers, and a more clean pellicle/calculus/thin plaque/tooth surface.

As defined herein, the term "is coupled to" may also be interpreted as "is configured to be coupled to". The term "to transmit" may also be interpreted as "to enable transmission of". The term "to receive" may also be interpreted as "to enable reception of".

Figure 1:
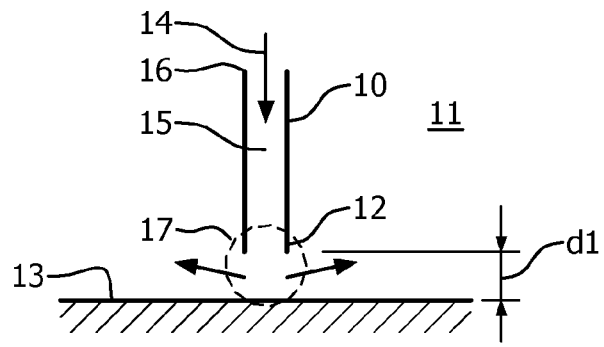
FIG. 1 illustrates the general principle of a stream probe impacting a dental surface in accordance with the present disclosure.

FIG. 1 illustrates a method of detecting the presence of a substance on a surface, e.g., a substance such as dental plaque on a surface such as tooth enamel, using a stream probe 10 according to one exemplary embodiment of the present disclosure. The stream probe 10, exemplarily illustrated as a cylindrical tube member, defines a proximal end 16, an interior channel 15 and a distal probe tip 12. The interior channel 15 contains a fluid medium 14, e.g. a gas or a liquid. The probe tip 12 is placed in the proximity of a surface 13, e.g. a dental surface. The probe 10 is immersed in a fluid medium 11, e.g. an aqueous solution such as a dental cleaning solution. Probe fluid medium 14 flows through the probe channel 15 and touches surface 13 in interaction zone 17. The properties of the interaction zone 17 are probed via the outflow of probe medium 14.

As described in more detail below with respect to FIG. 10, an apparatus or instrument for detecting the presence of a substance on a surface, such as a dental cleaning instrument including an electric toothbrush having an integrated stream probe plaque detection system, is configured such that fluid medium 14 is brought in contact with surface 13, e.g. a dental surface, at probe tip 12, generating interaction zone 17 between distal tip 12 and surface 13.

The shape and/or dynamics of the medium 14 in the interaction zone 17 depend on the properties of the surface 13 and/or on materials derived from the surface 13, the pressure and/or shape and/or dynamics of the medium 14 in the interaction zone 17 are detected and a determination is made by a controller as to whether a predetermined maximum acceptable level of plaque is detected at the particular dental surface 13, as described in more detail below with respect to FIG. 10.

More particularly, when medium 14 is a gas 30 (see FIG. 2), then a gas meniscus will appear at the tip 12 and will become in contact with surface 13. The shape and dynamics of the gas at the tip will depend on the properties of the probe tip 12 (e.g. tip material, surface energy, shape, diameter, roughness), properties of solution 11 (e.g. materials composition), properties of medium 14 (e.g. pressure, flow speed), and properties of surface 13 (e.g. viscoelastic properties, surface tension) and/or on materials derived from the surface 13 (viscoelastic properties, adherence to surface, texture etc.).

Figure 2:
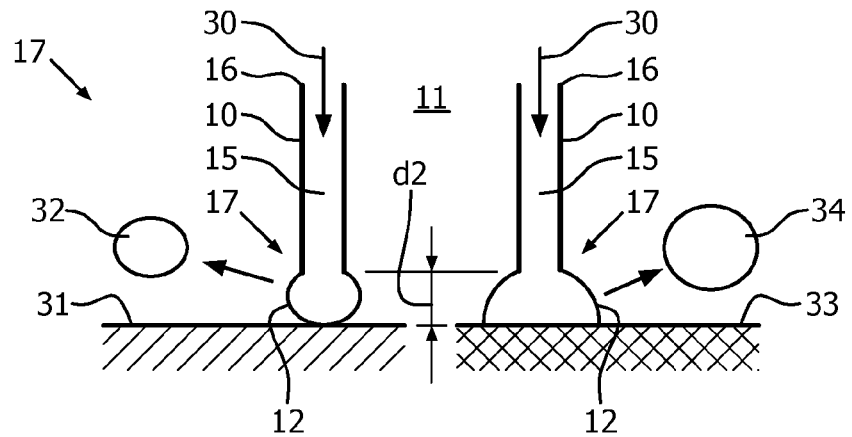
FIG. 2 illustrates the effect of surface tension on a less hydrophilic surface and on a more hydrophilic surface for a stream probe impacting a dental surface in accordance with one exemplary embodiment off the present disclosure.

FIG. 2 illustrates the influence of surface tension. In the case of a surface with a high surface energy or a strongly hydrated surface, e.g. a hydrophilic surface 31 such as the surface of plaque as illustrated in the left photograph, the gas 30 will not easily displace the aqueous medium 11 from the surface 31 near the interaction zone 17.

In the case of a surface with a low surface energy or a less hydrated surface, e.g. a less hydrophilic surface 33 such as the enamel surface of a tooth as illustrated in the right photograph, the gas 30 more easily displaces the aqueous medium 11 from the surface 33. The properties (shape, pressure, release rate, etc) of bubbles 32 and 34 depend on the surface tension of the dental surface 31 or 33. This is referred to as the bubble method. That is, the stream probe or distal probe portion 10 is configured such that passage of the second fluid such as the gas 30 through the distal tip 12 enables detection of a substance that may be present on the surface 31 or 33 based on measurement of a signal correlating to, in proximity to the surface 31 or 33, one or more bubbles 32 or 34 generated by the second fluid such as the gas 30 in the first fluid such as the aqueous medium 11.

Figure 3:
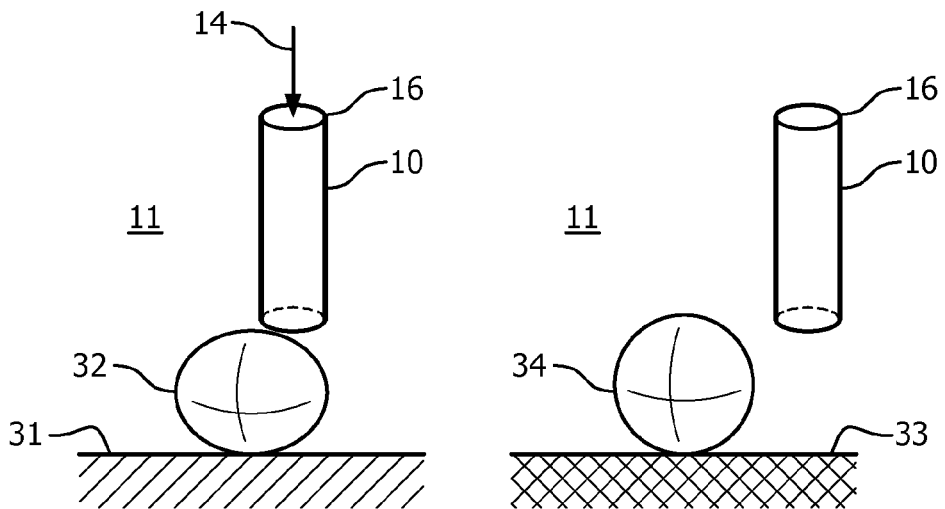
FIG. 3 illustrates left and right photographs of air bubbles from a needle in water touching a plaque surface on the left and an enamel surface on the right in accordance with one exemplary embodiment of the present disclosure.

FIG. 3 illustrates photographs of such types of air bubbles 32 and 34 from stream probe 10 under aqueous solution 11, e.g., water. As illustrated in the left photograph, an air bubble 32 does not stick on a wet plaque layer 31, while, as illustrated in the right photograph, air bubble 34 does stick on enamel surface 33, showing that the plaque layer 31 is more hydrophilic as compared to enamel surface 33.

Figure 4A:
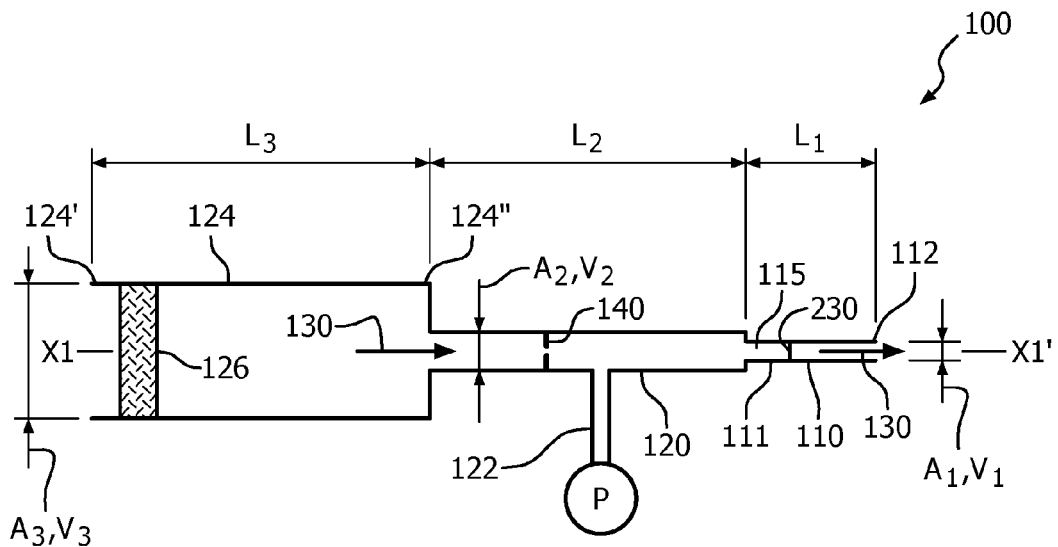
FIG. 4A illustrates one exemplary embodiment of the present disclosure of a stream probe having a pump portion supplying a continuous stream of gas via a tube to a probe tip while measuring the internal tube pressure.
Figure 4B:
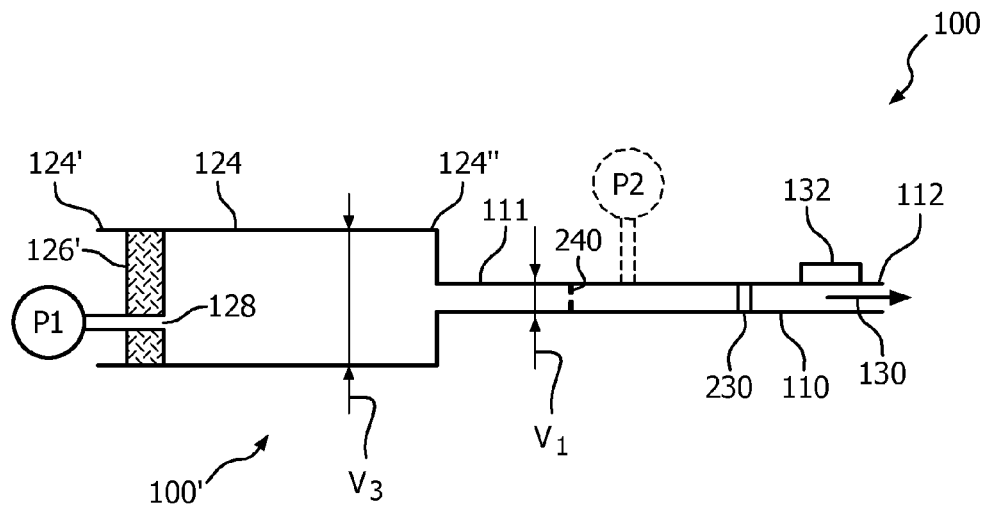
FIG. 4B illustrates another exemplary embodiment of the stream probe of FIG. 4A having one exemplary embodiment of a pump portion supplying a continuous stream of gas via a tube to a probe tip while measuring the internal pump pressure.
Figure 4C:
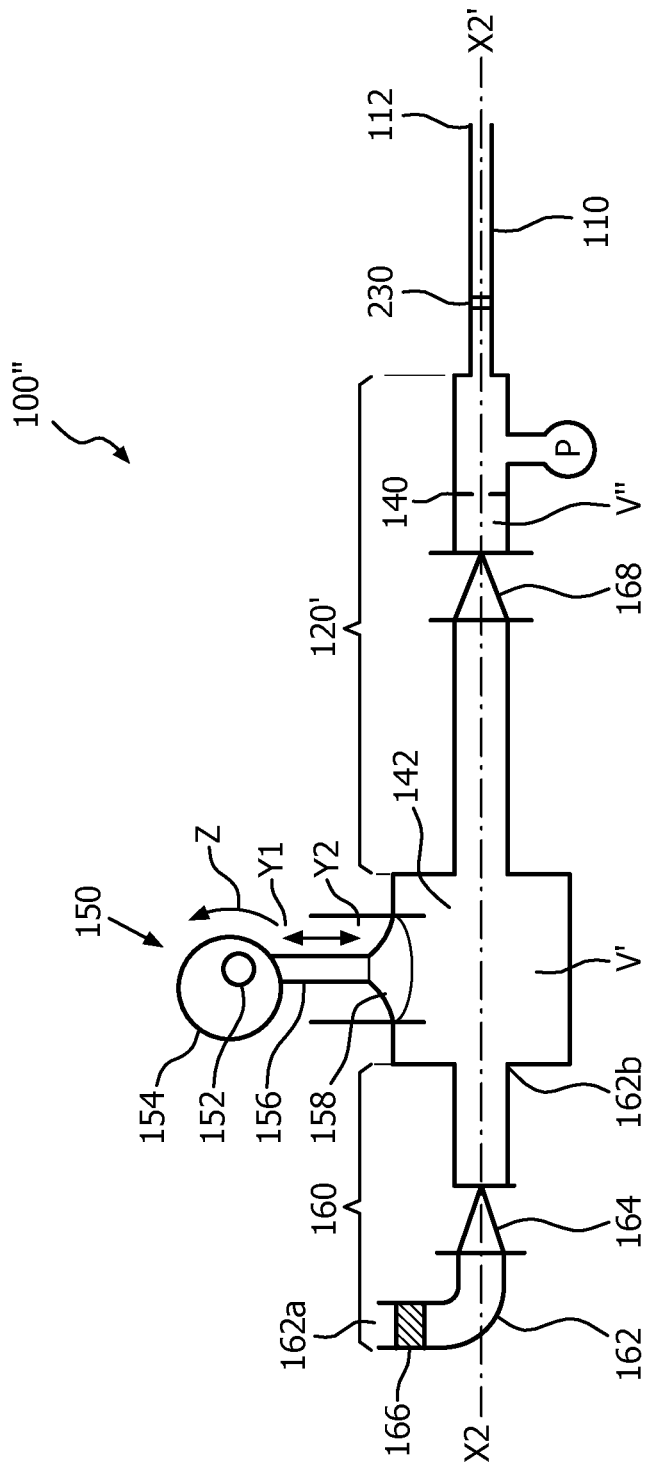
FIG. 4C illustrates another exemplary embodiment of the stream probe of FIGS. 4A and 4B having another exemplary embodiment of a pump portion supplying a generally continuous stream of gas via a tube to a probe tip while measuring the internal pump pressure.

FIGS. 4A, 4B and 4C each illustrate a detection apparatus or instrument for detecting the presence of a substance on a surface according to exemplary embodiments of the present disclosure, wherein the detection apparatus is exemplified by a stream probe that includes a parameter sensor to demonstrate the principle of plaque detection by parameter sensing and measurement. As defined herein, a parameter sensor includes a pressure sensor or a strain sensor or a flow sensor, or combinations thereof, which sense a physical measurement represented by a signal that is indicative of blockage of flow in the stream probe which may, in turn, be indicative of plaque or other substance blocking flow in the stream probe. A flow sensor which measures differential pressure or flow of heat from a wire which has been heated above ambient temperature are flow sensors or other means known or to be conceived for pressure, strain or flow or other measurement, including chemical or biological measurements, are included within the definition of a parameter sensor which sense a physical measurement represented by a signal that is indicative of blockage of flow in the stream probe which may be indicative of plaque or other substance blocking flow in the stream probe. For simplicity, for the purposes of description, the parameter sensor or sensors are exemplified by one or more pressure sensors. Although the locations for the parameter sensors illustrated in the figures are intended to apply generically to each different type of parameter, those skilled in the art will recognize that the location of the parameter sensor may be adjusted, if necessary, from the location or locations shown in the drawings, depending on the specific type of parameter sensor or sensors being employed. The embodiments are not limited in this context.

More particularly, in FIG. 4A, a stream probe 100 includes a proximal pump portion 124 such as a tubular syringe portion as shown, a central parameter sensing portion 120, exemplarily having a tubular configuration as shown, and a distal probe portion 110, also exemplarily having a tubular configuration as shown, defining a distal probe tip 112. The distal tubular probe portion 110 defines a first length L1 and a first cross-sectional area A1, the central parameter sensing tubular portion 120 defines a second length L2 and a second cross-sectional area A2, while the proximal tubular syringe portion 124 defines a third length L3 and a third cross-sectional area A3. The proximal tubular syringe portion 124 includes, e.g., in the exemplary embodiment of FIG. 4A, a reciprocally movable plunger 126 initially disposed in the vicinity of proximal end 124'.

A continuous fluid steam 130 of air is supplied by the plunger 126 through the central parameter sensing portion tubular portion 120 to the probe tip 112 when the plunger moves longitudinally along the length L3 at a constant velocity and away from the proximal end 124'. When the fluid stream 130 is a gas, a continuous stream 130 of gas is supplied through the plunger 126 (such as via an aperture 128 in the plunger 126 (see plunger 126' in FIG. 4B) or from a branch connection 122 connecting to the central parameter sensing tubular portion 120 to the probe tip 112. In one exemplary embodiment, at a location upstream from the branch connection 122, a restriction orifice 140 may be disposed in the central parameter sensing tubular portion 120.

As the plunger 126 moves along the length L3 towards distal end 124" of the proximal tubular syringe portion 124, the pressure inside the central parameter sensing tubular portion 120 is measured (downstream of restriction orifice 140 when the restriction orifice 140 is present) using pressure meter P that is in fluid communication with the central parameter sensing tubular portion 120 and the distal tubular probe portion 110 via the branch connection 122.

When the plunger 126 moves the pressure at pressure meter P versus time characterizes the interaction of the gas meniscus at the tip 112 of the probe 110 with the surface (see FIG. 1, surface 13, and FIGS. 2 and 3, surfaces 31 and 33). The presence of the restriction orifice 140 improves the response time of the pressure meter P since only the volume of the stream probe 100 downstream of the restriction orifice 140 is relevant and the stream probe 100 behaves more closely or approximately as a flow source rather than a pressure source. The volume upstream of the restriction orifice 140 becomes less relevant.

For the bubble method, the pressure difference is generally constant, which means that the bubble size varies and so the bubble rate varies with constant plunger velocity, because the volume in the system changes. A reciprocally moveable plunger may be used to obtain a generally fixed bubble rate. As described above, in one exemplary embodiment, the pressure sensor P may function either alternatively or additionally as a flow sensor, e.g., as a differential pressure sensor. Those skilled in the art will recognize that flow of the fluid stream or second fluid 130 through the distal probe tip 112 may be detected by means other than pressure sensors such as pressure sensor P, e.g., acoustically or thermally. The embodiments are not limited in this context. Consequently, the movement of the plunger 126 induces a change in pressure or volumetric or mass flow through the distal probe tip 112.

Figure 5:
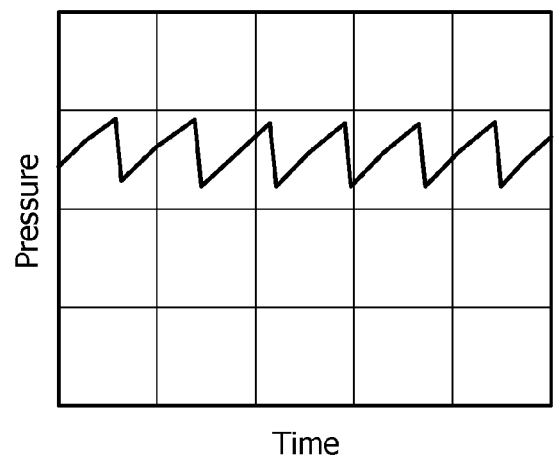
FIG. 5 illustrates a sample pressure measurement of the stream probe of FIG. 4A as a function of time.

FIG. 5 illustrates an example of a pressure signal (measured in Newtons/sq. meter, $N/m^2$) as a function of time (1 division corresponds with a second) utilizing the stream probe 100 of FIG. 4A. The regular variation of the signal is caused by the regular release of gas bubbles at the probe tip 112.

The sensitivity of the pressure readings can be increased by carefully choosing the dimensions of the components. The total volume VI (equal to A1×L1) plus volume V2 (equal to A2×L2) plus volume V3 (equal to A3×L3) from both the tube 120 and the syringe 124 together with the probe 110, form an acoustical low-pass filter. In the exemplary stream probe 100 of FIG. 4A, the cross-sectional area A3 is greater than the cross-sectional area A2 which in turn is greater than the cross-sectional area A1. The gas flow resistance in the system should be designed small enough to have a good system response time. When bubble-induced pressure differences are recorded, then the ratio between bubble volume and total system volume should be large enough to have a sufficient pressure difference signal due to air bubble release at the probe tip 112. Also the thermoviscous losses of the pressure wave interacting with the walls of tube 120 as well as the probe 110 must be taken into account, as they can lead to a loss of signal.

In the stream probe 100 illustrated in FIG. 4A, the three volumes differ from one another as an example. However, the three volumes could be equal to one another or the pump volume could be less than the probe volume.

FIG. 4B illustrates an alternate exemplary embodiment of a stream probe according to the present disclosure. More particularly, in stream probe 100', the central parameter sensing portion 120 of stream probe 100 in FIG. 4A is omitted and stream probe 100' includes only proximal pump portion 124 and distal probe portion 110. A pressure sensor P1 is now exemplarily positioned at plunger 126' to sense pressure in the proximal pump portion 124 via an aperture 128 in the plunger 126'.

Alternatively, a pressure sensor P2 may be positioned in the distal probe portion 110 at a mechanical connection 230. In a similar manner as described above with respect to FIG. 4A and restriction orifice 140, in one exemplary embodiment, a restriction orifice 240 may be disposed in the distal probe portion 110 upstream of the mechanical connection 230 and thus upstream of pressure sensor P2. Again, the presence of the restriction orifice 240 improves the response time of the pressure meter P2 since only the volume of the stream probe 100' downstream of the restriction orifice 240 is relevant and the stream probe 100' behaves more closely or approximately as a flow source rather than a pressure source. The volume upstream of the restriction orifice 240 becomes less relevant.

However, it should be noted that for the case of pressure sensor P1, the restriction orifice 240 is optional and is not required for proper sensing of the pressure in distal probe portion 110.

In one exemplary embodiment, the pressure sensor P2 may function either alternatively or additionally as a flow sensor, e.g., as a differential pressure sensor. Those skilled in the art will recognize that flow of the second fluid through the distal probe tip 112 may be detected by means other than pressure sensors such as pressure sensor P2, e.g., acoustically or thermally. The embodiments are not limited in this context. Consequently, the movement of the plunger 126 induces a change in pressure or volumetric or mass flow through the distal probe tip 112.

In a similar manner as described with respect to stream probe 100 in FIG. 4A, volume V3 of the proximal pump portion 124 may be greater than volume V1 of the distal probe portion 110 in stream probe 100' in FIG. 4B, as illustrated. Alternatively, the two volumes may be equal to one another or volume V3 may be less than volume V1.

It should be noted that when restriction orifice 140 is present in stream probe 100 illustrated in FIG. 4A, the volume V3 and the portion of the volume V2 upstream of the restriction orifice 140 become less relevant to the pressure response as compared to the volume in the portion of volume V2 downstream of the restriction orifice 140 and the volume V1.

Similarly, when restriction orifice 240 is present in stream probe 100' illustrated in FIG. 4B, the volume V3 and the volume V1 upstream of restriction orifice 240 become less relevant to the pressure response as compared to the volume V1 downstream of the restriction orifice 240.

Additionally, those skilled in the art will recognize that the restriction of flow via orifices 140 and 240 may be effected by crimping central parameter sensing tubular portion 120 or distal probe portion 110 in lieu of installing a restriction orifice. As defined herein, a restriction orifice includes a crimped section of tubing.

Alternatively, a parameter sensor represented by strain gauge 132 may be disposed on the external surface of the distal probe 110. The strain gauge 132 may also be disposed on the external surface of the proximal pump portion 124 (not shown). The strain readings sensed by strain gauge 132 may be read directly or converted to pressure readings as a function of time to yield a readout similar to FIG. 5 as an alternative method to determine the release of gas bubbles at the probe tip 112.

FIG. 4C illustrates another exemplary embodiment of the stream probe more particularly of FIG. 4A and of FIG. 4B having another exemplary embodiment of a pump portion supplying a generally continuous stream of gas via a tube to a probe tip while sensing a parameter indicative of blockage of flow in the stream probe, which may, in turn, be indicative of plaque or other substance blocking flow in the stream probe. More particularly, stream probe 100" exemplifies a fluid pump designed to provide a generally continuous flow, which is generally advantageous in operation. Stream probe 100" is generally similar to stream probe 100 of FIG. 4A and includes distal probe portion 110 and distal probe tip 112 and central parameter sensing portion 120' which also includes parameter sensor P represented by a pressure sensor and also may include restriction orifice 140 upstream of the pressure sensor P.

Stream probe 100" differs from stream probe 100 in that proximal pump portion 124 is replaced by proximal pump portion 142 wherein, in place of reciprocating plunger 126, that reciprocates along center line axis X1-X1' of the proximal pump portion 124, diaphragm pump 150 reciprocates in a direction transverse to longitudinal axis X2-X2' of proximal pump portion 124, the direction of reciprocation of diaphragm pump 150 indicated by double arrow Y1-Y2, The diaphragm pump 150 includes a motor 152 (represented by a shaft) and an eccentric mechanism 154 which is operatively connected to a connecting rod or shaft 156 that in turn is operatively connected to a flexible or compressible diaphragm 158

An air intake supply path 160 is in fluid communication with proximal pump portion 142 to supply air from the ambient surroundings to the proximal pump portion 142. The air intake supply path 160 includes an intake conduit member 162 having a suction intake port 162a from the ambient air and a downstream connection 162b to the proximal pump portion 142, thereby providing fluid communication between the proximal pump portion 142 and the ambient air via the suction port 162a. A suction flow interruption device 164, e.g. a check valve, is disposed in the intake conduit member 162 between the suction port 162a and the downstream connection 162b. A suction intake filter 166, e.g. a membrane made from a porous material such as expanded polytetraflouroethylene ePTFE (sold under the trade name Gore-Tex® by W. L. Gore & Associates, Inc., Elkton, Md., USA) may be disposed in the air intake supply path 160 in the intake conduit member 162 upstream of the suction flow interruption device 164 and generally in proximity of the suction intake port 162a to facilitate periodic replacement.

The central parameter sensing portion 120' serves also as a discharge flow path for the proximal pump portion 142. A proximal pump portion discharge flow path flow interruption device 168, e.g., a check valve, is disposed in the central parameter sensing portion 120' upstream of the parameter sensor P and, when present, the restriction orifice 140.

Thus the distal tip 112 is in fluid communication with the suction intake port 162a of the air intake conduit member 162 of the air intake supply path 160 via the distal probe portion 110, the central parameter sensing portion 120' and the proximal pump portion 142.

During operation of the motor 152, the motor 152 rotates, in the direction indicated by arrow Z, the eccentric mechanism 154, thereby imparting a reciprocating motion to the connecting rod or shaft 156. When the connecting rod or shaft 156 moves in the direction of arrow Y1 towards the motor 152, the flexible or compressible diaphragm 158 moves also in the direction of arrow Y1 towards the motor 152, thereby causing a reduction in pressure within the interior volume V' of the proximal pump portion 142. The reduction in pressure causes pump portion discharge flow path flow interruption device 168 to close and causes the suction flow interruption device 164 to open, thereby drawing air through the suction intake port 162a.

The eccentric mechanism 154 continues to rotate in the direction of arrow Z, until the connecting rod or shaft 156 moves in the direction of arrow Y2 away from the motor 152 and towards the flexible or compressible diaphragm 158 such that the flexible or compressible diaphragm 158 moves also in the direction of arrow Y2 towards the interior volume V', thereby causing an increase in pressure within the interior volume V' of the proximal pump portion 142. The increase in pressure causes the suction flow interruption device 164 to close and the pump portion discharge flow path flow interruption device 168 to open, thereby causing air flow through the central parameter sensing portion 120' and the distal probe portion 110 through the distal tip 112.

When restriction orifice 140 is deployed and disposed in the central parameter sensing portion 120', which, as indicated above, serves also as a discharge flow path for the proximal pump portion 142, a low pass filter function is performed by volume V'" between pump portion discharge flow path flow interruption device 168 and restriction orifice 140. Thus, when restriction orifice 140 is deployed, pump portion discharge flow path flow interruption device 168 must be upstream of the restriction orifice 140. As a result, high frequency pulsations are filtered out of the air flow to the distal tip 112.

The piston or plunger 126, 126' of pump portion 124 of FIGS. 4A and 4B and liquid diaphragm pump 150 of FIG. 4C are examples of positive displacement pumps or compressors which may be employed to cause the desired changes in pressure at the distal tip 112 or the distal probe portion 110. Other types of positive displacement pumps or compressors, as well as centrifugal pumps or other types of pumps known in the art may be employed to cause the desired changes in pressure or flow at the distal tip 112.

Figure 6:
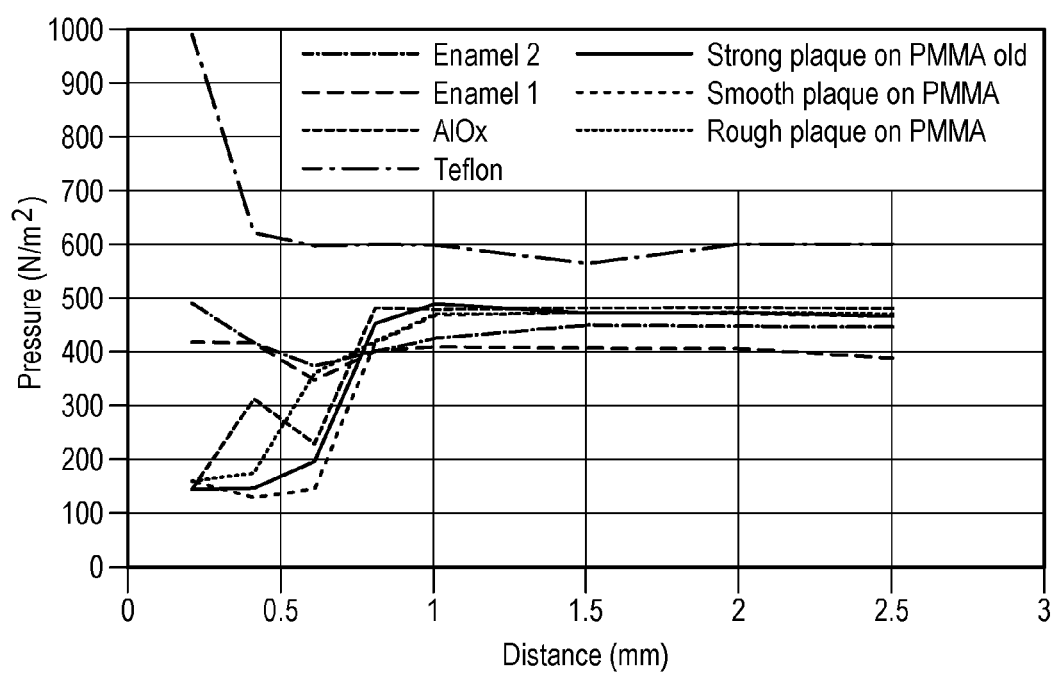
FIG. 6 illustrates a sample pressure signal amplitude as a function of distance of the probe tip of FIG. 4A to various dental surfaces.

FIG. 6 shows pressure amplitude data as a function of the distance d1 or d2 between probe tip 112 and surface 13 in FIG. 1 or surfaces 31 and 33 in FIG. 2, measured for different surfaces. A plastic needle with 0.42 mm inner diameter was used. Clear differences are visible at distances up to 0.6 mm, where the most hydrophobic surface (Teflon) gives the largest pressure signal, while the most hydrophilic surface (plaque) gives the lowest signal.

It should be noted that the data presented in FIGS. 5 and 6 were taken without the inclusion of restriction orifices.

FIGS. 1-6 have described a first method of detecting the presence of a substance on a surface, which includes the measurement of bubble release from a tip (by pressure and/or pressure variations and/or bubble size and/or bubble release rate) as a method of detecting, for example, dental plaque at the probe tip 112. As described above with respect to FIGS. 1 and 2 and 6, the probe tip 112 is positioned at a distance d1 or d2 away from the surface such as surface 13 in FIG. 1 or surfaces 31 and 33 in FIG. 2.

It should be noted that although the method of bubble generation and detection has been described with respect to the second fluid being a gas such as air, the method may also be effective when the second fluid is a liquid, wherein water droplets instead of gas bubbles are created.

Additionally, the method may be affected with constant pressure and measurement of the variable fluid outflow. The apparatus may record the variable pressure and/or the variable flow of the second fluid. In one exemplary embodiment, the pressure is recorded and the flow of the second fluid is controlled, e.g., the flow is kept constant. In another exemplary embodiment, the flow is recorded and the pressure of the second fluid is controlled, e.g., the pressure is kept constant.

Figure 7:
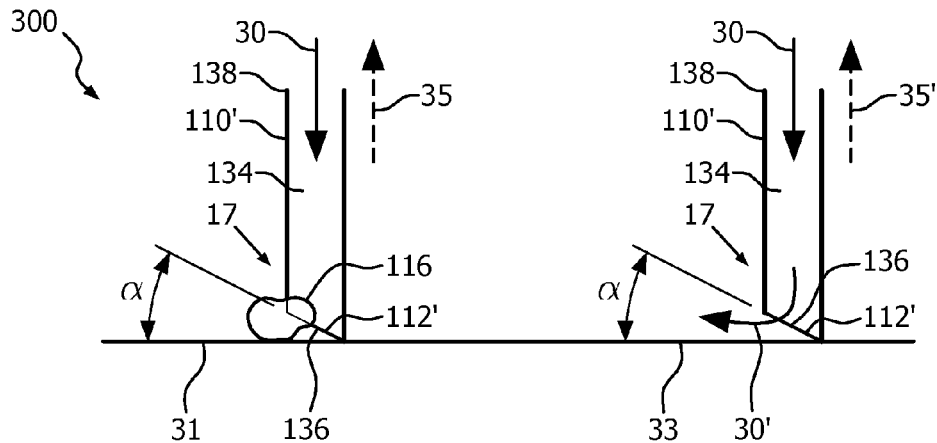
FIG. 7 illustrates a system for detecting the presence of a substance on a surface according to one exemplary embodiment of the present disclosure wherein on the left is illustrated one embodiment of a stream probe having a partial blockage from dental surface material such as dental plaque while on the right is illustrated one embodiment of an unblocked stream probe.

In a second method of detecting the presence of a substance on a surface according to the exemplary embodiments of the present disclosure, FIG. 7 illustrates the influence of blocking of the probe tip 112 of the probe 110 of FIG. 4A, 4B or 4C. The probe or stream probe tubular member or stream probe 110' illustrated in FIG. 7 includes a proximal end 138 and interior channel 134. The stream probe or stream probe tubular member 110' differs from stream probe 110 in FIG. 4A, 4B or 4C in that the stream probe 110' includes a chamfered or beveled distal tip 112' having an open port 136 that is chamfered at an angle $\alpha$ with respect to the horizontal surface 31 or 33 such that passage of the second fluid medium through the distal tip 112, now designated as second fluid medium 30' since it has exited from the distal tip 112', is enabled when the distal tip 112' touches the surface 31 or 33 and the second fluid medium 30' is also enabled to flow through the chamfered open port 136. The angle $\alpha$ of the chamfer of the open port 136 is such that passage of the second fluid medium 30' through the distal tip 112' is at least partially obstructed when the distal tip 112' touches the surface 31 or 33 and a substance 116, such as viscoelastic material 116, at least partially obstructs the passage of fluid through the open port 136 of the distal tip 112'. Although only one probe 110' is required to detect obstruction of the passage of fluid, in one exemplary embodiment, it may be desired to deploy at least two probes 110' as a system 3000 to detect obstruction of the passage of fluid (see the discussion below for FIGS. 13-17 and FIGS. 19-21).

Alternatively, the probe tips 112 of FIG. 1, 2, 4A or 4B are utilized without chamfered or beveled ends and simply held at an angle (such as angle $\alpha$) to the surface 31 or 33. In one exemplary embodiment, the substance has a nonzero contact angle with water. In one exemplary embodiment, the substance with a nonzero contact angle with water is enamel.

As illustrated on the left portion of FIG. 7, when the probe tip 112' becomes blocked by viscoelastic material 116 from the dental surface 31, then the fluid such as gas 30 will flow less easily out of the tip 112', as compared to when probe tip 112' is not blocked (second fluid medium 30') and is without dental material at the tip 112' or at dental surface 33, as illustrated in the right portion of FIG. 7.

Figure 8:
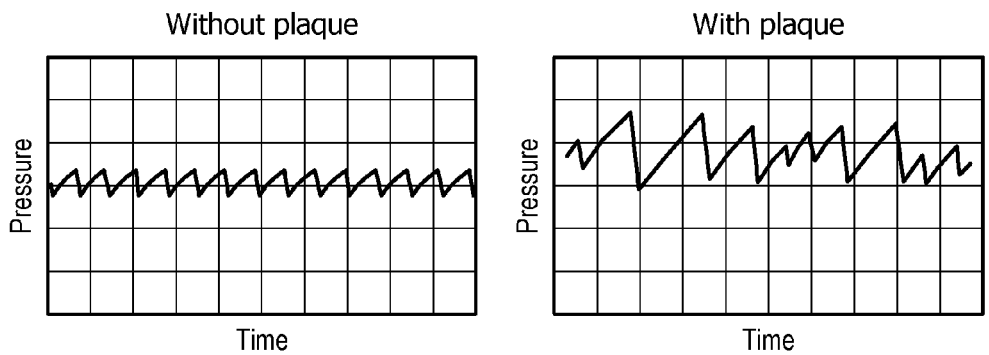
FIG. 8 illustrates on the left a sample pressure measurement versus time for the unblocked stream probe of FIG. 7 and on the right illustrates a sample pressure measurement versus time for the partially blocked stream probe of FIG. 7.

FIG. 8 illustrates pressure signals of a probe tip, e.g., a metal needle with a bevel, moving on enamel without plaque, as illustrated on the left, and on a sample with a plaque layer, as illustrated on the right. The increase in pressure seen in the right portion, attributed to obstruction of the needle opening by the plaque, can be sensed to detect if plaque is present.

Figure 9:
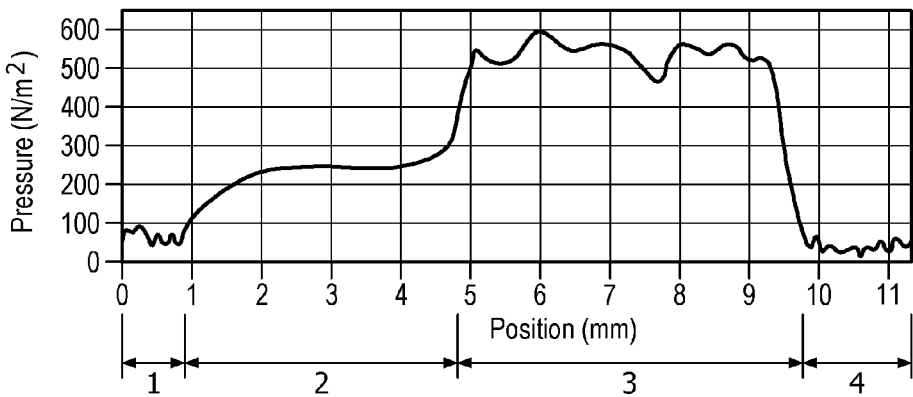
FIG. 9 illustrates a pressure signal versus time for a stream probe having a Teflon tip in accordance with one exemplary embodiment of the present disclosure.

FIG. 9 illustrates pressure signals of an airflow from a Teflon tip moving over water, region 1, PMMA (polymethyl methylacrylate) region 2, PMMA with plaque region 3, and water region 4. The tip moves (from left to right) over water region 1, PMMA region 2, PMMA with plaque region 3, and again over water region 4. The Teflon tip is not shown).

When reference is made to pressure differences herein, consideration of the following should be taken into account. In FIG. 8, the fluid stream 30 is obstructed when the pressure increases on the left panel. So the parameter of interest is the average pressure or average or momentary peak pressure.

In contrast, FIG. 9 illustrates identical signals for a smaller probe tip, in which case a much smoother signal is obtained.

The data presented in FIGS. 8 and 9 were taken without the inclusion of restriction orifices.

In preliminary experiments according to FIG. 2, we have observed the following:

Dental plaque (in wet state) is more hydrophilic than clean enamel, as shown in FIG. 3.

The release of air bubbles from the tip is measurable by pressure variations. A syringe with constant displacement velocity gives a sawtooth-like signal of pressure as a function of time. This is shown in the oscilloscope photograph in FIG. 5.

In case of close approach between tip and surface, the amplitude of the sawtooth signal is smaller when the probed surface is more hydrophilic than when the surface is less hydrophilic. So, smaller air bubbles are released on the more hydrophilic surface. This is also demonstrated by the measurements in FIG. 6, where the pressure signal amplitude as a function of distance d1 or d2 from the tip to the surface (see FIGS. 1 and 2) is given for different surfaces.

In preliminary experiments according to FIG. 7, we have observed the following:

An unblocked tip gives a regular release of air bubbles and a sawtooth-like pattern of pressure versus time, when a syringe is used with a constant displacement velocity. See the left panel of FIG. 8.

In an experiment with a metal tip moving through plaque material, an increase of pressure and an irregular sawtooth-like pattern of pressure versus time was observed, due to blocking of the tip by plaque material and opening of the tip by the air. See the right panel of FIG. 8.

In an experiment with a Teflon tip, clear signal differences were seen for different materials at the tip opening (from left to right: tip in water, tip above PMMA, above PMMA with plaque, and again tip in water).

These preliminary experiments indicate that the measurement of bubble release from a tip (by pressure and/or pressure variations and/or bubble size and/or bubble release rate) may become a suitable method to detect dental plaque at the tip. Accordingly, in view of the foregoing, at a minimum, the novel features of the exemplary embodiments of the present disclosure are characterized in that:

(a) fluid medium 14 is brought in contact with surface 13 at probe tip 12, generating interaction zone 17 between tip 12 and surface 13 (see FIG. 1); and (b) the shape and/or dynamics of the medium 14 in the interaction zone 17 depend on the properties of the surface 13 and/or on materials derived from the surface 13; and (c) the pressure and/or shape and/or dynamics of the medium 14 in the interaction zone 17 are detected.

In view of the foregoing description of the two differing methods of detecting the presence of a substance on a surface, the proximal pump portion 124 in FIGS. 4A and 4B effectively functions as a syringe. During injection of the plunger 126 or 126' distally, gas or air flow or liquid flow at the tip 112 in FIGS. 4A and 4B, or tip 112' in FIG. 7, can be pushed outwardly away from the tip (when the plunger is pushed).

During retraction or reverse travel of the plunger 126 or 126', gas or air flow or liquid flow can be suctioned inwardly at the tip 112 or 112' and in towards the probe tube 110 or 110'. In one exemplary embodiment, the plunger 126 or 126' is operated automatically together with the vibration of the bristles of an electric toothbrush or where the bristles are not vibrating (e.g. using the same principle in a dental floss device). Accordingly, the syringe or pump 124 can be used for the stream method in which flow of gas or air is injected away from the tip 112 and towards the enamel to generate bubbles 32 or 34. The bubbles and locations are detected optically and depending on whether the surface is more hydrophilic such as plaque or less hydrophilic such as enamel, the location of the bubble will determine whether there is plaque present. That is, the surface has a hydrophilicity which differs from the hydrophilicity of the substance to be detected, e.g., enamel has a hydrophilicity which is less than the hydrophilicity of plaque. The tip 112 is located at a particular distance d2 (see FIG. 2) away from the enamel regardless of whether plaque is present or not.

Alternatively, pressure sensing can also be used for the bubble method. Referring also to FIG. 2 and FIG. 4A, the same pump portion 124 functioning as a syringe can be used for the pressure sensing method as follows. Fluid is injected towards the enamel surface 31 or 33. The probe tip 112 is initially located at a particular dimension away from the enamel surface such as d2 in FIG. 2. The pressure signal is monitored as illustrated and described above in FIGS. 5 and 6. Bubble release measurements are performed by pressure and/or pressure variations as described above.

In the second method of detecting the presence of a substance on a surface according to the exemplary embodiments of the present disclosure, as illustrated in FIG. 7, the passage of the second fluid such as gas 30 through the distal tip 112 enables detection of substance 116 that may be present on the surface 31 based on measurement of a signal, correlating to a substance at least partially obstructing the passage of fluid through the open port of the distal tip 112'. The signal may include an increase or decrease in pressure or change in other variable as described above.

Since in one exemplary embodiment at least two probes 110' are utilized, FIG. 7 illustrates a system 300 for detecting the presence of a substance on a surface. In one exemplary embodiment, the probes 110' are in contact with the surface 31 or 33 as described above. If there is no plaque at the surface 33, i.e., flow is unblocked, then the pressure signal is as shown in FIG. 8, left panel. If there is plaque at the surface, e.g., viscoelastic material 116, then the pressure signal is as shown in FIG. 8, right panel.

For practical applications, it is contemplated that the probe or probes 110' have a very small diameter, e.g., less than 0.5 millimeters, such that by their spring function, the probe tips 112' will make contact with the tooth surface 33. So when reaching the plaque the tube is pressed into this layer of plaque. The pressure signals illustrated in FIG. 8 were obtained with a single probe in contact.

Referring again to FIG. 7, in an alternate exemplary embodiment of the second method of detecting the presence of a substance on a surface, fluid is suctioned away from the enamel surface by reverse travel of the plunger 126 or 126' proximally towards the proximal end 124' of the proximal pump portion 124' in FIGS. 4A and 4B. Fluid or gas inflow 30 now becomes fluid or gas outflow 35 as illustrated by the dotted arrows (shown outside of the interior channel 134 for simplicity). If there is plaque 116 present, the plaque either is large enough to block the aperture at the probe tip or is small enough to be suctioned inside the probe channel. The pressure signal becomes an inverted version of FIG. 8. Lower pressure will be obtained in the presence of plaque.

As defined herein, regardless of the direction of flow of the second fluid through the probe tip, obstruction can mean either a direct obstruction by a substance at least partially, including entirely, blocking the tip itself or obstruction can mean indirectly by the presence of a substance in the vicinity of the probe tip opening thereby perturbing the flow field of the second fluid.

In addition to performing the first and second methods by maintaining a constant velocity of the plunger, the methods may be performed by maintaining constant pressure in the proximal pump portion and measuring the variable outflow of the second fluid from the probe tip. The readout and control can be configured in different ways. For example, the apparatus may record the variable pressure and/or the variable flow of the second fluid. In one exemplary embodiment, the pressure is recorded and the flow of the second fluid is controlled, e.g., the flow is kept constant. In another exemplary embodiment, the flow is recorded and the pressure of the second fluid is controlled, e.g., the pressure is kept constant.

Additionally, when two or more probes 110' are deployed for system 300, one of the probes 110' may include pressure sensing of the flow of the second fluid through the distal probe tip 112' while another of the probes 110' may include strain sensing or flow sensing.

Additionally, for either the first method of bubble detection or the second method of obstruction, although the flow of the second fluid is generally laminar, turbulent flow of the second fluid is also within the scope of present disclosure.

Figure 10:
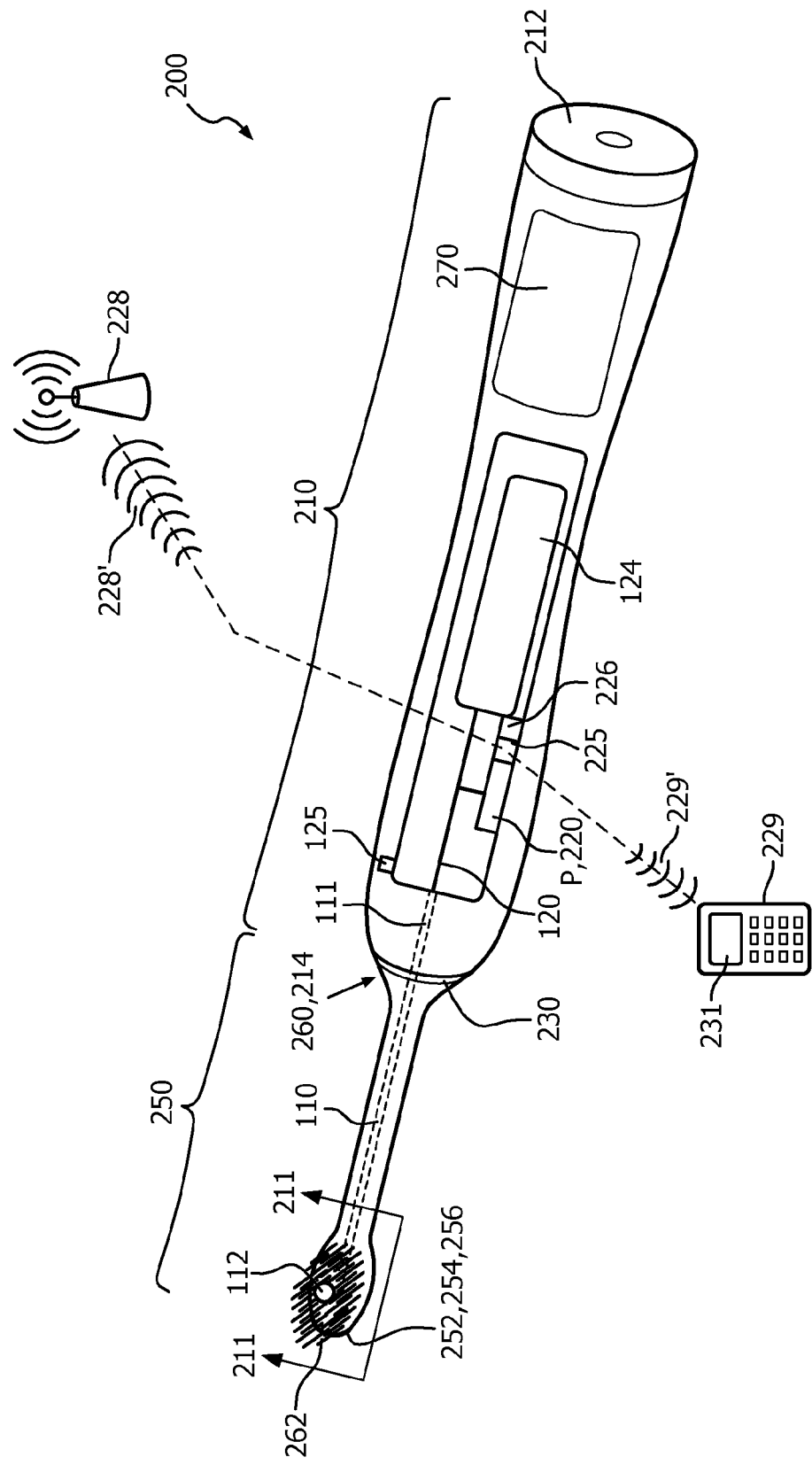
FIG. 10 illustrates a stream probe system incorporated into a dental apparatus such as an electric toothbrush in accordance with one exemplary embodiment of the present disclosure.

FIG. 10 illustrates a detection apparatus or instrument for detecting the presence of a substance on a surface according to one exemplary embodiment of the present disclosure wherein the detection apparatus is exemplified by the integration of the stream probe into a dental apparatus such as a tooth brush, forming thereby a detection apparatus for detecting the presence of a substance on a surface.

Traditionally an electric toothbrush system, such as the Philips Sonicare toothbrush mentioned above, comprises a body component and a brush component. Generally, the electronic components (motor, user interface UI, display, battery etc.) are housed in the body, whilst the brush component does not comprise electronic components. For this reason, the brush component is easily exchangeable and replaceable at a reasonable cost.

In one exemplary embodiment, detection apparatus or instrument 200, e.g., a dental cleaning instrument such as an electric toothbrush, is configured with a proximal body portion 210 and a distal oral insertion portion 250. The proximal body portion 210 defines a proximal end 212 and a distal end 214. The distal oral insertion portion 250 defines a proximal end 260 and a distal end 262. The distal end 262 includes a vibrating brush 252 with brush base 256 and bristles 254 and a distal portion of an air stream probe or a liquid stream probe such as air stream probe 100 described above with respect to FIG. 4A or 100' with respect to FIG. 4B. In conjunction with FIG. 4A, 4B or 4C, the detection apparatus 200 is configured such that active components, e.g., mechanical, electrical or electronic components, are incorporated within, or disposed externally on, the proximal body portion 210, whilst the passive components such as distal probe portion 110, are incorporated within, or disposed externally on, a distal portion, exemplified by, but not limited to, distal oral insertion portion 250. More particularly, probe tip 112 of probe 110 is incorporated close to or within the bristles 254 so as to intermingle with the bristles 254, while the central parameter sensing tubular portion 120 and the proximal tubular syringe portion 124 are incorporated within, or disposed externally on, proximal body portion 210. Thus, the distal probe portion 110 is at least partially in contact with the distal oral insertion portion 250. A portion 111 of the distal probe tip 110 is disposed on the proximal body portion 210 and thus is a proximal probe portion.

In one exemplary embodiment, the distal oral insertion portion 250, including the brush 252 that includes brush base 256 and bristles 254, is exchangeable or replaceable. That is, the proximal body portion 210 is removably attachable to the distal oral insertion portion 250.

Contact to the proximal body portion 210 with the active parts by the distal oral insertion portion 250 is provided by a mechanical connection 230 on the proximal body portion 210 that is disposed to interface the distal end 214 of proximal body portion 210 and proximal end 260 of distal oral insertion portion 250, thereby interfacing the portion 111 of the distal probe tip 110 with distal probe tip 110 disposed on the distal oral insertion portion 250 such that an air stream is generated and the pressure is sensed, such as at the location of parameter sensor P2 in FIG. 4B or parameter sensors P in FIG. 4A or 4C. Based on the pressure sensor signal, it is concluded if plaque is present at the area of the probe tip 112. Thus, the proximal body portion 210 is removably attachable to the distal probe portion, illustrated in FIG. 10 as the distal oral insertion portion 250. via the mechanical connection 230. Those skilled in the art will recognize that, although the detection apparatus or instrument 200 is illustrated in FIG. 10 such that the distal oral insertion portion 250 and the proximal body portion 210 are removably attachable from one another, and thus either one is replaceable, the detection apparatus or instrument 200 can be configured or formed as a unitary, integrated combined apparatus or instrument wherein the distal oral insertion portion 250 and the proximal body portion 210 are not readily detachable from one another.

In addition, the stream probes 100, 100' or 100" may be utilized independently without including the brush 252, the brush base 256, or the bristles 254, such as illustrated in FIGS. 4A, 4B and 4C. The detection apparatus or instrument 200 may be applied either with or without the brush 252, the brush base 256, or the bristles 254 both to dental and non-dental applications to detect the presence of a substance on a surface.

When the detection apparatus or instrument 200 is designed as a dental cleaning instrument, the probe 110 may be dimensioned and made from materials selected so as to yield a rotational stiffness that is generally equivalent to the rotational stiffness of the bristles 254 such that the probe 110 sweeps an area during operation generally equivalent to the sweep area and timing of the bristle operation so as to reduce any potential discomfort to the user. The variables contributing to the design of the stiffness include the dimensions, the mass and the modulus of elasticity of the material selected.

In one exemplary embodiment, the active components comprise the pressure sensor P as described above. In conjunction with FIG. 1, the sensor P is used to sense the shape and/or dynamics of the medium 14 in the interaction zone 17. Such a sensor has the advantage that it is robust and simple to use. The sensor P is in electrical communication with detection electronics 220 that include a controller 225 that is in electrical communication therewith.

In an alternate exemplary embodiment, the active component may comprise an optical, electrical or acoustic sensor such as, for example, a microphone, in order to sense the shape and/or dynamics of the medium 14 in the interaction zone 17.

The controller 225 can be a processor, microcontroller, a system on chip (SOC), field programmable gate array (FPGA), etc. Collectively the one or more components, which can include a processor, microcontroller, SOC, and/or FPGA, for performing the various functions and operations described herein are part of a controller, as recited, for example, in the claims. The controller 225 can be provided as a single integrated circuit (IC) chip which can be mounted on a single printed circuit board (PCB). Alternatively, the various circuit components of the controller, including, for example, the processor, microcontroller, etc. are provided as one or more integrated circuit chips. That is, the various circuit components are located on one or more integrated circuit chips.

Furthermore, the active components enable a method of generating an air or liquid stream. A combined air with liquid stream is possible as well. The method may comprise an electrical or a mechanical pumping method, whereby the mechanical method may comprise a spring component which is mechanically activated, e.g., wherein plunger 126 in FIG. 4 is mechanically activated. In one exemplary embodiment, the method of generating the air stream is an electrical pumping principle, as this combines well with the pressure sensing component described above. In other exemplary embodiments, air may be replaced by other gases, e.g., nitrogen or carbon dioxide. In such exemplary embodiments, while the proximal body portion 210 may include the proximal pump portion 124 and the plunger 126 or other types of pumps to generate either constant pressure or constant flow of fluid, the proximal body portion 210 may include a container of compressed gas (not shown) that is sized to fit within the proximal body portion 210 and is capable of providing either constant pressure or constant flow via a valve control system (not shown).

In yet another exemplary embodiment, the passive components comprise only a tube with an opening at the end, such as probe 110 and distal tip 112 (see FIG. 10).

In still another exemplary embodiment, connection of the active and passive components is realized by a mechanical coupling 230 of the tube to the output of the pressure sensor. Such a coupling is ideally substantially pressure sealed. Pressure values are relatively low (<<1 bar).

In operation, the sensing is carried out in a repetitive manner during the tooth brushing process. In a preferred exemplary embodiment, sensing is carried out at a frequency >1 Hz, more preferably >5 Hz and even more preferably >10 Hz. Such a high frequency embodiment facilitates the dynamic and real time measurement of plaque removal as the toothbrush is moved from tooth to tooth, as several measurements may be made on an individual tooth (the dwell time on a given tooth is typically of the order of 1-2 seconds).

In conjunction with FIG. 1, as described above, the shape and/or dynamics of the medium 14 in the interaction zone 17 depend on the properties of the surface 13 and/or on materials derived from the surface 13, the pressure and/or shape and/or dynamics of the medium 14 in the interaction zone 17 are detected and a determination is made by the controller 225 as to whether a level of plaque exceeding a predetermined maximum permissible level of plaque is detected at the particular dental surface 13.

If a positive detection is made, no progression or advancement signal is transmitted to the user of the electric toothbrush until a predetermined maximum permissible plaque level is achieved at the particular dental surface 13 by continued cleaning at the dental surface 13 of that particular tooth.

Upon reduction of the level of plaque to at or below the maximum permissible plaque level, i.e., a negative detection is made, a progression signal or advancement signal is transmitted to the user to inform the user that it is acceptable to progress to an adjacent tooth or other teeth by moving the vibrating brush and probe tip of the dental apparatus.

Alternatively, if a positive detection is made, a signal is transmitted to the user of the electric toothbrush having an integrated stream probe plaque detection system to continue brushing the particular tooth.

Furthermore, there are several preferred modes of operation of the passive component in the brush.

In a first mode operation, the tube is configured such that the tip of the tube is acoustically uncoupled from the vibration of the brush (which vibrates at about 265 Hz in a Philips Sonicare toothbrush). This may be achieved by only weakly coupling the tube to the brush head.

In a further mode of operation, the tube is configured such that the tip of the tube is static. This may be achieved by choosing the mechanical properties of the tube (stiffness, mass, length) such that the tip of the probe is at a static node of vibration at the driving frequency. Such a situation may be helped by adding additional weight to the end of the tube close to the opening.

Figure 11:
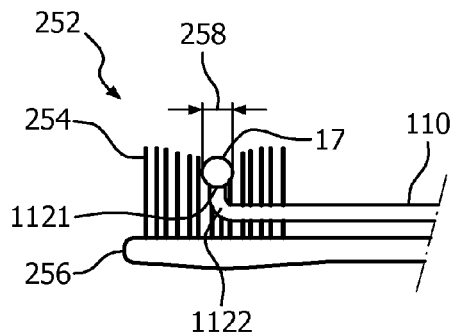
FIG. 11 illustrates a view of the brush of the dental apparatus taken along line 211-211 of FIG. 10 having a stream probe tip at a position within the bristles of the brush.

As illustrated in FIG. 11, which is a partial cross-sectional view of distal oral insertion portion 250 in FIG. 10, in a further exemplary embodiment, the effect of the motion of bristles of the toothbrush on the sensing function is reduced by incorporating a spacing 258 around the tube where the bristles are removed. More particularly, probe 110 in FIG. 11 illustrates a brush head 252 that includes base 256 and bristles 254 that protrude generally orthogonally from the base 256. Spacing 258 is positioned with removed bristle wires around probe tip 1121. The probe tip 1121 differs from probe tips 112 and 112' in that probe tip 1121 includes a 90 degree elbow 1122 so as to enable fluid flow through the probe 110 towards the surface 31 or 33.

In one exemplary embodiment, the spacing 258 should be of the order of the amplitude of the vibration of the bristles 254. In practice, the bristles vibrate with an amplitude of around 1-2 mm. This makes the sensing more robust.

Figure 12:
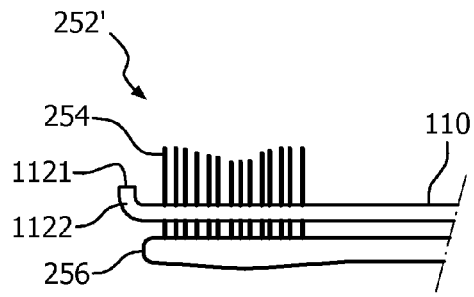
FIG. 12 illustrates an alternate exemplary embodiment of the view of the brush of FIG. 11 wherein the stream probe tip extends distally from the bristles of the brush.

In a further exemplary embodiment, as illustrated in FIG. 12, the probe tip 1121 is situated distally beyond the area covered by the bristles 254. This makes it possible to detect plaque which is present beyond the present position of the brush, for example plaque which has been missed by an incomplete brushing action.

As a further detail, ideally the angle of the brush 252 while brushing is 45 degrees with respect to the tooth surface 31 or 33. Ideally the angle of the probe tip 1121 is close to 0 degrees with respect to the tooth surface 31 or 33. At least two probes 110 and correspondingly at least two pressure sensors and two pumps with a tip end 1121 of 45 degrees with respect to the tooth surface 31 or 33, so that always one probe is interfacing optimally the surface 31 or 33.

In still a further exemplary embodiment, a plurality of probes are incorporated in the brush. These probes may alternatively be disposed or utilized at least as follows:

(a) positioned at multiple positions around the brush, to sense for (missed) plaque more effectively, or (b) used for differential measurements to determine the degree and effectiveness of the plaque removal.

In one exemplary embodiment, the plurality of probes may be realized with a single active sensing component and a multiplicity of passive components, such as tubes, attached to a single pressure sensor. Alternatively, a plurality of active and passive sensing components may be used.

The end of the tube may have many dimensions, as described above. In alternative exemplary embodiments, the tip of the tube will be spaced from the surface of the tooth using a mechanical spacer. In some exemplary embodiments, the opening may be made at an angle to the tube.

FIGS. 13-22 illustrate examples of a detection system 3000 for detecting the presence of a substance on a surface that employs the foregoing principles for detecting the presence of a substance on a surface via multiple stream probes. More particularly, in one exemplary embodiment of the present disclosure, the system 3000 includes a detection apparatus 1100 for detecting the presence of a substance on a surface such as an air stream probe having proximal pump portion 124 and plunger 126 as described above with respect to FIG. 4A and FIG. 10. It should be noted, however, that in lieu of proximal pump portion 124 and plunger 126, proximal pump portion 142 and diaphragm pump 150, as described above with respect to FIG. 4C, may also be deployed to provide a generally continuous flow 1100 for detecting the presence of a substance on a surface in a similar manner as described below with respect to the proximal pump portion 124 and plunger 126.

The proximal pump portion 124 includes a central parameter sensing tubular portion 120' configured with a distal tee connection 101 defining a first leg 1011 and a second leg 1012. First stream probe 301 having a distal probe tip 3112 is fluidically coupled to the first leg 1011 and second stream probe 302 having a distal probe tip 3122 is fluidically coupled to the second leg 1012.

A pressure sensor P3 is connected to the first leg 1011 via branch connection 312 in the vicinity of the first stream probe 301 and a pressure sensor P4 is connected via branch connection 322 in the vicinity of second stream probe 302 to the second leg 1012. In as similar manner as with respect to stream probe 100 described above with respect to FIG. 4A, stream probe 100' described above with respect to FIG. 4B and stream probe 100" described above with respect to FIG. 4C, the stream probe 1100 may include a restriction orifice 3114 disposed in first leg 1011 downstream of junction 314 between central parameter sensing tubular portion 120' and the first leg 1011 and upstream of first stream probe 301 and pressure sensor P3. Similarly, a restriction orifice 3124 may be disposed in second leg 1012 downstream of junction 324 between central parameter sensing tubular portion 120' and the second leg 1012 and upstream of second stream probe 302 and pressure sensor P4. Again, the presence of the restriction orifices 3114 and 3124 improves the response time of the pressure meters P3 and P4 since only the volume of the stream probe 1100 downstream of the restriction orifices 3114 and 3124 is relevant. The air flow into each pressure sensor P3 and P4 becomes approximately independent since the pressure drops occur predominantly across the restriction orifices 3114 and 3124 and the stream probe 1100 behaves more closely or approximately as a flow source rather than a pressure source. The volume upstream of the restriction orifice 240 becomes less relevant. The pressure sensors P3 and P4 can each generally sense a pressure rise separately while being driven by single plunger 126.

Additionally, those skilled in the art will recognize that the restriction of flow via orifices 3114 and 3124 may be effected by crimping the distal tee connection 101 in the vicinity of the junctions 314 and 324 in lieu of installing a restriction orifice. Again, as defined herein, a restriction orifice includes a crimped section of tubing.

In a similar manner as described above with respect to detection apparatus 200 illustrated in FIG. 10, the sensors P3 and P4 are in electrical communication with detection electronics and a controller such as detection electronics 220 that include controller 225 that is in electrical communication therewith (see FIG. 10).

Upon detection of plaque by the detection electronics 220, the controller 225 generates a signal or an action step. Referring to FIG. 10, in one exemplary embodiment, the controller 225 is in electrical communication with an audible or visible alarm 226 located on the such as a constant or an intermittent sound such as a buzzer and/or a constant or intermittent light that is intended to communicate to the user to continue brushing his or her teeth or the subject's teeth at that particular location.

In one exemplary embodiment, based upon the signals detected by the detector electronics 220, the controller 225 may record data to generate an estimate of the quantity of plaque that is present on the teeth. The data may be in the form of a numerical quantity appearing on a screen 125 in electrical communication with the detector electronics 220 and the controller 225. The screen 125 may be located on, or extending from, the proximal body portion 210 as illustrated in FIG. 10. Those skilled in the art will recognize that the screen 125 may be located at other positions suitable for the user to monitor the data presented on the screen.

The signalling to the user may include the controller 225 configured additionally as a transceiver to transmit and receive a wireless signal 228' to and from a base station 228 with various indicators on the base station that generate the signal to trigger the audible or visual alarm 226 or to record the numerical quantity or other display message such as an animation on the screen 125.

Alternatively, the controller 225 may be configured additionally as a transceiver to transmit and receive a wireless signal 229' to a smart phone 229 that runs application software to generate animations on a screen 231 that signal that plaque has been identified and instruct the user to continue brushing in that location. Alternatively, the application software may present quantitative data on the amount of plaque detected.

Figure 16:
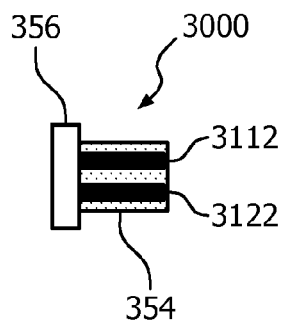
FIG. 16 illustrates still another view of the brush of FIG. 14.
Figure 14:
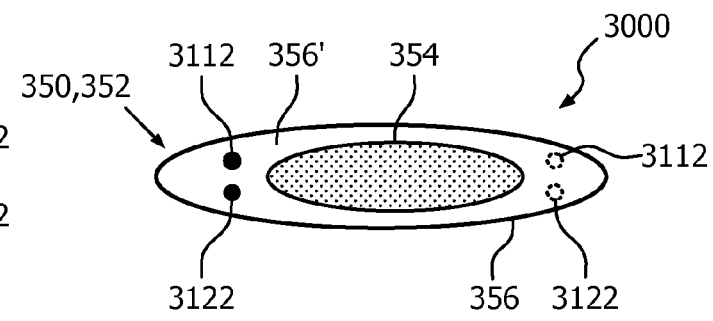
FIG. 14 illustrates an alternate exemplary embodiment of the brush of FIG. 10 that includes multiple stream probes on the brush that includes the base of the brush such as according to the embodiment of a stream probe according to FIG. 13.
Figure 15:
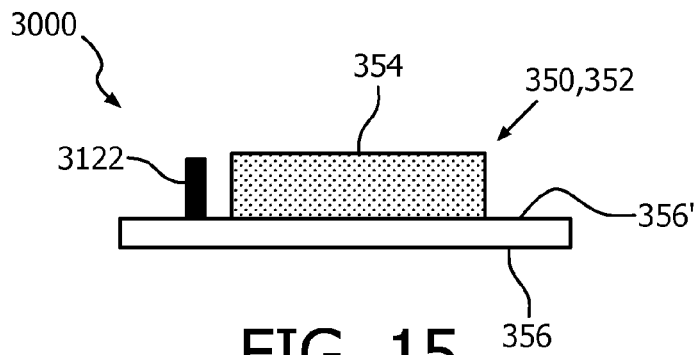
FIG. 15 illustrates another view of the brush of FIG. 14.

FIGS. 14-16 illustrate an alternate distal oral insertion portion 350 that includes a brush 352 with bristles 354 mounted on brush base 356, and as illustrated in FIG. 14 as viewed looking towards the brush base 356 and the upper tips of the bristles 354. As best illustrated in FIGS. 15 and 16, extending generally orthogonally from horizontal upper surface 356' of brush base 356 are distal probe tips 3112 and 3122 which enable multiple fluid flows to be directed towards the surface of interest such as surfaces 31 and 33 in FIGS. 2 and 7. Alternate or additional positions for distal probe tips 3112 and 3122 are illustrated by the dotted lines in the vicinity of the proximal end of the brush base 356 in FIG. 14.

Figure 19:
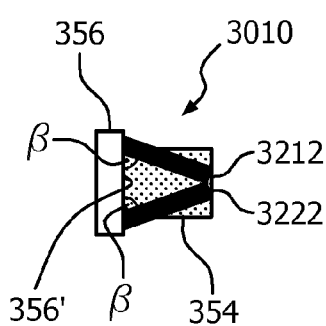
FIG. 19 illustrates still another view of the brush of FIG. 17.
Figure 17:
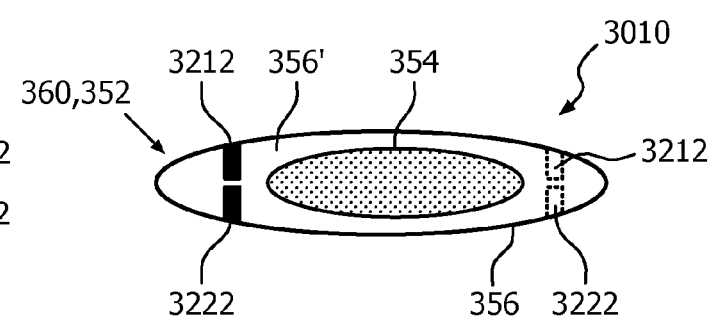
FIG. 17 illustrates another alternate exemplary embodiment of the brush of FIG. 10 that includes multiple stream probes on the brush that includes the base of the brush.
Figure 18:
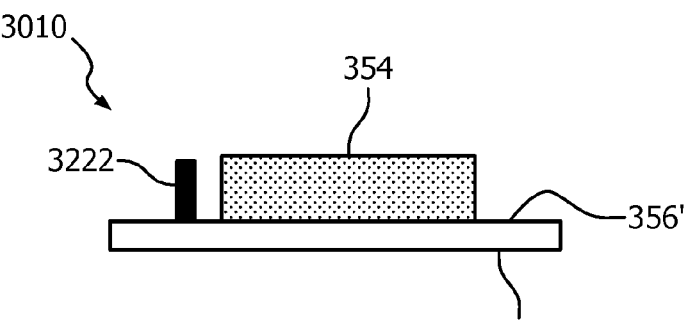
FIG. 18 illustrates another view of the brush of FIG. 17.

In a similar manner, FIGS. 17-19 illustrate system 3010 for detecting the presence of a substance on a surface that differs from system 3000 in that system 3010 includes another alternate distal oral insertion portion 360 that includes the brush 352 with 352 with bristles 354 mounted on brush base 356, and as illustrated in FIG. 17 as viewed looking towards the brush base 356 and the upper tips of the bristles 354. As best illustrated in FIG. 19, each extending at an angle β with respect to the horizontal upper surface 356' of brush base 356 are distal probe tips 3212 and 3222 which enable multiple fluid flows to be directed at angle β towards the surface of interest such as surfaces 31 and 33 in FIGS. 2 and 7. In a similar manner, alternate or additional positions for distal probe tips 3212 and 3222 are illustrated by the dotted lines in the vicinity of the proximal end of the brush base 356 in FIG. 17.

The distal oral insertion portions 350 and 360 illustrated in FIGS. 14-16 and FIGS. 17-19 may be utilized for either: (a) the first method of detecting the presence of a substance on a surface which includes the measurement of bubble release from a tip (by pressure and/or pressure variations and/or bubble size and/or bubble release rate), or (b) for the second method of detecting the presence of a substance on a surface which includes the passage of the second fluid such as a gas or a liquid through the distal tip based on measurement of a signal, correlating to a substance obstructing the passage of fluid through the open port of the distal tip.

Figure 20:
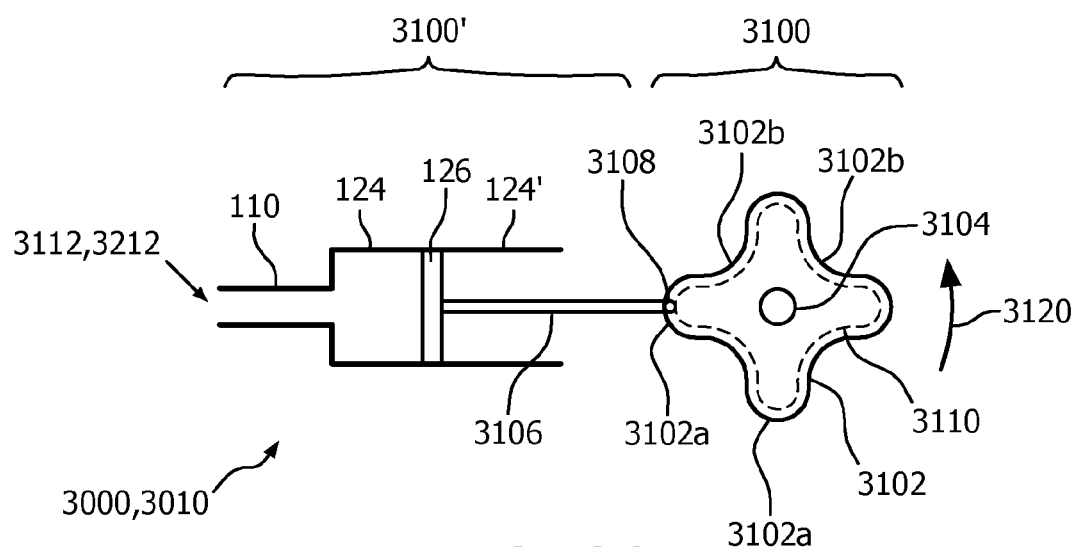
FIG. 20 illustrates one exemplary embodiment of the present disclosure of a system for detecting the presence of a substance on a surface wherein a stream probe operating apparatus includes a first stream probe.
Figure 21:
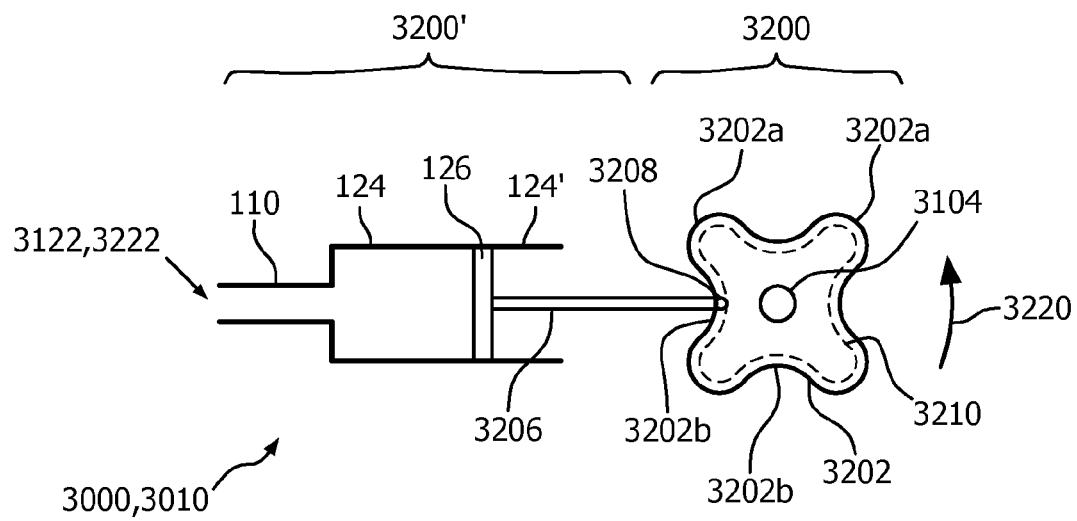
FIG. 21 illustrates the system of FIG. 20 wherein another stream probe operating apparatus includes a second stream probe.
Figure 22:
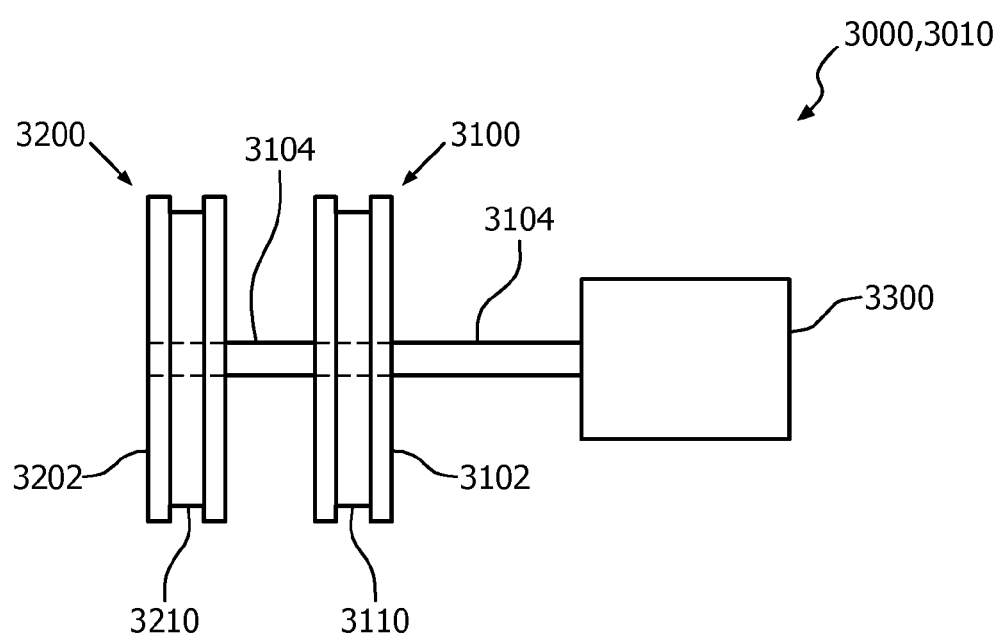
FIG. 22 illustrates the system of FIGS. 20 and 21 wherein a motor is operably connected to a common shaft that operates the stream probe operating apparatuses of FIGS. 20 and 21.

FIGS. 20-22 illustrate exemplary embodiments of the system 3000 or system 3010 that includes multiple stream probes and corresponding proximal pump portions that may be operated by a common rotating shaft and motor. More particularly, FIG. 20 illustrates a first stream probe operating apparatus 3100 that includes first stream probe 3100'. First stream probe 3100' is identical to the stream probe 100' described above with respect to FIG. 4B and may include the proximal pump portion 124 and plunger 126 and either the distal probe tip 3112 (see FIGS. 14-16) or the distal probe tip 3212 (see FIGS. 17-19). A rotary to linear motion operating member 3102, which may be a cam mechanism as illustrated, is in operable communication with the plunger 126 via a reciprocating shaft 3106 and a roller mechanism 3108 disposed on the proximal end of the shaft 3106.

The roller mechanism 3108 engages in a channel 3110 defining a path on the periphery of the cam mechanism 3102. The channel 3110 extends along the path to include cam peaks 3102a and cam troughs 3102b. The cam mechanism 3102 is mounted on and rotated by a common shaft 3104, in a direction such as the counterclockwise direction illustrated by arrow 3120. As the cam mechanism 3102 rotates, a reciprocating linear motion is imparted to the shaft 3106 as the roller mechanism 3108 is intermittently pushed by the peaks 3102a or pulled into the troughs 3102b. Thereby, a reciprocating linear motion is imparted to the plunger 126, pressure is generated in the stream probe 3100', and fluid flow passes through the distal tips 3112 or 3212. Those skilled in the art will understand that the path defined by the channel 3110 may be designed to impart a generally constant velocity to the plunger 126. Alternatively, the path defined by the channel 3110 may be designed to impart a generally constant pressure in the proximal pump portion 124. The plunger 126 is at a position distally away from the proximal end 124' of the proximal plunger portion 124 since the roller mechanism 3108 is at a peak 3102a.

FIG. 21 illustrates a second stream probe operating apparatus 3200 that includes second stream probe 3200'. Second stream probe 3200' is also identical to the stream probe 100' described above with respect to FIG. 4B and may include the proximal pump portion 124 and plunger 126 and either the distal probe tip 3122 (see FIGS. 14-16) or the distal probe tip 3222 (see FIGS. 17-19). Again, a rotary to linear motion operating member 3202, which may be a cam mechanism as illustrated, is in operable communication with the plunger 126 via a reciprocating shaft 3206 and a roller mechanism 3208 disposed on the proximal end of the shaft 3206.

Similarly, the roller mechanism 3208 engages in a channel 3210 defining a path on the periphery of the cam mechanism 3202. The channel 3210 extends along the path to include cam peaks 3202a and cam troughs 3202b. The cam mechanism 3202 is mounted on and rotated by a common shaft 3204, in a direction such as the counterclockwise direction illustrated by arrow 3220. As the cam mechanism 3202 rotates, a reciprocating linear motion is imparted to the shaft 3206 as the roller mechanism 3208 is intermittently pushed by the peaks 3202a or pulled into the troughs 3202b. Thereby, a reciprocating linear motion is also imparted to the plunger 126, pressure is generated in the stream probe 3200', and fluid flow passes through the distal tips 3122 or 3222. Again, those skilled in the art will understand that the path defined by the channel 3210 may be designed to impart a generally constant velocity to the plunger 126. Again, alternatively, the path defined by the channel 3110 may be designed to impart a generally constant pressure in the proximal pump portion 124. In contrast to first stream probe operating apparatus 3100, the plunger 126 is at a position at the proximal end 124' of the proximal plunger portion 124 since the roller mechanism 3208 is now at a trough 3202b.

FIG. 22 illustrates a motor 3300 that is operably connected to the common shaft 3104 such that the first rotary to linear motion operating member 3102 of stream probe operating apparatus 3100 is mounted proximally on the common shaft 3104 with respect to the motor 3300 while the second rotary to linear motion operating member 3202 of stream probe operating apparatus 3200 is mounted distally on the common shaft 3104 with respect to the motor 3300. Those skilled in the art will recognize that rotation of the common shaft 3104 by the motor 3300 causes the multiple stream probe operation as described above with respect to FIGS. 20 and 21. The motor 3300 is supplied electrical power by a power supply 270 mounted on proximal body portion 210 (see FIG. 10) such as a battery or ultracapacitor or alternatively a connection to an external power source or other suitable means (not shown).

Those skilled in the art will recognize that either stream probe operating apparatus 3100 or stream probe operating apparatus 3200 may operate the single air stream probe 1100 with multiple distal probe tips 3112 and 3122 described above with respect to FIG. 13 or the multiple distal probe tips 3212 and 3222 described above with respect to FIGS. 17-19.

Those skilled in the art will recognize that the stream operating apparatuses 3100 and 3200 described with respect to FIGS. 20-22 are merely examples of apparatuses which may be employed to effect the desired operation. For example, those skilled in the art will recognize that stream probe 100" and its associated components may replace the plunger 126 and either rotary to linear motion operating member 3102 or rotary to linear motion operating member 3202 or both and motor 3300 may be replaced by the diaphragm pump 150 that includes flexible or compressible diaphragm 158 as described above with respect to FIG. 4C.

The motor 3300 is in electrical communication with the controller 225 which controls the motor operation based on the signals received by the detector electronics 220. In addition to the alarm 226, the screen 125, the base station 228 and the smart phone 229 described above with respect to FIG. 10, in conjunction with FIG. 10, signaling to the user that plaque has been detected may include the controller 225 programmed to change the toothbrush drive mode by varying the operation of the motor 3300 to increase the brushing intensity either in frequency or in amplitude, or both, when plaque is detected. The increase in amplitude and/or frequency both signal to the user to continue brushing in that area, and thus improves effectiveness of plaque removal. Alternatively, the controller 225 may be programmed to create a distinct sensation in the mouth that the user can distinguish from regular brushing, for example, by modulating the drive train to signal that plaque has been located.

The supply of air bubbles to a tooth brush may also improve the plaque removal rate of the brushing.

One possible mechanism is that (i) air bubbles will stick to spots of clean enamel, (ii) brushing brings a bubble into motion, and thereby also the air/water interface of the bubble, and (iii) when the bubble edge contacts plaque material, the edge will tend to peel the plaque material off the enamel, because the plaque material is very hydrophilic and therefore prefers to stay in the aqueous solution. Another possible mechanism is that the presence of bubbles can improve local mixing and shear forces in the fluid, thereby increasing the plaque removal rate. It should be noted that other exemplary embodiments of the methods of detection of a substance on a surface as described herein may include monitoring the first derivative of the signals, AC (alternating current) modulation, and utilization of a sensor for gum detection.

To enhance the effectiveness of the method to reduce the occurrence of false positive signals when either of the stream probe tubular members 110' (see FIG. 7) are positioned on the gums, it is beneficial to distinguish between gums and plaque. The relatively soft gums also results in (partial) blocking of the stream. This blocking results in false positive signals. The user may think that plaque is present, while actually the sensor position is on the gum.

Figure 23:
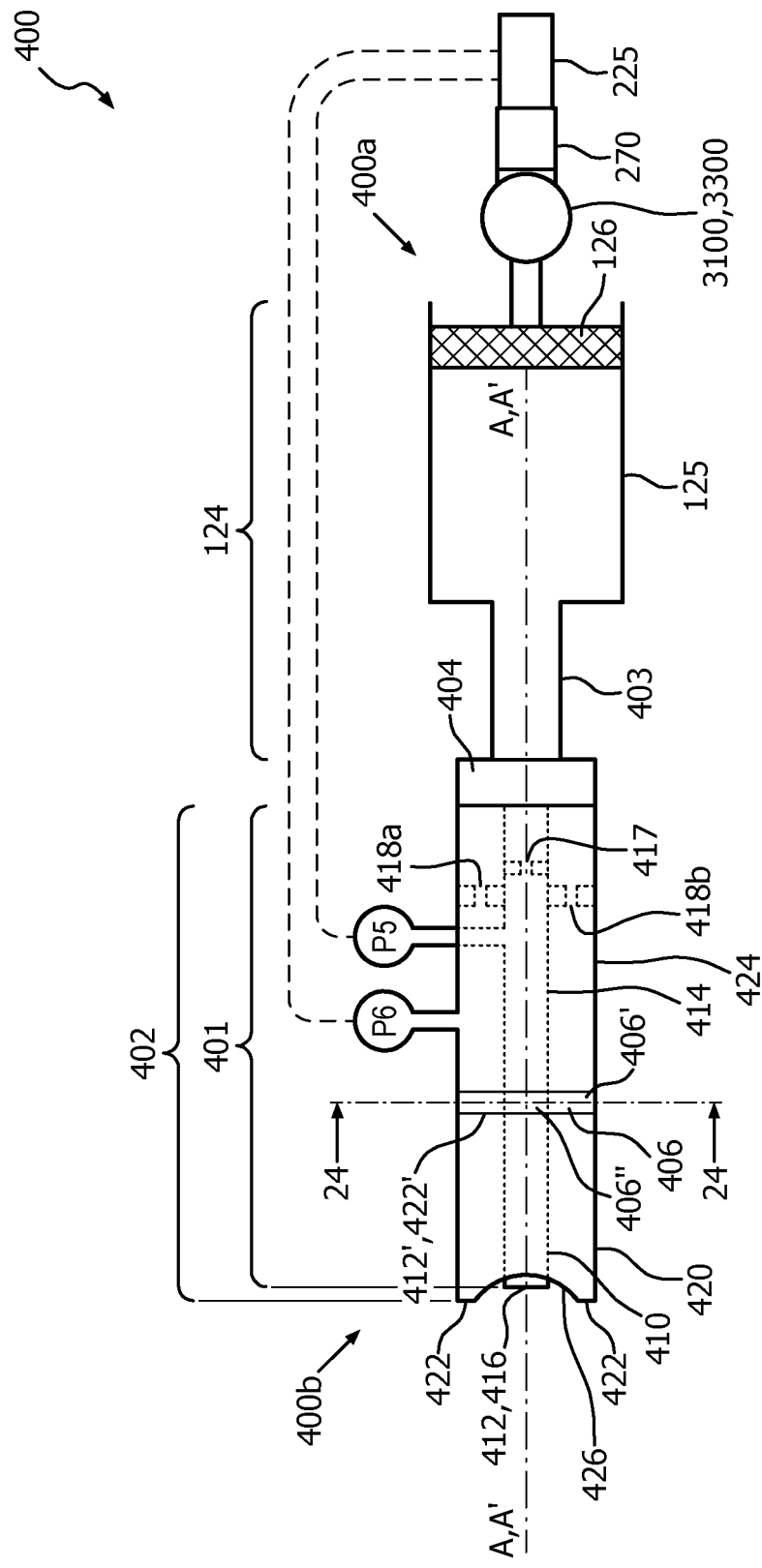
FIG. 23 illustrates a detection apparatus that includes a first stream probe to detect plaque and a second stream probe to detect the gum of a subject or of a user of the apparatus according to one exemplary embodiment of the present disclosure.
Figure 24:
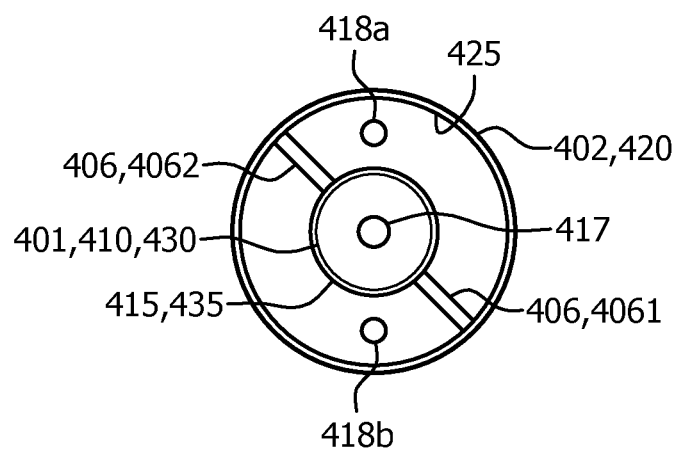
FIG. 24 is a cross-sectional view taken along section 24-24 of FIG. 23 showing the cross-section of the first stream probe and of the second stream probe wherein the second stream probe is arranged concentrically around the first stream probe.
Figure 25:
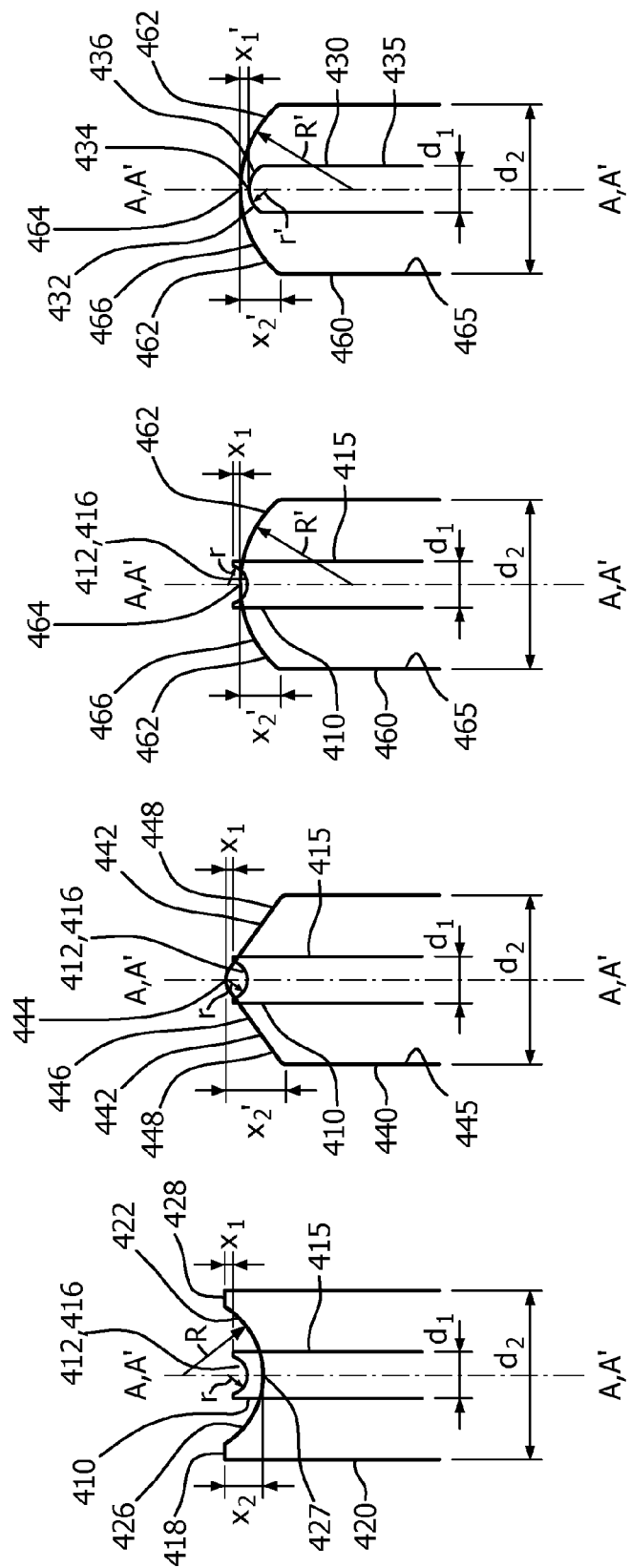
FIG. 25A is a partial side view of distal tips of distal probe portions of the first stream probe and the second stream probe of FIG. 23 wherein the distal tips both have a concave profile.
FIG. 25B is a partial side view of an alternate exemplary embodiment of distal tips of distal probe portions of the first stream probe and the second stream probe of FIGS. 23 and 25A wherein the distal tip of the distal probe portion of the first stream has a concave profile and the distal tip of the distal probe portion of the second stream has a convex profile.
FIG. 25C is a partial side view of an alternate exemplary embodiment of distal tips of distal probe portions of the first stream probe and the second stream probe of FIG. 25B wherein the distal tip of the distal probe portion of the first stream has a concave profile and the distal tip of the distal probe portion of the second stream has a convex profile.
FIG. 25D is a partial side view of an alternate exemplary embodiment of distal tips of distal probe portions of the first stream probe and the second stream probe of FIGS. 23, 25A, 25B and 25C wherein the distal tips both have a convex profile.
Figure 26:
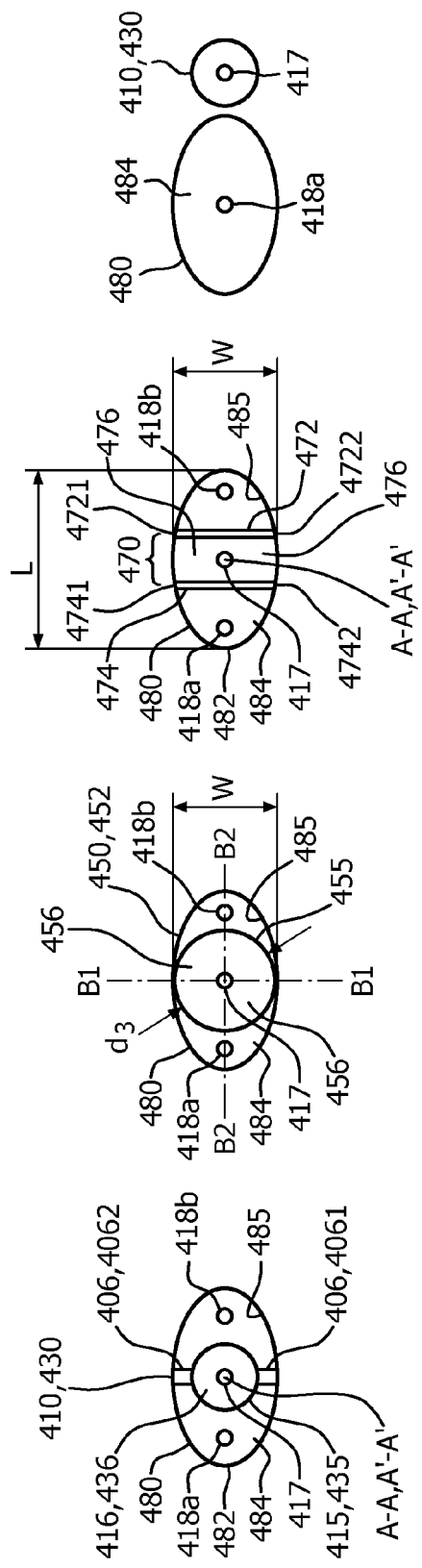
FIG. 26A is a cross-sectional view an alternate exemplary embodiment of the distal probe portions of FIG. 24 wherein the second stream probe defines an arcuate, non-circular cross section in a direction transverse to its longitudinal axis and wherein the distal probe portion of the first stream probe defines a circular cross section in a direction transverse to its longitudinal axis.
FIG. 26B is a cross-sectional view an alternate exemplary embodiment of the distal probe portions of FIG. 26A wherein the distal probe portion of the first stream tube has a diameter such that the outer surface of the distal probe portion of the first stream probe contacts the inner surface of the distal probe portion of the second stream probe.
FIG. 26C illustrates still another alternate exemplary embodiment of the distal probe portion of the first stream probe of FIGS. 26A and 26B wherein the distal probe portion of the first stream probe is formed by a pair of parallel plates wherein lateral edges of the parallel plates are in contact with the inner surface of the distal probe portion of the second stream probe.

Consequently, turning now to FIGS. 23-29, according to one embodiment of the present disclosure, there is illustrated in FIGS. 23, 24 and 25A a detection apparatus 400 such as a toothbrush with plaque detection features wherein the detection apparatus 400 contains a first stream probe 401 to detect the plaque and a second stream probe 402 to detect only gums. By comparing both signals, the detection apparatus 400 is able to distinguish between gums versus plaque. In an alternate embodiment, the first stream probe 401 may also detect the gums of a subject or of a user of the detection apparatus 400. As defined herein, a subject is a person, including a child or an infirm person, to whom, or an animal to which, the detection apparatus 400 is applied by a user of the detection apparatus 400. The user may include a dental or medical professional. Alternatively, the detection apparatus 400 may be self-applied by a user of the detection apparatus 400.

The first stream probe 401 is configured with a distal probe portion 410 that is configured to be immersed in first fluid 11. The distal probe portion 410 of the first stream probe 401 defines a distal tip 412 having an open port 416 to enable the passage of second fluid 30 through the open port 416. The distal tip 412 has a shape and size configured for a user of the detection apparatus 400 to detect a substance, e.g., substance 116 in FIG. 7, that may be present on a surface, e.g., surface 31 or 33 in FIG. 7, where the substance 116 may be dental plaque.

The second stream probe 402 is also configured with a distal probe portion 420 that is also configured to be immersed in the first fluid 11. The distal probe portion 420 of the second stream probe 402 defines a distal tip 422 having an open port 426 to enable the passage of the second fluid 30 through, the open port 426. The distal tip 422 has a shape and size configured for a user of the detection apparatus 400 to detect placement of the distal tip 422 on the gums of a subject, which may be the user of the detection apparatus 400.

The detection apparatus 400 is also configured such that passage of the second fluid (30) through the distal tip 412 of the distal probe portion 410 of the first stream probe 401 and passage of the second fluid 30 through the distal tip 422 of the distal probe portion 420 of the second stream probe 402 enables detection of a substance 116 that may be present on the surface 31, 33 based on measurement of a signal. The signal correlates to a substance 116 at least partially obstructing the passage of fluid 30 through the open port 416 of the distal tip 412 of the distal probe portion 410 of the first stream probe 401 and confirmation that the substance 116 is not the gums of the subject or of the user of the detection apparatus 400 and not the generation of a false alarm signal that the substance is the gums of the subject or the user of the detection apparatus 400. The confirmation is effected by comparison between the measurement of a signal correlating to a substance 116 at least partially obstructing the passage of fluid 30 through the open port 416 of the distal tip 412 of the distal probe portion 410 of the first stream probe 401 and measurement of a signal correlating to an object not obstructing the passage of fluid 30 through the open port 426 of the distal tip 422 of the distal probe portion 420 of the second stream probe 402.

Referring also to FIG. 10, the detection apparatus 400 further includes the proximal body portion 210 that includes pump portion 124 with a cylinder 125 and plunger 126 reciprocatingly movable within the cylinder 125. The cylinder 125 is in fluid communication with a fluid conduit member 403 and a plenum 404. The plenum 404, in turn, is in fluid communication with a proximal probe portion 414 of the first stream probe 410 that is coupled to distal probe portion 410 via a coupler or connector 406', thereby providing fluid communication between the cylinder 125, fluid conduit member 403, plenum 404, and the proximal probe portion 414 and distal probe portion 410 of the first stream probe 410.

Similarly, the plenum 404, in turn, is in fluid communication with a proximal probe portion 424 of the second stream probe 420 that is coupled to distal probe portion 420 via a second coupler or connector 406", thereby also providing fluid communication between the cylinder 125, fluid conduit member 403, plenum 404, and the proximal probe portion 424 and distal probe portion 420 of the second stream probe 420. Those skilled in the art will recognize that, and understand that, the couplers or connectors 406' and 406" may be either separate members from one another or formed integrally as a common coupler or connector 406 having joining posts 4061 and 4062 illustrated in the cross-sectional view of FIG. 24.

Again, those skilled in the art will recognize that the detection apparatus 400 is merely an example of a detection apparatus which may be employed to effect the desired operation. For example, those skilled in the art will recognize again that stream probe 100" and its associated components including the diaphragm pump 150 that includes flexible or compressible diaphragm 158 as described above with respect to FIG. 4C may replace the plunger 126, cylinder 125, the pump portion 124, etc.

FIG. 24 is a cross-sectional view of the detection apparatus 400 taken along section line 24-24 of FIG. 23 at the coupler or connector 406 or separate couplers or connectors 406' and 406" as viewed towards proximal end 400a of the detection apparatus 400, wherein distal end 400b of the detection apparatus 400 is defined with respect to the proximal end 400a.

As may also be appreciated by those skilled in the art, in one exemplary embodiment, the detection apparatus 400 may also be configured wherein the distal probe portion 410 of first stream probe 401 is integrally joined with the proximal probe portion 414 of the first stream probe 401, and wherein the distal probe portion 420 of the second stream probe 402 is integrally joined with the proximal probe portion 424 of the second stream probe 402.

In one exemplary embodiment, the signal may be a pressure signal, in which case the detection apparatus may further include a pressure sensor P5 that is configured and disposed to detect a pressure signal in the proximal portion 414 of the first stream probe. Additionally, a pressure sensor P6 may be configured and disposed to detect a pressure signal in the proximal portion 424 of the second stream probe 420. Since there is fluid communication between the cylinder 125, the fluid conduit member 403, plenum 404, and the proximal probe portions 414 and 424 and distal probe portions 410 and 420 of the first and second stream probes 410 and 420, a restriction orifice 417 is disposed in the proximal portion 414 of the first stream probe 410 and at least one restriction orifice 418a disposed in the proximal portion 424 of the second stream probe 420. In one further exemplary embodiment, a second restriction orifice 418b may be disposed in the proximal portion 424 of the second stream probe 420.

The presence of the restriction orifices 417 and at least 418a or 418b is necessary to restrict undesirable interaction between the signal present in the first stream probe 410 and the signal present in the second stream probe 420. In addition, the restriction orifices 417 and at least 418a, and in one exemplary embodiment 418b, improve the response time of the pressure sensors P5 and P6 since only the volumes of the stream probes 401 and 402 downstream of the restriction orifices 417 and 418a and/or 418b are relevant and the stream probes 401 and 402, respectively, behave more closely or approximately as flow sources rather than as pressure sources. The volume upstream of the restriction orifices 417 and 418a and/or 418b becomes less relevant.

As also illustrated in FIG. 10, the detection apparatus 400 also further includes controller 225 that now processes pressure readings sensed by the pressure sensors P5 and P6 and determines whether the pressure readings are indicative of detection of a substance 116 that may be present on the surface (31, 33) based on measurement of a signal, correlating to a substance 116 at least partially obstructing the passage of fluid 30 through the open port 416 of the distal tip 412 of the distal probe portion 410 of the first stream probe 401 and confirmation that the substance 116 is not the gums of the subject or of the user of the detection apparatus 400 and not the generation of a false positive alarm signal that the substance is the gums of the subject or of the user of the detection apparatus 400. The controller 225 includes memory (not shown) for storage of the data. As indicated above, the confirmation that the substance 116 is not the gums of the subject or the user of the detection apparatus 400 and not the generation of a false positive alarm signal that the substance is the gums of the subject or of the user of the detection apparatus 400 is effected by comparison between the measurement of the signal correlating to a substance 116 at least partially obstructing the passage of fluid 30 through the open port 416 of the distal tip 412 of the distal probe portion 410 of the first stream probe 401 and measurement of a signal correlating to an object not obstructing the passage of fluid 30 through the open port 426 of the distal tip 422 of the distal probe portion 420 of the second stream probe 420. The detection apparatus 400 may further include, for operation of the plunger 126, the stream probe operating apparatus 3100 and motor 3300 (see FIGS. 20-22), battery 270 and, as indicated above, the controller 225 (see also FIG. 10). The pressure sensors P5 and P6 are in electrical communication with the controller 225. The controller 225 generates an alarm or signal to the user in the same manner as described previously.

As may be appreciated from FIGS. 23, 24 and 25A, in the exemplary embodiments illustrated therein, the proximal probe portion 424 of the second stream probe 420 is arranged concentrically around the proximal probe portion 414 of the first stream probe 410.

The distal probe portion 410 of the first stream probe 401 defines a longitudinal axis A-A and the distal probe portion 420 of the second stream probe 402 defines longitudinal axis A'-A' and each define a circular cross-section in a direction transverse to the respective longitudinal axes A-A and A'-A'. As illustrated in FIGS. 23, 24 and 25A, the longitudinal axes A-A and A'-A' may coincide, or they may be offset from, and parallel to, one another (not shown).

As illustrated in FIGS. 23 and 25A, the open port 426 of the distal tip 422 of the distal probe portion 420 of the second stream probe 402 is arranged concentrically around the open port 416 of the distal tip 412 of the distal probe portion 410 of the first stream probe 401. Those skilled in the art will recognize that other embodiments of the present disclosure may be configured wherein the proximal probe portion 424 of the second stream probe 420 is not arranged concentrically around the proximal probe portion 414 of the first stream probe 410, particularly wherein the axes A-A and A'-A' are parallel to, but offset from, one another.

This technique uses common technology with the stream probe plaque detection method described above so components such as the stream-pump can be shared in the handle or body portion to reduce the total bill of material. From an industrialization point of view, the same type of technology, sourcing of components etc. can be applied (re-use, commonality).

Since detection apparatus 400 is directed to applying a second, additional stream tube in order to detect only gums and not plaque, in one exemplary embodiment, the first stream probe 401 for plaque detection is centered inside the larger diameter second stream probe 402 to be used for gum detection. When configured in this manner, the second stream probe 402 for the gum detection moves along the same route, i.e., along axis A-A, as the first stream probe 401 for the plaque detection. In this manner, both generated pressure signals P5 and P6 can be compared at, for all practical purposes, exactly the same spot in the mouth of the subject or of the user of the detection apparatus 400.

As illustrated in FIG. 25A, the profile of the distal tip 422 of the distal probe portion 420 of the second stream probe 402 for gum detection should be such that the second steam probe 402 is unable to detect plaque, while still capable of detecting gums.

More particularly, as illustrated in FIGS. 23, 24 and 25A, the distal probe portion 410 of the first stream probe 401 and the distal probe portion 420 of the second stream probe 402 define a common longitudinal axis, e.g., axis A-A coinciding with axis A'-A'. The distal tip 412 of the distal probe portion 410 of the first steam probe 401 and the distal tip 422 of the distal probe portion 420 of the second stream probe 402 each define a concave profile in a direction transverse to the common longitudinal axis A-A or A'-A' and with respect to respective proximal ends 412' and 422', defined with respect to the common longitudinal axis, A-A or A'-A' of the distal probe portion 410 of the first stream probe 401 and the distal probe portion 420 of the second stream probe 402, respectively. The profile of the distal tip 422 includes a flat perimeter 428 that circumferentially extends around the open port 426 of the distal tip 422.

The distal tip 412 of the first stream probe 401 has a concave or arched profile that defines a diameter d1 and a distance x1 extending proximally along the axis A-A that is maximum at trough 418 at the intersection with the axis A-A. The distance x1 thus limits the distance of the distal tip 412 from the dental surface interfacing with the distal tip 412 so as to be less than the height of the plaque layer, i.e., generally 100 microns (μm), away from the dental surface. Therefore, the probe tip 412 will be capable of detecting plaque since the open port 416 will be obstructed upon encountering plaque.

The distal tip 422 of the distal portion 420 of the second stream probe 402 for gum detection defines a comparatively larger diameter d2 as compared to the diameter d1 of the distal tip 412 of the first stream probe 401 and also defines a distance x2 extending proximally along the axis A-a or A'-a' that is maximum at trough 427. The dimensions of diameter d2 and the distance x2 are such that, generally, plaque will not be capable of obstructing the open port 426 This is attributable, in part, to the fact that the two probes 401 and 402 generally are inclined at an angle with respect to the tooth surface, and therefore leakage through the open port 426 should occur more readily.

The detection of plaque or gums is a function of both size and shape of the probe tip, particularly the curvature at the probe tip. If the curvature has a large radius R, the distal tip 422 is easily blocked by the gums. If the distal tip 422 has a small radius R, it is more difficult for the gums to deform to block the distal tip 422. The height x2 of the opening created by the tip curvature R determines how thick the plaque layer needs to be to obstruct the distal tip 422. By providing second probe 402 with a large diameter d2, and large radius of curvature R, the distal tip 422 is easily blocked by gums but not by plaque.

Generally, diameter d2 of the opening of open port 426 of distal tip 422 of the distal probe portion 420 of the second stream probe 402 can be equal to or larger than about 250 μm, and should generally not exceed 500 μm, thus ranging from about 250 μm to about 500 μm. The radius of curvature R should be significantly greater than one-half of the diameter d2. Correspondingly, diameter d1 of the opening of open port 416 of distal tip 412 of the distal probe portion 410 of the first stream probe 401 can be less than or equal to about 300 μm or range from about 150 μm to about 300 μm with a radius of curvature r of about one-half the diameter d1.

Those skilled in the art will recognize that due to the significant variability of the conditions occurring during usage of the detection apparatus 400 such as exposure to saliva, toothpaste, food particles, plaque, etc, these dimensional ranges are not hard limits and may vary based on usage experience.

FIGS. 25B and 25C illustrate alternate exemplary embodiments of the detection apparatus 400 wherein the distal probe portion 420 of second stream probe 402 of FIGS. 23 and 25A is replaced by distal probe portion 440 and distal probe portion 460, respectively. In a similar manner as with respect to distal probe portion 420, the distal probe portions 440 and 460 each define a circular cross-section in a direction transverse to the respective longitudinal axes A-A and A'-A' as shown in FIG. 24. In FIG. 25B, open port 446 of distal tip 422 of the distal probe portion 440, now part of the second stream probe 402, is arranged concentrically around the open port 416 of the distal tip 412 of the distal probe portion 410 of the first stream probe 401. However, in contrast to distal probe portion 420, the distal tip 442 of distal probe portion 440 of the second stream probe 402 defines a convex profile with respect to the distal tip 442 along the common longitudinal axis A-A or A'-A' and with respect to the respective proximal ends 412' and 422'. The concave profile of the distal tip 412 remains as in FIGS. 23, 24 and 25A.

The convex profile of distal tip 442 now extends proximally along the axis A-A or A'-A' a distance x2' to define an apex or arcuate point of intersection 444. More particularly, the convex profile defined by the distal tip 442 of the distal probe portion 440 of the second stream probe 402 is defined by the arcuate point of intersection 444 between two straight lines 448.

In FIG. 25C, open port 466 of distal tip 462 of distal probe portion 460, which is now part of the second stream probe 402, is again arranged concentrically around the open port 416 of the distal tip 412 of the distal probe portion 410 of the first stream probe 401. Again, in contrast to distal probe portion 420, the distal tip 462 of distal probe portion 460 of the second stream probe 402, having now radius of curvature R' which is inverted as compared to radius of curvature R of the distal probe portion 420, also defines a convex profile with respect to the distal tip 462 along the common longitudinal axis A-A or A'-A' and with respect to the respective proximal ends 412' and 422'. The concave profile of the distal tip 412 remains as in FIGS. 23, 24, 25A and 25B.

Again, the convex profile of distal tip 462 extends proximally along the axis A-A or A'-A' distance x2' to define an apex 464. However, in contrast to the apex or arcuate point of intersection 444, the convex profile defined by the distal tip 462 of the distal probe portion 460 of the second stream probe 402 defines a smooth arcuate profile such that apex 464 is itself also defined by a smooth arcuate profile.

As with respect to distal portion 420, for both distal probe portion 440 illustrated in FIG. 25B and distal probe portion 460 illustrated in FIG. 25C, the dimensions of diameter d2 and the distance x2' are such that, generally, plaque will not be capable of obstructing the respective open ports 446 and 466.

Turning now to FIG. 25D, in another alternate exemplary embodiment of the detection apparatus 400, distal probe portion 460 of FIG. 25C is now arranged concentrically around an alternate exemplary embodiment of distal probe portion 410 of first stream probe 401. More particularly, distal probe portion 430 of the first stream probe 401 for plaque detection and the distal probe portion 460 of the second stream probe 402 for gum detection define a common longitudinal axis A-A, A'-A'. However, the distal tip 462 of the distal probe portion 460 and the distal tip 412 of distal probe portion 410 each define a convex profile in a direction transverse to the common longitudinal axis A-A, A'-A', and with respect to respective proximal ends 412', 422', defined with respect to the common longitudinal axis A-A, A'-A'. Distal tip 462 of distal probe portion 460 defines a convex radius of curvature r' in contrast to the concave radius of curvature r defined by distal tip 412 of distal probe portion 410 of first stream probe 401.

In a similar manner as with respect to distance x1 defined with respect to distal tip 412, distal tip 432 of the first stream probe 401 has a convex or arched profile that defines diameter d1 and a distance x1' extending distally along the axis A-A that is maximum at apex 434 at the intersection with the axis A-A. The distance x1' thus also limits the distance of the distal tip 432 from the dental surface interfacing with the distal tip 432 so as to be less than the height of the plaque layer, i.e., generally 100 microns (μm), away from the dental surface. Therefore, the probe tip 432 will also be capable of detecting plaque since the open port 436 will be obstructed upon encountering plaque.

Those skilled in the art will recognize that, and understand how, the alternate exemplary embodiments of the distal probe portions 430, and 440 and 460, may be utilized in the same manner with respect to detection apparatus 400 described above with respect to FIG. 23 concerning distal probe portions 410 and 420, respectively. Both the plaque detection distal probe portions 410 and 430 and the gum detection distal probe portions 420, 440 and 460 may be made of the same material such as hard polymers polyamide (Nylon) or polyetheretherketone (PEEK) for wear resistance or softer materials such as silicon rubber or polyurethane to provide a softer, more comfortable sensation to the user or subject. Alternatively, the inner or plaque detection distal probe portions 410 and 430 may be made from the hard polymers such as polyamide (Nylon) or polyetheretherketone (PEEK) for wear resistance while the outer or gum detection distal probe portions 420, 440 and 460 may be made from the softer materials such as silicon rubber or polyurethane to provide a softer, more comfortable sensation to the user or subject. Alternatively, this selection of materials may be reversed as design requirements and/or product usage experience dictate.

Turning now to FIGS. 26A-26C, there are illustrated further alternate exemplary embodiments of the distal probe portion 410 of the first stream probe 401 and of the distal probe portion 420 of the second stream probe 402. More particularly, referring to FIG. 26A, distal probe portion 410 or 430 of first stream probe 401 again defines longitudinal axis A-A and distal probe portion 480 of second stream probe 402 also defines longitudinal axis A'-A'. Open port 484 of distal tip 482 of the distal probe portion 480 of the second stream probe 402 is also arranged concentrically around the open port area 416 or 436 of the distal tip 412 or 432 of the distal probe portion 410 or 430, respectively, of the first stream probe 401 and such that the longitudinal axes A-A and A'-a' are parallel to one another. However, the distal probe portion 480 of the second stream probe 402 defines an arcuate, non-circular cross section in a direction transverse to the longitudinal axis A'-A' of the distal probe portion 480 of the second stream probe 402. Again, the distal probe portion 410 of the first stream probe 401 defines a circular cross section in a direction transverse to the longitudinal axis A-A or A'-A' of the distal probe portion 480 of the second stream probe 402.

In the alternate exemplary embodiment of FIG. 26A, the distal probe portion 480 of the second stream probe 402 defines an inner surface 485 along longitudinal axis A'-A'. The distal probe portion 410, 430 of the first stream probe 401 defines an outer surface 415, 435, respectively, along longitudinal axis A-A. The outer surface 415, 435 does not contact the inner surface 485.

FIG. 26B illustrates yet another alternate exemplary embodiment of the distal probe portion 410 of the first stream probe 401. More particularly, again, the distal probe portion 480 of the second stream probe 402 defines inner surface 485 along longitudinal axis A'-A'. The distal probe portion 480 of the second stream probe 402 defines an elliptical cross section with a minor axis B1-B1 along which width W of the elliptical cross-section is defined. Major axis B2-B2 defines length L of the elliptical cross section. However, in contrast to the distal probe portions 410 and 430 illustrated in FIG. 26A, distal probe portion 450 of the first stream probe 401 defines an outer surface 455 along its longitudinal axis A-A and defines a diameter d3 that is greater than diameter d1 of distal probe portions 410 and 430. The diameter d3 is approximately equal to the width W of the distal probe portion 480 such that the outer surface 455 of the distal probe portion 450 of the first stream probe 401 contacts the inner surface 485 of the distal probe portion 480 of the second stream probe 402 to define first and second lines of contact coinciding with the minor axis B1-B1.

Although the distal probe portion 450 provides a flow restriction effect at the first and second lines of contact, the cross-sectional area of open port 484 of the elliptical shape defined by the elliptical cross-section of the distal probe portion 480 of the second stream probe 402 exceeds the cross-sectional area of open port 456 of distal tip 452 of the distal probe portion 450 of the first stream probe 401 to enable detection of the gums of a subject or of a user of the detection apparatus 400 while the distal probe portion 450 has a cross-sectional area via open port 456 designed to detect plaque as described above.

FIG. 26C illustrates still another alternate exemplary embodiment of the distal probe portion 410 of the first stream probe 401. More particularly, again, the distal probe portion 480 of the second stream probe 402 defines inner surface 485 along longitudinal axis A'-A'. The distal probe portion 480 of the second stream probe 402 defines an elliptical cross section with a minor axis B1-B1 along which width W of the elliptical cross-section is defined. Major axis B2-B2 defines length L of the elliptical cross section. However, in contrast to the distal probe portion 450 illustrated in FIG. 26B, distal probe portion 470 of the first stream probe 401 is formed by a pair of parallel plates 472 and 474 each defining lateral edges 4721, 4722 and 4741, 4742, respectively, and again defining common longitudinal axis A-A with respect to the longitudinal axis A'-A' of the distal probe portion 480 of the second stream probe 402. The lateral edges 4721, 4722 and 4741, 4742 of the parallel plates 472 and 474, respectively, are in contact with the inner surface 485 of the distal probe portion 480 of the second stream probe 402.

Again, the elliptical cross-section of the distal probe portion 480 of the second stream probe 402 exceeds the cross-sectional area of open port 476 of the distal probe portion 470 between the parallel plates 471 and 472 of the first stream probe 401 to enable detection of the gums of a subject or of a user of the detection apparatus 400 while the distal probe portion 470 has a cross-sectional area via open port 476 designed to detect plaque as described above.

The detection apparatus 400 as represented in FIGS. 26A-26C also includes restriction orifices 417, 418a and 418b and the couplers or connectors 406' and 406" that may be either separate members from one another or formed integrally as a common coupler or connector 406 having joining posts 4061 and 4062 illustrated in the cross-sectional view of FIG. 24. Additionally, those skilled in the art will recognize that, and understand how, the plenum 404 in FIG. 23 is designed and configured to conform at least to the elliptical cross-sectional shape of the distal probe portion 480 of the second stream probe 402.

The elliptical cross-section of the distal probe portion 480 in FIGS. 26A-26C along the longitudinal axis A-A or A'-A' improves the detection of the gum line as the distal tip 482 can then enter more easily into difficult to reach areas. Also, the greater width W of the distal probe portion 480 in the direction of the longitudinal axis A-A or A'-A' tends to prevent the distal tip 482 of the gum detector or second stream probe 402 from entering too deeply into the interproximal areas of the gums.

Figure 27:
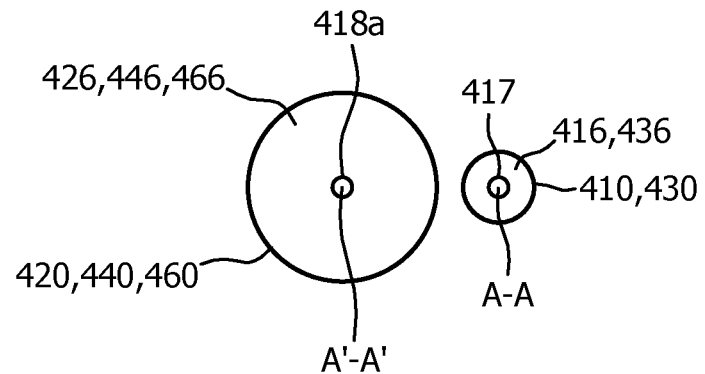
FIG. 27 illustrates still another alternate exemplary embodiment of the distal probe portions of the first and second stream probes of FIGS. 23-25D wherein the distal probe portion of the first stream probe and the distal probe portion of the second stream probe are disposed separately in proximity to one another and such that the longitudinal axes are parallel to one another.
Figure 29:
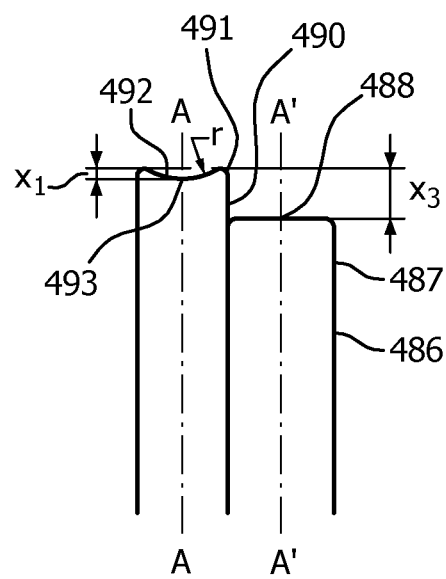
FIG. 29 illustrates yet another alternate exemplary embodiment of the distal probe portions of FIGS. 27 and 28 except that except that the distal tip of the distal probe portion extends distally beyond the distal tip of the distal probe portion of the second stream probe and each distal tip has a flat or straight or flush profile.

Turning now to FIGS. 27-29, there are illustrated alternate exemplary embodiments of the detection apparatus 400 of the present disclosure wherein the distal probe portion of the first stream probe and the distal probe portion of the second stream probe are disposed in proximity to one another and such that the longitudinal axes are parallel to one another, and thus are separate from one another and not concentrically arranged with respect to each other.

More particularly, referring to FIG. 27 in conjunction with FIGS. 23-25D, again, distal probe portion 410 or 430 of the first stream probe 401 defines longitudinal axis A-A (into the paper) and the distal probe portion 420, 440 or 460 of the second stream probe 402 defines longitudinal axis A'-A' (into the paper) and each define a circular cross-section in a direction transverse to the respective longitudinal axes A-A and A'-A'. Additionally, the distal probe portion 410 or 430 of the first stream probe 401 and the distal probe portion 420, 440 or 460 of the second stream probe 402 are disposed in proximity to one another and such that the longitudinal axes A-A and A'-A' are parallel to one another. Again, as discussed above with respect to FIGS. 23-25D, the dimensions of diameter d1 and d2 and the distances x1, x1' and x2, x2' are such that, generally, plaque will not be capable of obstructing the respective open ports 426, 446 and 466.

Thus, the second stream probe 402 for detection of the gums is located near the first stream probe 401 for detection of plaque. Generally, both are placed along the long axis of the distal oral insertion portion 250 or brush head (see FIG. 10), so that both probe 401 and probe 402 contact the gum line at the same time.

FIG. 28 illustrates another alternate exemplary embodiment of the detection apparatus 400 analogous to the alternate exemplary embodiment of the detection apparatus 400 described above with respect to FIG. 27 except that distal portions 420, 440 and 460 of the second stream probe 402 having circular cross-sections are replaced with distal portion 480 wherein again the distal probe portion 480 defines an arcuate, non-circular cross section in the direction transverse to the longitudinal axis A'-A' of the distal probe portion 480 of the second stream probe 402.

Again, the elliptical cross-section of the distal probe portion 480 in FIGS. 26A-26C along the longitudinal axis A'-A', as illustrated in FIG. 28, improves the detection of the gum line as the distal tip 482 can then enter more easily into difficult to reach areas. Also, the greater width W of the distal probe portion 480 in the direction of the longitudinal axis A-A or A'-A' tends to prevent the distal tip 482 of the gum detector or second stream probe 402 from entering too deeply into the interproximal areas of the gums.

FIG. 29 illustrates yet another alternate exemplary embodiment of the detection apparatus 400 analogous to the alternate exemplary embodiment of the detection apparatus 400 described above with respect to FIGS. 27 and 28 except that distal portions 420, 440 and 460 of the second stream probe 402 having circular cross-sections and distal probe portion 480 that defines an arcuate, non-circular cross section in the direction transverse to the longitudinal axis A'-A' of the distal probe portion 480 of the second stream probe 402 are replaced with distal probe portion 486 of the second stream probe 402 that defines a circular cross-section.

Distal probe portion 490 also defines longitudinal axis A-A and is generally similar to distal probe portions 410 and 430. The cross-sectional area of open port 492 of distal tip 491 of distal probe portion 490 of the first stream probe 401 for plaque detection is generally equal to the cross-sectional area of distal probe portion 486 of the second stream probe 402 for gum detection. The distal tip 491 of the first stream probe 401 also has a concave or arched profile that defines radius of curvature r, diameter d1 and distance x1 that extends proximally along the axis A-A and is maximum at trough 493 at the intersection with the axis A-A. In a similar manner as described above, distance x1 thus limits the distance of the distal tip 491 from the dental surface interfacing with the distal tip 491 so as to be less than the height of the plaque layer, i.e., generally 100 microns (µm), away from the dental surface. Therefore, the probe tip 490 will be capable of detecting plaque since the open port 416 will be obstructed upon encountering plaque.

In contrast, distal tip 487 of distal probe portion 486 has an open port 488 and has a flat or straight or flush profile with respect to the longitudinal axis A'-A', as opposed to the concave or convex profiles described above with respect to FIGS. 23-25D. The flat profile enhances the accuracy of the signal detecting the gums.

Again, as in FIGS. 27 and 28, distal probe portion 490 of the first stream probe 401 for plaque detection and distal probe portion 486 of the second stream probe 402 for gum detection each define longitudinal axes A-A and A'-A, respectively, wherein the distal probe portion 490 and the distal probe portion 486 are disposed adjacent to one another and, in one exemplary embodiment, attached to one another, such that the longitudinal axes A-A and A'-A' are parallel to one another. However, the distal tip 491 of the distal probe portion 490 of the first stream probe 401 now extends distally a distance x3 along longitudinal axis A-A beyond the distal tip 487 of the distal probe portion 486 of the second stream probe 402. Thus, distal probe portion 486 of the second stream probe 402 for gum detection does not become obstructed by dental plaque, and thus enables gum detection when distal probe portion 490 of the first steam probe 401 does become obstructed by dental plaque.

Figure 13:
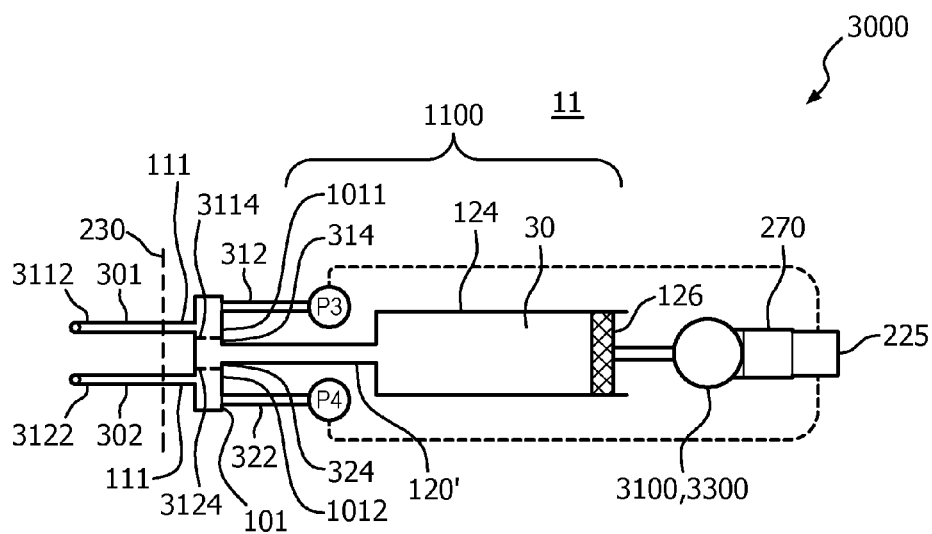
FIG. 13 illustrates an alternate exemplary embodiment of the stream probe of FIG. 4A having a pump portion supplying a continuous stream of gas via a tube to two probe tips while measuring the internal tube pressure at the inlet to a first stream probe tip and the internal pressure at the inlet to a second stream probe tip.

It should be noted that the exemplary embodiments of separate distal probe portions described with respect to, and illustrated in, FIGS. 27-29 are incorporated with the detection apparatus 1100 illustrated in FIG. 13 which operates separate stream probes 301 and 302 rather than the detection apparatus 400 described with respect to, and illustrated in FIG. 23, which operates concentric stream probes 401 and 402. In the detection apparatus 1100, the distal tee connection 101 is modified to accommodate the particular cross-sectional shape of the distal probe portions 420, 440, 460, 480 or 486 of the second stream probe 402 that are in fluid communication with the distal tee connection 101.

As described above, it is observed that the first stream probe for plaque detection may also give a pressure signal when it is placed on the gums. The relatively soft gums results in (partial) blocking of the stream. This blocking results in the generation of false positive signals by the first stream probe. The user may think that plaque is present, while actually the sensor position is on the gum. The second stream probe for plaque detection is designed to determine when the second stream probe is placed on the gums of the user and to override the false positive signal.

It should be noted that while the stream probes illustrated in FIGS. 23-29 generally are characterized by an arcuate cross section, polygonal shapes such as triangular, square, rectangular, pentagonal, etc. may also be employed.

FIGS. 30-46 illustrate other exemplary embodiments of a detection apparatus for detecting the presence of a substance on a surface according to the present disclosure to override false positive signals triggered by the first stream probe being placed on the gums of the user or of the subject and falsely signaling the presence of plaque. More particularly, an optical gum detector according to embodiments of the present disclosure provides a solution for false positive signals using the stream probes for plaque detection as described above, i.e., the false positive signals occur due to blocking of the stream probe on gum that may be interpreted as plaque.

The basis for applying an optical gum detector is to measure the ratio in reflected light for wavelengths below and above the sharp transition at 600 nm wavelength in the reflectivity of gums. This reflectivity ratio displays a good contrast between gum and teeth. A threshold can be set to distinguish between a stream probe position on gum and a stream probe position on a tooth or teeth, thereby overriding false positive signals for plaque detection by the stream probe.

Figure 30:
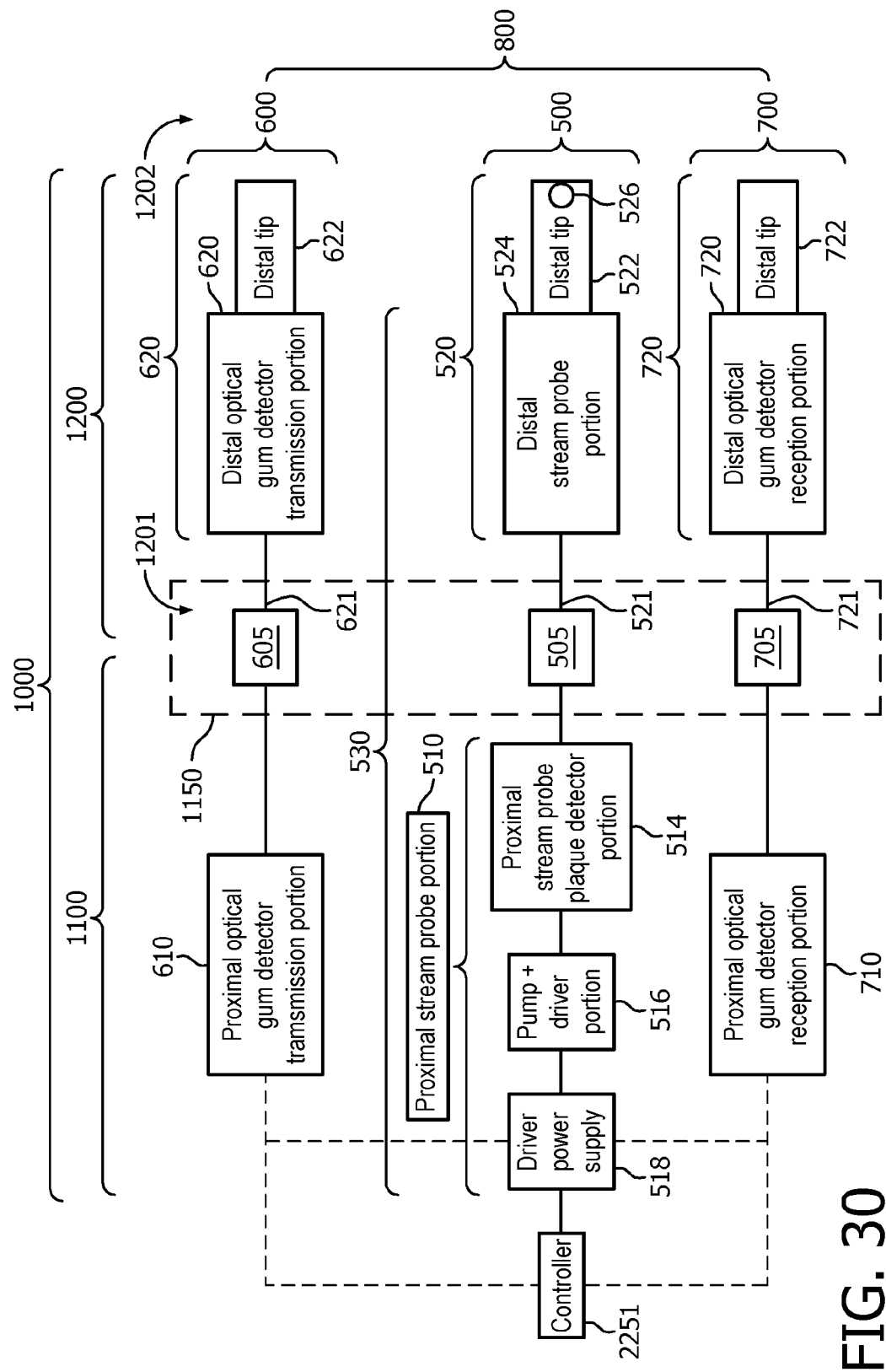
FIG. 30 is a generic composite partially schematic block diagram of a detection apparatus that includes a stream probe to detect plaque and an optical gum detector to detect the gum of a subject or of a user of the apparatus according to one exemplary embodiment of the present disclosure.

FIG. 30 is a generic block diagram of a dental hygiene detector apparatus 1000 according to the present disclosure that includes a generic composite illustration of a plaque detection apparatus 500. Plaque detection apparatus 500 includes a single stream probe representative of first stream probe 301 in FIG. 13 and first stream probe 401 in FIG. 23. In place of the second stream probe 302 in FIG. 13 or the second stream probe 402 in FIG. 23 for detecting the gums of the user or of a subject, an optical gum detector 800 is used in conjunction with plaque detection apparatus or stream probe 500 for detecting plaque. The optical gum detector 800 provides an indication if distal tip 522 of the stream probe 500 is positioned on the gums or on a tooth or teeth of a subject or of a user. Based on the information provided by the optical gum detector 800, the frequency of false positive signals triggered by the presence of the stream probe 500 on the gums can be reduced.

More particularly, as illustrated in FIG. 30 in a composite generic manner, dental hygiene detection apparatus 1000 for detecting the presence of a substance such as plaque on a surface such as a tooth or teeth includes a distal oral insertion portion 1200 defining a proximal end 1201 and a distal end 1202. The distal oral insertion portion 1200 includes a distal probe portion 520 of stream probe 500 that is configured to be immersed in first fluid 11 (see FIG. 7). The distal probe portion 520) defines distal tip 522 having an open port 526 to enable passage of second fluid 30, or 35 (see FIG. 7) through the open port 526. The open port 526 has a cross-sectional area sufficient and a shape configured to detect a substance 116 that may be present on surface 31 or 33 as described above with respect to FIG. 7 and FIGS. 23-30.

In one exemplary embodiment, the distal oral insertion portion 1200 further includes a mechanical coupler or connection 505 that is positioned at the proximal end 1201 of the distal oral insertion portion 1200. The distal probe portion 520 may be coupled to the mechanical connection 505.

Optical gum detector 800 includes distal optical gum detector transmission portion 620 that defines a proximal end 621 and a distal tip 622. The distal tip 622 extends to the vicinity of the distal end 1202 of the distal oral insertion portion 1200. Optical gum detector 800 further includes a distal optical gum detector reception portion 720 that defines a proximal end 721 and a distal tip 722. The distal optical gum detector reception portion 720 extends to the vicinity of the distal end 1202 of the distal oral insertion portion 1200.

In one exemplary embodiment, the distal oral insertion portion 1200 further includes a transmitting coupler 605 positioned at the proximal end 1201 of the distal oral insertion portion 1200. The distal optical gum detector transmission portion 620 is coupled to the transmitting coupler 605. The distal oral insertion portion 1200 may further include a receiving coupler 705 positioned at the proximal end 1201 of the distal oral insertion portion 1200. The distal optical gum detector reception portion 720 may be coupled to the receiving coupler 705.

The detection apparatus 1000 further includes a proximal body portion 1100. In one exemplary embodiment, proximal body portion 1100 includes a proximal stream probe portion 510, which in turn includes a proximal stream probe plaque detector portion 514 that may be coupled to distal probe portion 520 via the mechanical connection 505. Proximal body portion 1100 further includes pump driver portion 516 and pump driver and power supply 518 which is mechanically coupled to the pump driver portion 516 to operate the pump driver portion 516 to supply pressure to or withdraw pressure from the proximal stream probe plaque detector portion 514 and the distal probe portion 520 for plaque detection. A process controller 2251 similar to process controller 225 described above with respect to FIG. 10 is in electrical communication with the pump driver and power supply 518 to control operation of the distal oral insertion portion 1200. The controller 2251 includes memory (not shown) for storage of data.

Those skilled in the art will recognize that stream probe 500 may be configured, for example, as either stream probe 100 described above with respect to FIG. 4A, or stream probe 100' described above with respect to FIG. 4B or stream probe 100" described above with respect to FIG. 4C.

In one exemplary embodiment, the proximal body portion 1100 includes a proximal optical gum detector transmission portion 610 that is optically coupled to the distal optical gum detector transmitting portion 620. The optical coupling therebetween may be via the transmitting coupler 605.

In one exemplary embodiment, the proximal body portion 1100 further includes a proximal optical gum detector reception portion 710 optically coupled to the distal optical gum detector receiving portion 720. The optical coupling therebetween may be via the receiving coupler 705.

The detection apparatus 1000 is configured such that passage of the second fluid 30 or 35 through the distal tip 522 of the distal probe portion 520 enables detection of a substance 116 that may be present on the surface 31, 33 (see FIG. 7) based on measurement of a stream probe signal correlating to a substance 116 at least partially obstructing the passage of fluid 30 or 35 through the open port 526 of the distal tip 522 of the distal probe portion 520, which includes distal stream probe portion 524 and distal tip 522, and is configured such that the distal optical gum detector transmission portion 620 and the distal optical gum detector reception portion 720 are in a position to transmit and to receive, respectively, an optical signal that, upon transmission of the optical signal and reception of the optical signal by process controller 2251, enables the process controller 2251 to determine if the open port 526 of the distal tip 522 of the distal probe portion 520 is in contact with a substance 116 that is at least partially obstructing the passage of fluid 30, 35 through the open port 526 and that is not in contact with the gums of a subject or of a user of the detection apparatus 1000.

The sampling rate, based on the frequency of the light pulses from the proximal optical gum detector transmission portion 610, is preferably chosen high enough, such that bristle movement of 250 Hz can be followed, e.g. 5 KHz. In one exemplary embodiment, the sampling rate is set at well above (>5 times) the frequency of the brush head/bristle movement. A correction for offset light on the detector and dark current from the detector can be made by measuring the signal when both of the light sources are switched off. Control of the light source pulsing frequency and readout of the detectors and data processing by microprocessor or process controller 2251, in which eventually also calibration values can be stored. When the gum detector results in a signal corresponding to gum, the eventual pressure signal from the stream probe is ignored, such that false positives by the gum are overridden.

The optimum wavelengths for detection are below 600 nm (preferably between 450 and 600 nm) for the short wavelength and above 600 nm (preferably between 630 and 800 nm) for the long wavelength.

Alternatively, generically, sampling can be performed in synchronization with the frequency of the brush head/bristle movement for the exemplary embodiments illustrated and described in FIG. 31, 32, or 40-44 described below.

For any of the foregoing methods, the microprocessor or controller 2251 may be in electrical communication with the proximal optical gum detector reception portion 710 and the proximal optical gum detector transmission portion 610. The microprocessor or controller 2251 may process the signals in part by performing an analog to digital conversion.

Processing of the data involves:

Obtaining signals for wavelengths $\lambda 1$ and $\lambda 2$.

Determining offset values based on measurement of background light levels.

Correcting wavelength signal values $\lambda 1$ and $\lambda 2$ by subtracting the background light level values Determining the reflectivity ratio $R=\lambda 1/\lambda 2$ based on the corrected values of $\lambda 1$ and $\lambda 2$.

Comparing the corrected value of $R=\lambda 1/\lambda 2$ with threshold value for teeth and gum.

In order to achieve optimum accuracy for the determination of $\lambda 1/\lambda 2$, a factory calibration can be used and the calibration data can be stored in the memory of the process controller 2251. Also, the calibration/threshold value can be updated based on the data recorded over a brushing session, or a number of brushing sessions, so that initially a factory set value is used, and the threshold is adjusted over time to more accurately reflect the color of a particular user's or subject's teeth and gums.

Particular exemplary embodiments of the detection apparatus 1000 described in composite form in FIG. 30 are described in FIGS. 31-32 and 40-46. Component designation numbering for the particular embodiments is presented in a fashion corresponding to the generic component designation numbering. For example, in FIG. 30, proximal optical gum detector transmission portion 610 of detection apparatus 1000 is designated in FIG. 31 as proximal optical gum detector transmission portion 610a of detection apparatus 1000a, in FIG. 32 as proximal optical gum detector transmission portion 610b of detection apparatus 1000b, etc. A similar numbering pattern is maintained throughout the detailed description of the exemplary embodiments. Composite generic plaque detection apparatus 500 is illustrated in FIGS. 31-32 and 40-44.

Figure 31:
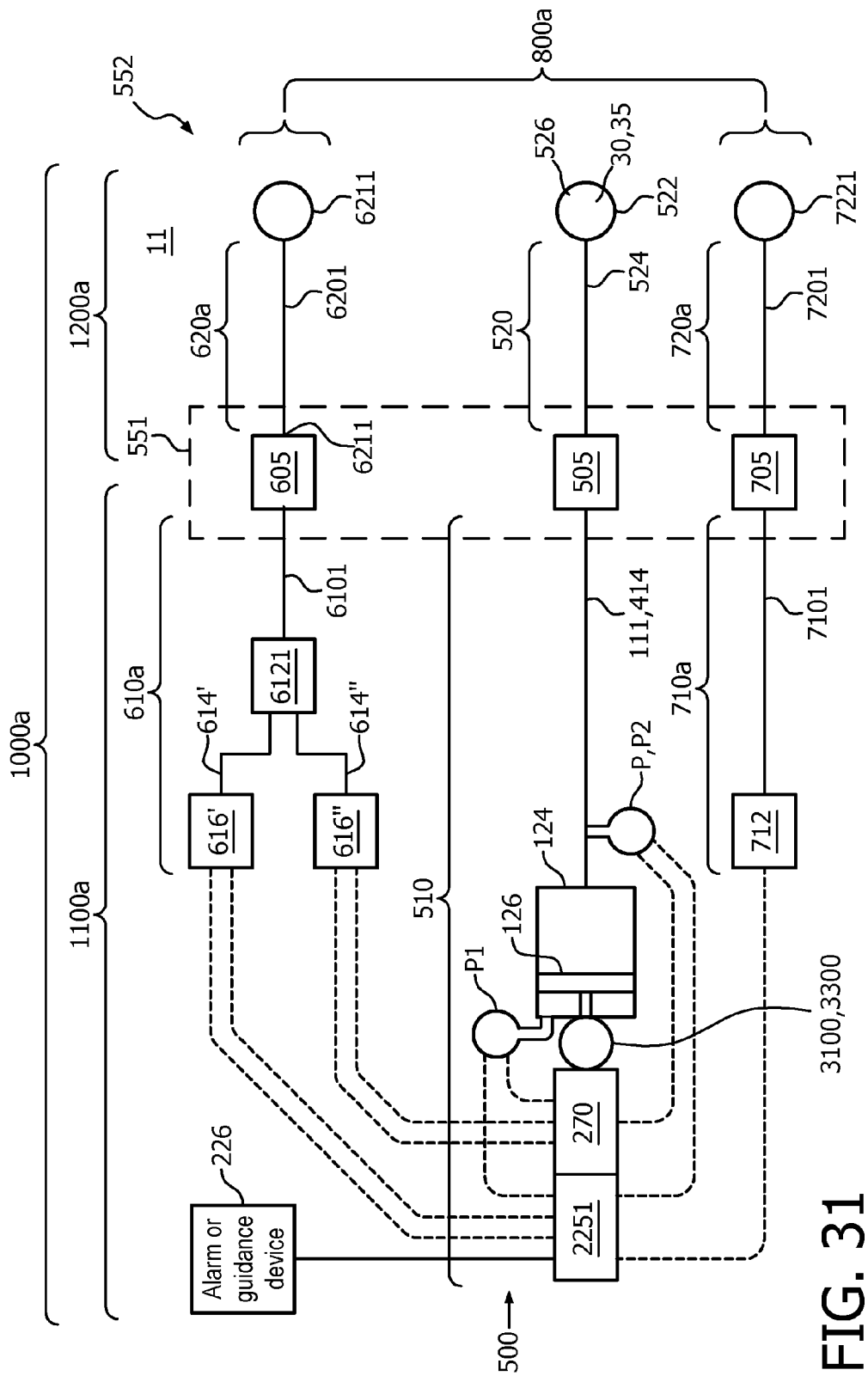
FIG. 31 illustrates one particular embodiment of a detection apparatus of FIG. 30 according to the present disclosure wherein a distal oral insertion portion includes an optical transmitting fibre and an optical receiving fibre and a proximal body portion includes multiple light sources transmitting light through a combiner to the optical transmitting fibre.

More particularly, referring to FIG. 31 in conjunction with the composite detection apparatus 1000 described with respect to FIG. 30, there is disclosed an exemplary embodiment of the present disclosure wherein detection apparatus 1000a includes composite plaque detection apparatus 500, as described above with respect to FIG. 30, and optical gum detector 800a each disposed partially on distal oral insertion portion 1200a. Distal oral insertion portion 1200a includes distal optical detector transmitting portion 620a wherein a distal transmitting optical fibre 6201 has a distal tip 6221 extending to the vicinity of distal end 1202a of the distal oral insertion portion 1200a and distal optical detector receiving portion 720a wherein a distal receiving optical fibre 7201 has a distal tip 7221 and extending from the vicinity of distal end 1202a of the distal oral insertion portion 1200a. Distal oral insertion portion 1200a further includes distal probe portion 520 defining distal tip 522 having open port 526.

Detection apparatus 1000a further includes proximal body portion 1100a that includes proximal optical gum detector transmission portion 610a. The proximal optical gum detector transmission portion 610 includes a first proximal optical transmitting fibre 6101 that may be optically coupled to the distal transmitting optical fibre 6201 via transmitting coupler 605. The proximal optical gum detector transmission portion 610a may further include an optical combiner 6121 wherein the optical combiner 6121 is optically coupled to the transmitting coupler 605 via the first proximal optical transmitting fibre 6101.

The proximal optical gum detector transmission portion 610a further includes a first light source 616', such as a light emitting diode (LED), and a second light source 616", also such as a light emitting diode. Each light source 616', 616" is optically coupled to the optical combiner 6121 to transmit light from the first and second light sources 616', 616" to the distal optical gum detector transmission portion 620a in the distal oral insertion portion 1200a.

The distal oral insertion portion 1200a includes distal optical gum detector reception portion 720a wherein a first distal receiving optical fibre 7201 may be optically coupled to the receiving coupler 705. Proximal optical gum detector reception portion 710a further includes a first proximal receiving optical fibre 7101 that may be optically coupled to the first distal receiving optical fibre 7201 via the receiving coupler 705. The proximal optical gum detector reception portion 710a further includes an optical detector 712 that is optically coupled to the first proximal receiving optical fibre 7101.

Process controller 2251 signals first light source 616' to emit a light beam at a first wavelength $\lambda 1$ and signals second light source 616" to emit a light beam at a second wavelength $\lambda 2$ where the two light beams are transmitted, via first light source to combiner optical fibre 614' and via second light source to combiner optical fibre 614", respectively, to combiner 6121 which merges the two separate light beams such that the light beams at two different wavelengths $\lambda 1$ and $\lambda 2$ are transmitted intermittently and alternately at the two different wavelengths to the distal tip 6221 via the first distal transmitting optical fibre 6201. Light emitted from the distal tip 6221 is transmitted to the distal tip 7221 of the first distal receiving optical fibre 7201 to optical detector 712 via optical coupler 705. As explained in more detail below with respect to FIGS. 35-39, in the event that plaque detection apparatus 500 signals to the process controller 2251 that plaque has been detected, detection apparatus 1000a distinguishes between white teeth and red gum by the process controller 2251 measuring the reflectivity ratio R at the two wavelengths $\lambda 1$ and $\lambda 2$.

As indicated above, the reflectivity ratio is defined as the ratio R of observed reflection levels for the two wavelengths λ1 and λ2: Thus, the reflectivity ratio R is determined, where a ratio above a certain discrimination level corresponds with teeth and a ratio below this level corresponds with gum. The optimum wavelengths for detection are below 600 nm (preferably between 450 and 600 nm) for the short wavelength and above 600 nm (preferably between 630 and 800 nm) for the long wavelength.

For detection apparatus 1000a in FIG. 31, the sampling rate may be well above (>5 times) the frequency of the brush head. The light sources 616' and 616" are alternating pulsed at the frequency of the brush/bristle movement. In between the alternate pulses by the light sources 616' and 616", background light level can be measured and the offset values calculated by the controller 2251 to yield corrected reflectivity ratios R as described above.

Upon confirmation by the process controller 2251 that plaque has been detected, the process controller 2251 initiates the alarm or guidance device 226 or the other methods of feedback to the user that have been described above with respect to FIG. 10 and FIG. 22 to continue brushing in the particular area.

Figure 32:
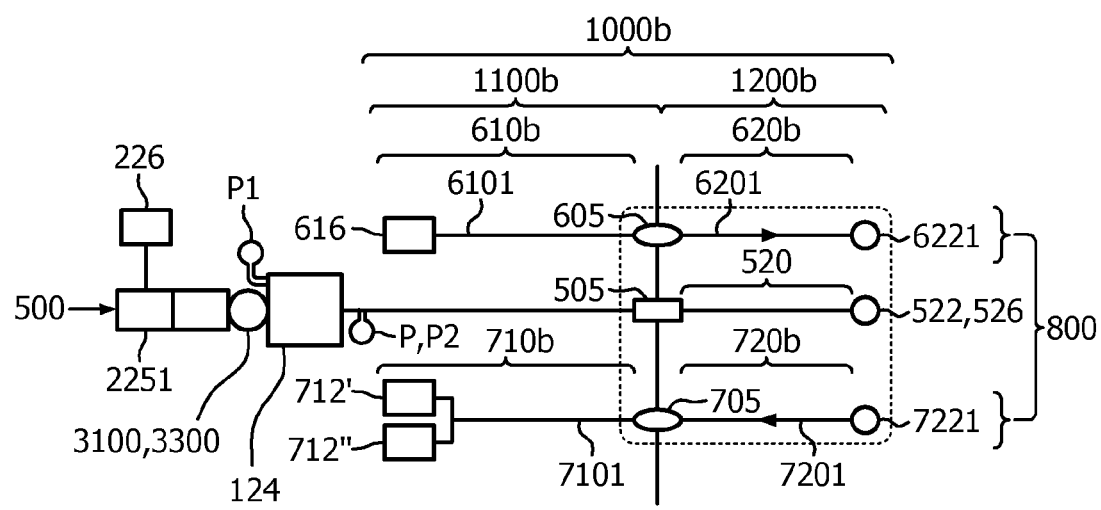
FIG. 32 illustrates another particular embodiment of a detection apparatus of FIG. 30 according to the present disclosure wherein a distal oral insertion portion includes an optical transmitting fibre and an optical receiving fibre and a proximal body portion includes an optical receiving fibre transmitting light to two optical detectors.

FIG. 32 illustrates another particular embodiment of detection apparatus 1000 of FIG. 30 according to the present disclosure wherein, in contrast to detection apparatus 1000a of FIG. 31, the distal oral insertion portion includes an optical transmitting fibre and an optical receiving fibre and the proximal body portion includes an optical receiving fibre transmitting light to two optical detectors.

More particularly, detection apparatus 1000b includes a distal oral insertion portion 1200b that is identical to distal oral insertion portion 1200a and which includes distal optical detector transmitting portion 620b and distal optical detector receiving portion 720b that are identical to distal optical detector transmitting portion 620a and distal optical detector receiving portion 720a, respectively, that have been described above with respect to detection apparatus 1000a illustrated in FIG. 31.

Proximal body portion 1100b includes proximal stream probe portion 510 of composite generic plaque detection apparatus 500. Optical gum detector 800b includes proximal optical detector transmitting portion 610b, distal optical detector transmitting portion 620b, distal optical detector receiving portion 720b and proximal optical detector receiving portion 710b.

However, proximal body portion 1100b now includes single light source 616 that may be a light emitting diode. Process controller 2251 signals light source 616 to emit a first light beam at a first wavelength λ1 and a second light beam at a second wavelength λ2 where the two light beams are transmitted concurrently via first proximal transmitting optical fiber 6101 to the distal tip 6221 of the first distal optical transmitting fibre 6201. The concurrent light beams emitted from the distal tip 6221 are collected by the distal tip 7221 of the first distal receiving optical fibre 7201 in the vicinity of the distal probe tip 522 and transported to a first light detector 712' and a second light detector 712" that are each optically coupled to first proximal receiving optical fibre 7101 via receiving coupler 705. The first light detector 712' is filtered to distinguish the first wavelength λ1 while the second light detector 712" is filtered to distinguish the second wavelength λ2.

Upon signals received by the plaque detection apparatus 500 that plaque has been detected, the process controller 2251 and the alarm or guidance device 226 operate in a similar manner as described above with respect to detection apparatus 1000a to distinguish the first wavelength λ1 and the second wavelength λ2 to determine if the probe tip 522 is actually detecting the gums rather than plaque. As indicated previously above, the optimum wavelengths for detection are below 600 nm (preferably between 450 and 600 nm) for the short wavelength and above 600 nm (preferably between 630 and 800 nm) for the long wavelength.

As is the case for the detection apparatus 1000a of FIG. 31, for detection apparatus 1000b of FIG. 32 the sampling rate may be also well above (>5 times) the frequency of the brush head. Also pulsing of the light source 616 is favorable in order to achieve background light level at each measurement point. As before, the background light level is subtracted from the wavelengths λ1 and λ2.

Figure 33:
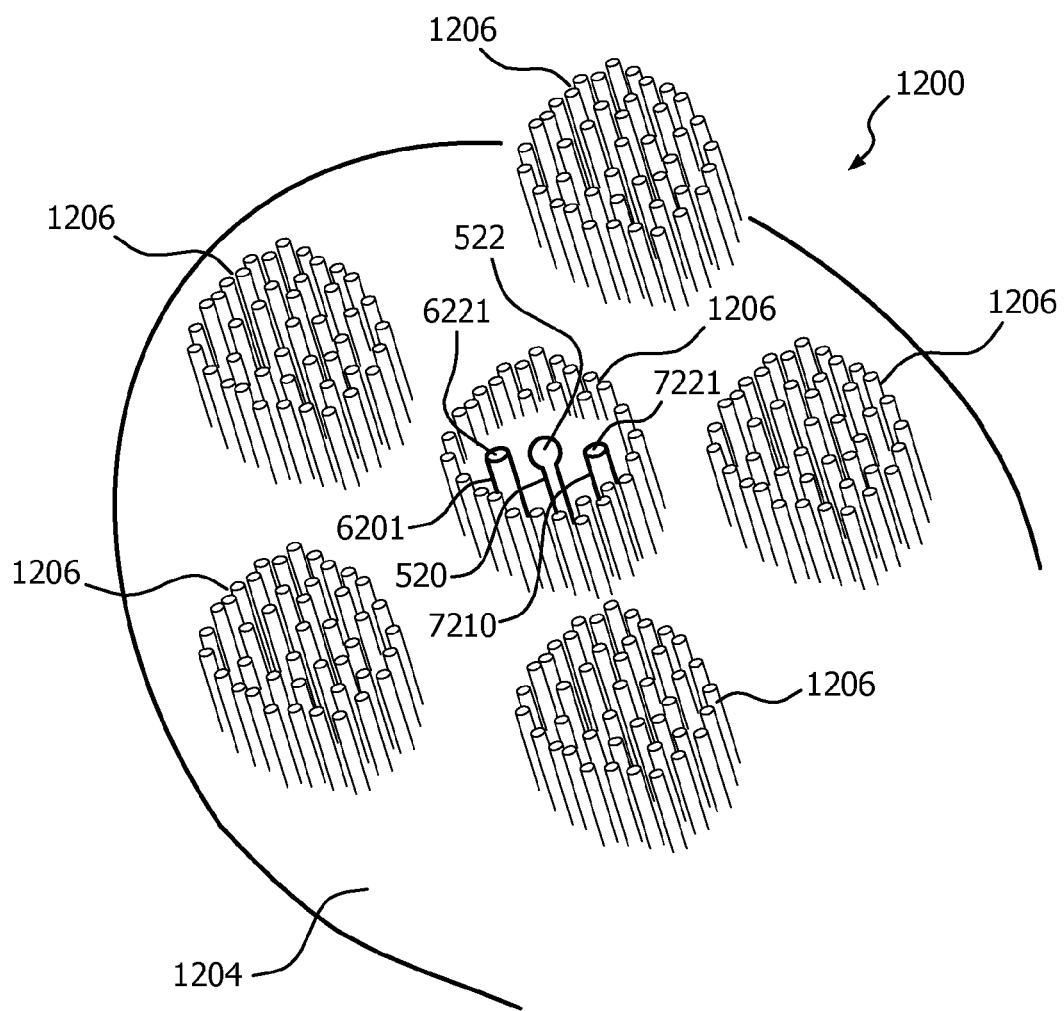
FIG. 33 illustrates a detailed view of a distal oral insertion portion of a detection apparatus according to embodiments of the present disclosure wherein the distal oral insertion portion includes a brush wherein a stream probe tip is at a position between a transmitting optical fibre and a receiving optical fibre within the bristles of the brush.

FIG. 33 illustrates a detailed view of distal oral insertion portion 1200a of detection apparatus 1000a of FIG. 31 or of distal oral insertion portion 1200b of detection apparatus 1000b of FIG. 32 according to embodiments of the present disclosure wherein the distal oral insertion portion 1200a or 1200b includes a brush 1204 wherein stream probe tip 522 of distal stream probe portion 520 is at a position between the distal tip 6221 of transmitting optical fibre 6201 and the distal tip 7221 of receiving optical fibre 7201 within the bristles 1206 of the brush 1204.

Figure 34:
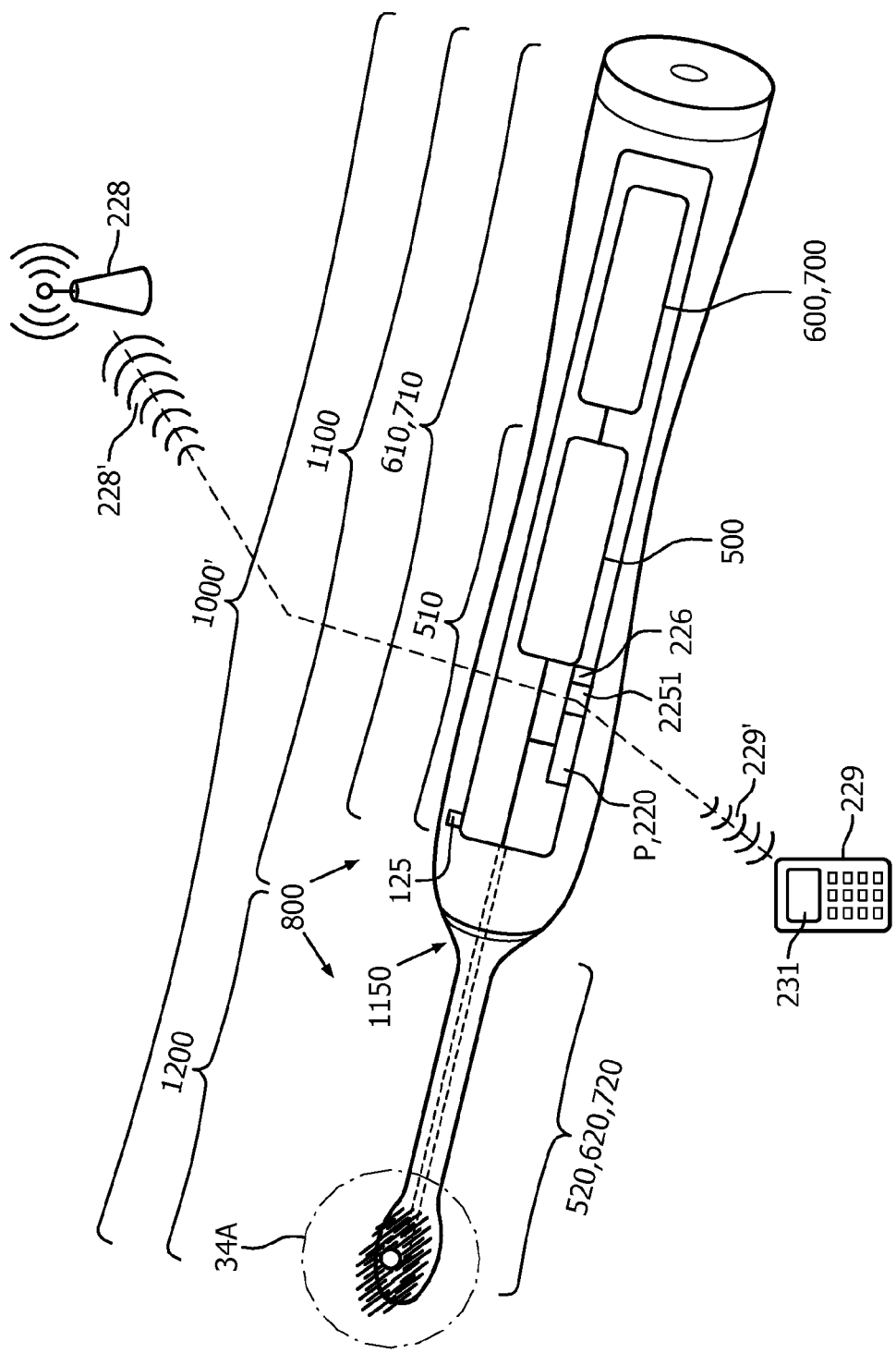
FIG. 34 illustrates an alternate embodiment of the dental apparatus of FIG. 10 wherein a stream probe for plaque detection and an optical detector for gum detection are incorporated into a dental apparatus such as the electric toothbrush of FIG. 33 in accordance with one exemplary embodiment of the present disclosure.

FIG. 34 illustrates an alternate embodiment of the detection apparatus or instrument 200 of FIG. 10, generic composite detection apparatus or instrument 1000 of FIG. 30 or detection apparatus or instrument 1000a of FIG. 31 or detection apparatus or instrument 1000b of FIG. 32 wherein a stream probe for plaque detection and an optical detector for gum detection are incorporated into a dental apparatus such as the electric toothbrush of FIG. 33 in accordance with one exemplary embodiment of the present disclosure.

For simplicity and to illustrate the broad applicability of the embodiments of the present disclosure, the terminology and nomenclature of the generic composite detection apparatus 1000 of FIG. 30 will be applied to the description of vibrating electric tooth brush 1000' of FIG. 34. More particularly, vibrating electric tooth brush 1000' includes proximal body portion 1100 and distal oral insertion portion 1200 which is illustrated in detail in FIG. 33. The distal oral insertion portion 1200 may be coupled to the proximal body portion 1100 via a combined coupler 1150 that includes the mechanical connection 505 and the transmitting coupler 605 and receiving coupler 705. The distal oral insertion portion 1200 includes the distal probe portion 520 and the distal optical gum detector transmission portion 620 and the distal optical gum detector reception portion 720.

The proximal body portion 1100 includes the proximal stream probe portion 510 and the proximal optical gum detector transmission portion 610 and the proximal optical gum detector reception portion 710. Upon detecting plaque by the stream probe 500 and the controller 2251 confirming the presence of plaque by the optical gum detector 800 via the detection electronics 220, the detection apparatus 1000' may again signal to the user to continue brushing in the particular location in a similar manner as described above with respect to FIG. 10.

Through combined coupler 1150, the light is transferred from the proximal optical gum detector transmission portion 610 to the removable brush or distal oral insertion portion 1200 and the light is delivered via distal optical gum detector portion 620 and optical fibre 6201 in FIG. 33 at a position close to the distal probe portion 520 of the stream probe 500. Reflected light is captured by second fibre 7201 in FIG. 33 in distal optical gum detector reception portion 720 and, transferred to proximal optical gum detector reception portion 710 (e.g., the handle), where the light impacts detector 712 and the data is processed to judge if gum or teeth are present at the measurement location.

Figure 34A:
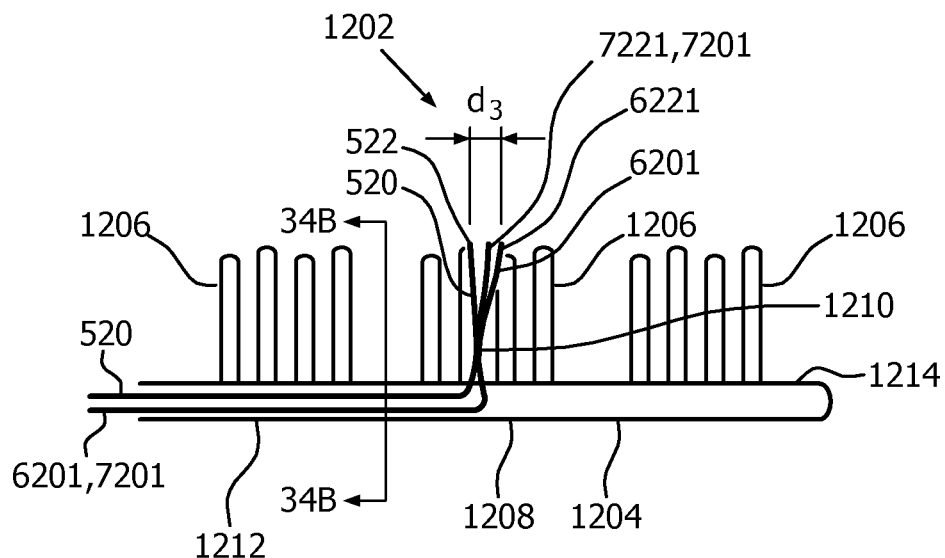
FIG. 34A is a detailed view of the circled portion of the dental apparatus of FIG. 34 illustrating a connection between the stream probe and the optical fibres of FIG. 33 within the bristles of the brush of the dental apparatus.

FIG. 34A is a detailed view of the circled portion of the dental apparatus 1000' of FIG. 34 illustrating a connection 1210 between the stream probe and the optical fibres 6201 and 7201 of FIG. 33 within the bristles 1206 of the brush 1204 of the dental apparatus 1000'. The connection 1210 preferentially maintains the distal optical gum detector transmission portion 620 and distal tip 622 and distal optical gum detector reception portion 720 and distal tip 722 in proximity to the distal stream probe portion 520 and distal tip 522 by partially connecting the distal optical gum detector transmission portion 620, the distal stream probe portion 520, and the distal optical gum detector reception portion 720 to each other at the beginning of the vertical rise of each portion above bristle support member 1208. The distal tips 622 and 722 are thus maintained within a distance d3 from the distal tip 522 of the distal stream probe portion 520 of less than or equal to about 1 millimeter (mm) total distance from one another. Also this positioning allows flexibility of the tips to provide greater comfort to the user or the subject while the detection apparatus 1000' is in operation.

Figure 34B:
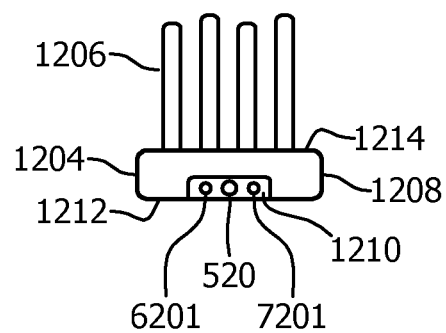
FIG. 34B is a cross-sectional view taken along section line 34B-34B of FIG. 34A illustrating one exemplary embodiment for routing of the stream probe and the optical fibres in the bristle support member of the brush of the dental apparatus of FIGS. 33, 34 and 34A.

FIG. 34B is a cross-sectional view taken along section line 34B-34B of FIG. 34A illustrating one exemplary embodiment for routing of the distal stream probe portion 520 and the distal transmitting optical fibre 6201 and the distal receiving optical fibre 7201 in the bristle support member 1208 of the brush of the dental detection apparatus 1000' of FIGS. 33, 34 and 34A. The distal transmitting optical fibre 6201 and the distal receiving optical fibre 7201 may be routed in a channel 1210 formed in the bristle support member 1208 on surface 1212 that is opposite to surface 1214 of the bristle support member 1208 into which the bristles 1206 are embedded. This configuration allows the user to visually confirm operation of the distal transmitting optical fibre 6201 and the distal receiving optical fibre 7201.

Figure 35:
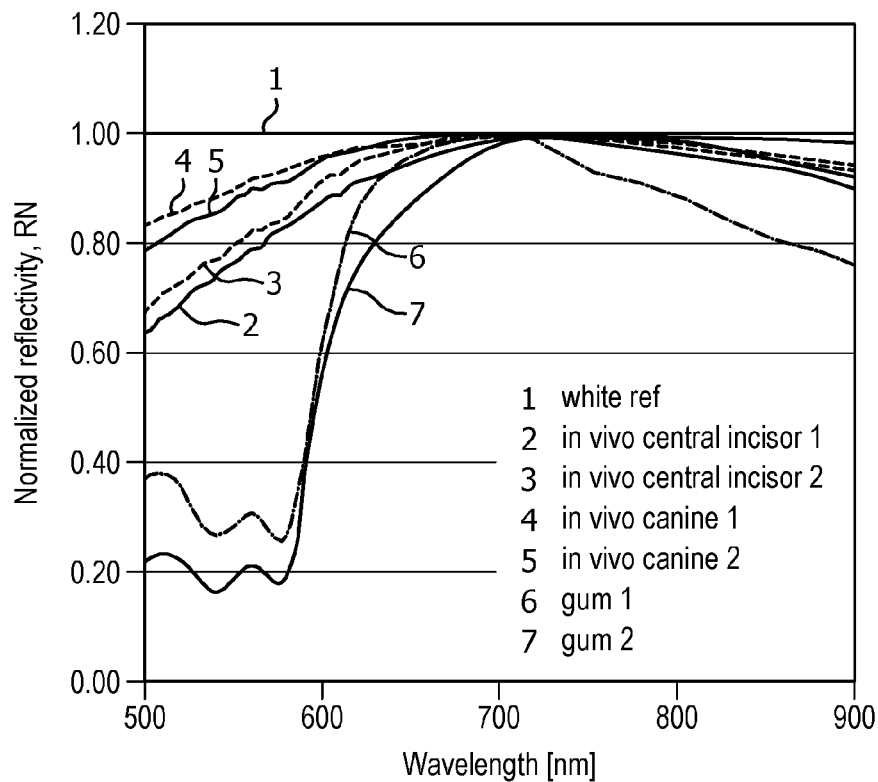
FIG. 35 illustrates a graphical plot of experimental measurements of the reflectivity of gum and teeth as a function of spectral wavelength.

FIG. 35 illustrates a graphical plot of experimental measurements of the reflectivity of gum and teeth as a function of spectral wavelength. The vertical axis represents normalized reflectivity RN ranging from 0.00 to 1.00. The horizontal axis represents the wavelength and is used to choose first wavelength $\lambda 1$ and second light beam at a second wavelength $\lambda 2$ of the light beam in nanometers (nm). The normalization of the reflectivity is with respect to a white tooth having a constant normalized reflectivity of 1.0 as represented by plot 1. Plots 2 and 3 represent the normalized reflectivity of an in vivo central incisor 1 and in vivo central incisor 2, respectively, with respect to wavelength. Plots 4 and 5 represent the normalized reflectivity of an in vivo canine 1 and in vivo canine 2, respectively, with respect to wavelength. Plots 6 and 7 represent the normalized reflectivity of gum 1 and gum 2, respectively, with respect to wavelength.

From these measurements, it is concluded that at wavelengths around 600 nm a clear distinction can be made between teeth, having a shallow behavior as a function of wavelength, and gum, showing a steep slope around this wavelength. Therefore, it is concluded that wavelengths around 600 nm are useful for the gum detection. For example, wavelengths of 570 and 660 nm are widely available for low cost and the ratio R570/R660 shows good contrast between teeth and gum. It is believed to be beneficial to use wavelengths relatively close to each other, because the wavelength dependent scattering behavior (from tooth, gum and toothpaste) results in less variability when the wavelengths are close to each other. For this reason also yellow light-emitting diodes (LEDs ~590 nm) and orange/red (640 nm) may be used. The yellow LED has as a further advantage over the green (570 nm) LED that the efficiency is better, yielding a better signal-to-noise ratio (SNR).

Figure 36:
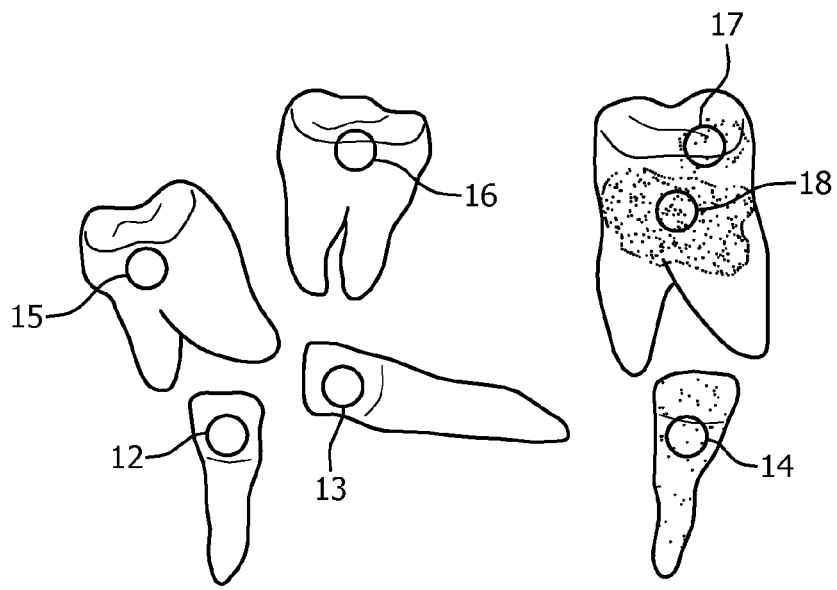
FIG. 36 illustrates white, yellow and seriously stained teeth for which plaque and gum detection measurements were experimentally determined in the circled locations.
Figure 37:
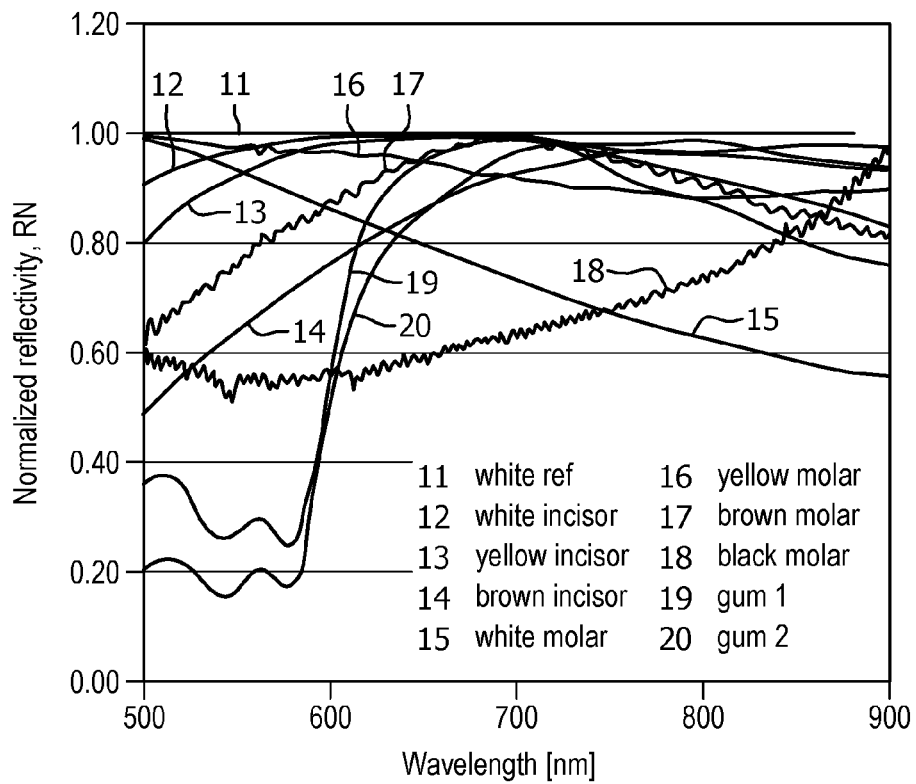
FIG. 37 illustrates a graphical plot of the experimental measurements for the plaque and gum detection measurements for the teeth illustrated in FIG. 36.

FIG. 36 illustrates white, yellow and seriously stained teeth for which plaque and gum detection measurements were experimentally determined in the circled locations. FIG. 37 illustrates a graphical plot of the experimental measurements for the plaque and gum detection measurements for the teeth illustrated in FIG. 36.

More particularly, FIG. 37 illustrates a graphical plot of experimental measurements of the reflectivity of gum and teeth as a function of spectral wavelength and degree of staining for the while molar 15, the yellow molar 16, the brown molar 17 and the black molar 18 that are circled in FIG. 36 and white incisor 12, the yellow incisor 13 and the brown incisor 14 that are similarly circled in FIG. 36. The vertical axis represents normalized reflectivity RN ranging from 0.00 to 1.00. The horizontal axis represents the (first wavelength $\lambda 1$ and second light beam at a second wavelength $\lambda 2$) of the light beam in nanometers (nm). The normalization of the reflectivity is with respect to a white tooth having a constant normalized reflectivity of 1.0 as represented by plot 11. Plots 12, 13 and 14 represent the normalized reflectivity of a white incisor 12, a yellow incisor 13 and a brown incisor 14, respectively, with respect to wavelength. Plots 15, 16, 17 and 18 represent the normalized reflectivity of a white molar 15, a yellow molar 16, a brown molar 17 and a black molar 18, respectively, with respect to wavelength. Plots 19 and 20 represent the normalized reflectivity of gum 1 and gum 2, respectively, with respect to wavelength.

Figure 38:
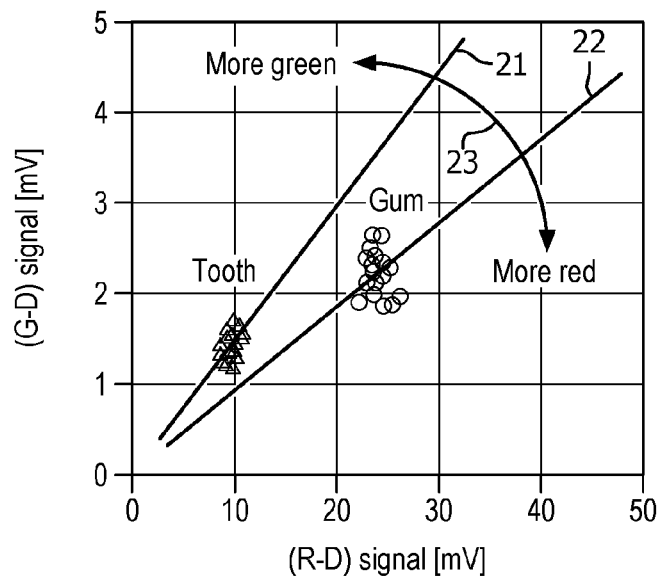
FIG. 38 illustrates a graphical plot of red and green signals measured on tooth and gum.

FIG. 38 illustrates a graphical plot of red and green signals measured on tooth and gum. The vertical axis represents a (G-D) signal in millivolts (mV) ranging from 0 to 5 mV while the horizontal axis represents an (R-D) signal in millivolts (mV) ranging from 0 to 50 mV. More particularly, the measurement results are presented for tooth 21 and gum 22 (multiple measurements on about the same position) where R-D and G-D are the red and green signals corrected by the dark signal level. using a pen with three fibers (570 nm LED light, 660 nm LED light and to detector), Though the measurements show some spread, (ascribed to the fact that the spots from the green and red LEDs are laterally displaced with respect to each other and noise occurs on the green channel 21 because of low light intensities), the distinction between teeth and gum is clearly visible as indicated by the double arrow 23 which indicates the direction of more or increasing green and more or increasing red.

Figure 39:
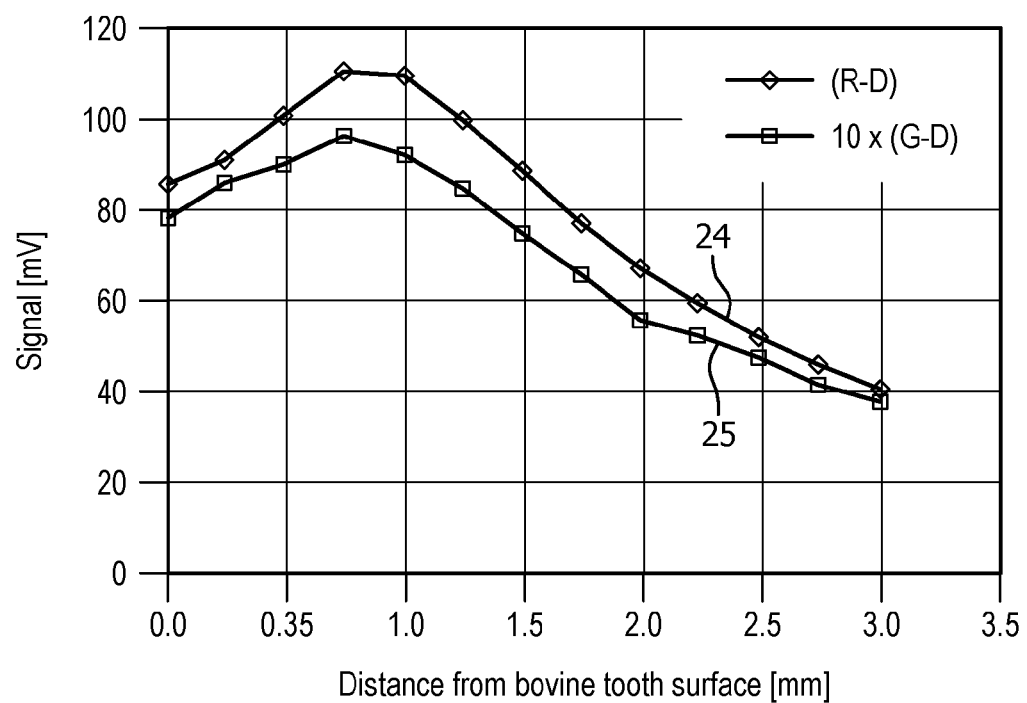
FIG. 39 illustrates a graphical plot the signal levels for plaque and gum detection as a function of distance of the probe from a bovine tooth.

FIG. 39 illustrates a graphical plot of the signal levels for plaque (R-D) 24 and gum (G-D) 25 detection in millivolts (mV) as a function of distance in millimeters (mm) of the probe from a bovine tooth. Best signals are obtained at a probe location slightly away from the tooth surface, around 0.8 mm, because the light may more easily enter the fiber to the detector as compared to a contact position with the tooth. Optimum working distance in a practical situation with toothpaste is in between the maximum signal point of around 0.8 mm and 0 mm. By controlling the fibre ends in position with respect to the bristle hair ends, this parameter can be optimized. However, it is noted that in a practical toothpaste environment light will be lost by scattering in the toothpaste, which causes the peak signal from the teeth/gum to shift to the left in FIG. 39.

Figure 40:
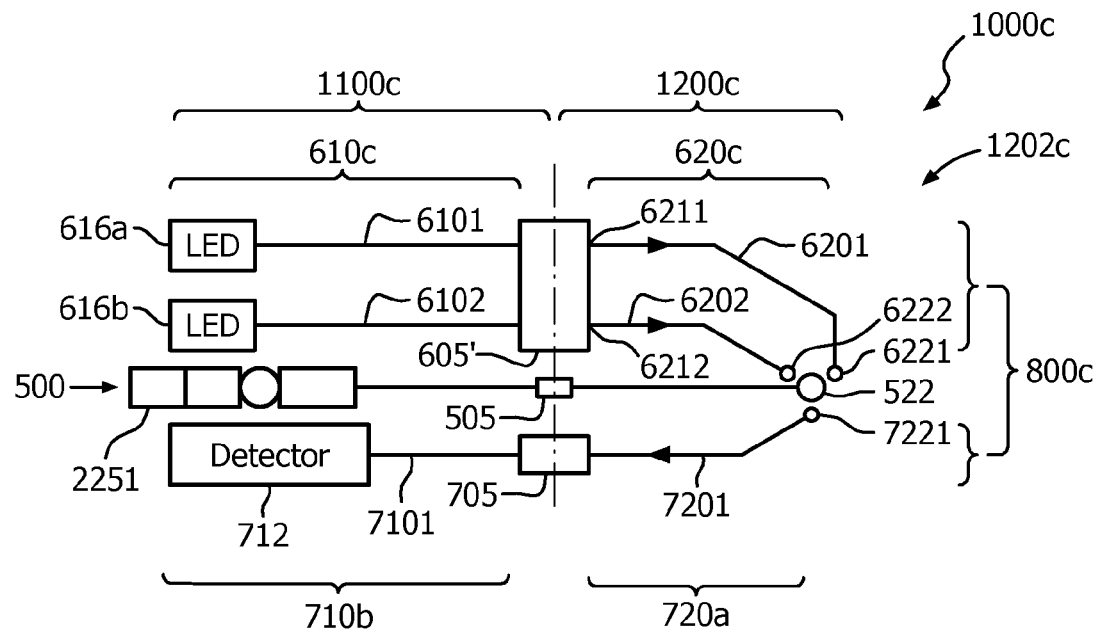
FIG. 40 illustrates another particular embodiment of a detection apparatus of FIG. 30 according to the present disclosure wherein a distal oral insertion portion includes first and second optical transmitting fibres without an optical combiner on the proximal body portion and an optical receiving fibre feeds a single optical detector.

FIG. 40 illustrates another particular embodiment of a detection apparatus of FIG. 30 according to the present disclosure wherein a distal oral insertion portion includes first and second optical transmitting fibres without an optical combiner on the proximal body portion and an optical receiving fibre feeds a single optical detector.

More particularly, referring to FIG. 40 in conjunction with the composite detection apparatus 1000 described with respect to FIG. 30, and the detection apparatus 1000a described with respect to FIG. 31, there is disclosed an exemplary embodiment of the present disclosure wherein detection apparatus 1000c includes composite plaque detection apparatus 500, as described above with respect to FIG. 30, and optical gum detector 800c each disposed partially on distal oral insertion portion 1200c. In contrast to FIG. 31, distal oral insertion portion 1200c includes distal optical detector transmitting portion 620c wherein a first distal transmitting optical fibre 6201 defines a proximal end 6211 and a distal tip 6221 extending to the vicinity of distal end 1202c of distal oral insertion portion 1200c and, in addition, a second distal transmitting optical fibre 6202 defines a proximal end 6212 and a distal tip 6222 also extending to the vicinity of distal end 1202c of distal oral insertion portion 1200c. In the same manner as in FIG. 31, distal optical detector receiving portion 720a includes distal receiving optical fibre 7201 having distal tip 7221 extending from the vicinity of distal end 1202c. Distal oral insertion portion 1200c also further includes distal probe portion 520 defining distal tip 522 having open port 526. Proximal end 6211 of first distal transmitting optical fibre 6201 and proximal end 6212 of the second distal transmitting optical fibre 6202 may be coupled to a common optical transmitting coupler 605' that defines proximal ends 6211 and 6212.

Detection apparatus 1000c further includes proximal body portion 1100c that includes proximal optical gum detector transmission portion 610c. In contrast to FIG. 31, the proximal optical gum detector transmission portion 610c includes first proximal transmitting optical fibre 6101 that may be optically coupled to the distal transmitting optical fibre 6201 via transmitting coupler 605' but also includes a second proximal transmitting optical fibre 6102 that may be optically coupled to the second distal transmitting optical fibre 6202 via transmitting coupler 605'. In contrast to FIG. 31, the proximal optical gum detector transmission portion 610c does not include optical combiner 6121.

Rather, proximal optical gum detector transmission portion 610c further includes a first light source 616a, such as a light emitting diode, and a second light source 616b, also such as a light emitting diode. The first light source 616a is optically coupled to the first proximal transmitting optical fibre 6101 to transmit light from the first light source 616a to the first distal transmitting optical detector fibre 6201 in the distal optical gum detector transmission portion 620c in the distal oral insertion portion 1200c. Additionally, the second light source 616b is optically coupled to the second proximal transmitting optical fibre 6102 to transmit light from the second light source 616b to the second distal transmitting optical detector fibre 6202 in the distal optical gum detector transmission portion 620c in the distal oral insertion portion 1200c. Therefore, rather than the first proximal transmitting optical fibre 6101 and the second proximal transmitting optical fibre 6102 being coupled to a combiner, each fibre is routed independently to the distal oral insertion portion 1200c and may be coupled to the common transmitting coupler 605'.

In the same manner as FIG. 31, the distal oral insertion portion 1200c includes distal optical gum detector reception portion 720a wherein first distal receiving optical fibre 7201 may be optically coupled to the receiving coupler 705.

Proximal optical gum detector reception portion 710a further includes first proximal receiving optical fibre 7101 that may be optically coupled to the first distal receiving optical fibre 7201 via the receiving coupler 705. The proximal optical gum detector reception portion 710a further includes optical detector 712 that is optically coupled to the first proximal receiving optical fibre 7101.

Process controller 2251 signals first light source 616a to emit a light beam at a first wavelength $\lambda 1$ and signals second light source 616b to emit a light beam at a second wavelength $\lambda 2$ where the two light beams are transmitted such that the light beams at two different wavelengths are transmitted intermittently and alternately at the two different wavelengths, one light beam to the distal tip 6221 via the first distal transmitting optical fibre 6201 and the second light beam to the distal tip 6222 via the second distal transmitting optical fibre 6202. Light emitted from the distal tips 6221 and 6222 is transmitted to the distal tip 7221 of the first distal receiving optical fibre 7201 to optical detector 712 via optical coupler 705. As explained in more detail above with respect to FIGS. 35-39, in the event that plaque detection apparatus 500 signals to the process controller 2251 that plaque has been detected, detection apparatus 1000c distinguishes between white teeth and red gum by the process controller 2251 measuring the reflectivity ratio R resulting from the two wavelengths $\lambda 1$ and $\lambda 2$. Again, the reflectivity ratio R is defined as the ratio of observed reflection levels for the two wavelengths $\lambda 1$ and $\lambda 2$:

The reflectivity ratio R is determined, where a ratio above a certain discrimination level corresponds with teeth and a ratio below this level corresponds with gum. The basis for the detection method is that a measure for the reflectance of the gum/tooth is obtained using at least two wavelengths, with two wavelengths as the preference. From the two central wavelengths, one is dominantly below 600 nm and the other is dominantly above 600 nm. The ratio of observed reflection levels for the two wavelengths $\lambda low/\lambda high$ is determined, where a ratio above a certain discrimination level corresponds with teeth and a ratio below this level corresponds with gum.

Upon confirmation by the process controller 2251 that plaque has been detected, the process controller 2251 initiates the alarm or guidance device 226 or the other methods of feedback to the user that have been described above with respect to FIG. 10 and FIG. 22 to continue brushing in the particular area.

Figure 41:
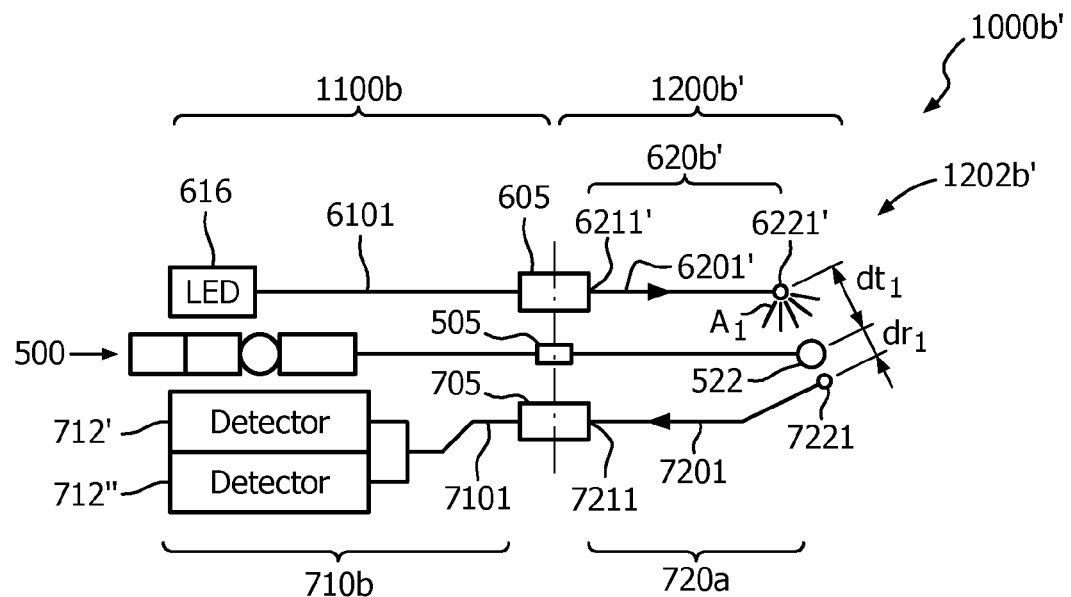
FIG. 41 illustrates another particular embodiment of the detection apparatus of FIG. 32 according to the present disclosure wherein the distal optical transmitting fibre has a shorter length compared to the distal optical receiving fibre to establish a broad illumination area.

FIG. 41 illustrates another particular embodiment of the detection apparatus of FIG. 32 according to the present disclosure wherein the distal optical transmitting fibre has a shorter length compared to the distal optical receiving fibre to establish a broad illumination area.

More particularly, detection apparatus 1000b' is identical to detection apparatus 1000b described above with respect to FIG. 32 which includes distal optical detector receiving portion 720a including first distal receiving optical fibre 7201 having a distal tip 7221 that defines a distance dr1 with respect to the distal tip 522 of the distal probe portion 520.

However, distal optical gum detector transmission portion 620b' in distal oral insertion portion 1200b' is configured such that distance dr1 with respect to the distal tip 522 of the distal probe portion 520 is less than distance dt1 defined by the distal tip 6221' of the first distal transmitting optical fibre 6201' with respect to the distal tip 522 of the distal probe portion 520 so as to define a broad optical illumination area A1.

The plaque detection and gum detection and signalling by controller 2251 to the user are the same as described previously except that the broad illumination area A1 increases the signal from the distal tip 6221' of the distal transmitting optical fibre 6201' to the distal tip 7221 of the distal receiving optical fibre 7201 without both the transmitting path and the receiving path suffering losses due to the presence of toothpaste.

Figure 42:
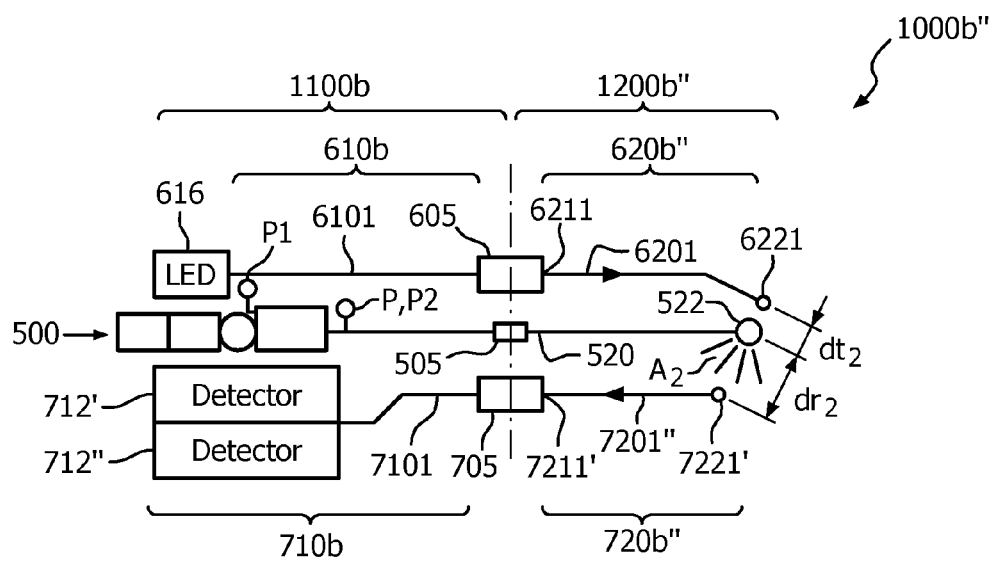
FIG. 42 illustrates another particular embodiment of the detection apparatus of FIG. 32 according to the present disclosure wherein the distal optical receiving fibre has a shorter length compared to the distal optical transmitting fibre to establish a broad collection area.

FIG. 42 illustrates another particular embodiment of the detection apparatus of FIG. 32 according to the present disclosure wherein the distal optical receiving fibre has a shorter length compared to the distal optical transmitting fibre to establish a broad collection area.

More particularly, detection apparatus 1000b" is identical to detection apparatus 1000b described above with respect to FIG. 32 that includes distal optical detector transmitting portion 1200b" including first distal receiving optical fibre 6201 having a distal tip 6221 that defines a distance dt2 with respect to the distal tip 522 of the distal probe portion 520.

However, distal optical gum detector transmission portion 620b" in distal oral insertion portion 1200b" is configured such that distal tip 6221 of first distal transmitting optical fibre 6201' defines a distance dt2 with respect to the distal tip 522 of the distal probe portion 520 that is less than a distance dr2 defined by the distal tip 7221' of the first distal receiving optical fibre 7201' with respect to the distal tip 522 of the distal probe portion 520 so as to define a broad optical collection area A2.

Again, the plaque detection and gum detection and signaling by controller 2251 to the user are the same as described previously but except that in comparison to the broad illumination area A1 of detection apparatus 1000b' of FIG. 41, it is now the broad collection area A2 that increases the signal from the distal tip 6221 of the distal transmitting optical fibre 6201 to the distal tip 7221' of the distal receiving optical fibre 7201' without both the transmitting path and the receiving path suffering losses due to the presence of toothpaste.

Figure 43:
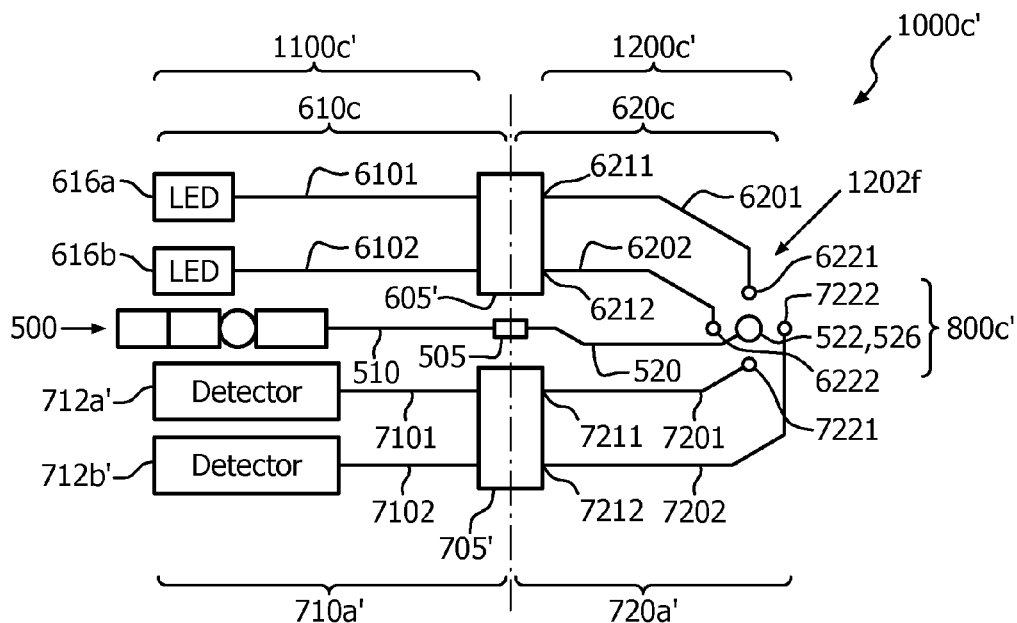
FIG. 43 illustrates another particular embodiment of the detection apparatus of FIG. 40 according to the present disclosure wherein a second optical receiving fibre feeds a second optical detector.

FIG. 43 illustrates another particular embodiment of the detection apparatus of FIG. 40 according to the present disclosure wherein a second optical receiving fibre feeds a second optical detector.

More particularly, referring to FIG. 43 in conjunction with FIG. 40 and the composite detection apparatus 1000 described with respect to FIG. 30, there is disclosed an exemplary embodiment of the present disclosure wherein detection apparatus 1000c' includes composite plaque detection apparatus 500, as described above with respect to FIG. 30, and optical gum detector 800c' each disposed partially on distal oral insertion portion 1200c'. In the same manner as illustrated in FIG. 40, distal oral insertion portion 1200c' includes distal optical detector transmitting portion 620c wherein first distal transmitting optical fibre 6201 has distal tip 6221 and second distal transmitting optical fibre 6202 has distal tip 6222, each distal tip extending to the vicinity of distal end 1202c' distal oral insertion portion 1200c'.

Also in the same manner as illustrated in FIG. 40, distal oral insertion portion 1200c' includes distal optical detector receiving portion 720a wherein distal receiving optical fibre 7201 has distal tip 7221 extending from the vicinity of distal end 1202c' distal oral insertion portion 1200c'. However, distal optical detector receiving portion 720a' further includes second distal receiving optical fibre 7202 having distal tip 7222.

In the same manner as in FIG. 40, distal oral insertion portion 1200c' further includes distal probe portion 520 defining distal tip 522 having open port 526. Proximal end 7211 of the first distal receiving optical fibre 7201 and proximal end 7212 of the second distal receiving optical fibre 7202 may be coupled to a common optical receiving coupler 705'.

Detection apparatus 1000c further includes proximal body portion 1100c' that includes proximal optical gum detector transmission portion 610c as described above with respect to FIG. 40. In contrast to FIG. 40, proximal optical gum detector reception portion 710a' includes first proximal receiving optical fibre 7101 that may be optically coupled to first distal receiving optical fibre 7201 via transmitting coupler 705' but also includes a second proximal receiving optical fibre 7102 that may be optically coupled to the second distal receiving optical fibre 7201 via receiving coupler 705'.

In addition, proximal optical gum detector reception portion 710a' further includes a first light detector 712a' and a second light detector 712b'. The first light detector 712a' is optically coupled to the first proximal receiving optical fibre 7101 to receive light from the distal tip 7221 of the first distal receiving optical fibre 7201. In addition, the second light detector 712b' is optically coupled to the second proximal receiving optical fibre 7102 to receive light from the distal tip 7222 of the second distal receiving optical fibre 7202 in the optical gum detector reception portion 720a of the distal oral insertion portion 1200c'. Distal tips 7221 and 7222 also extend from the vicinity of distal end 1202c' distal oral insertion portion 1200c'.

Additionally, in the same manner as illustrated in FIG. 40, the second light source 616b is optically coupled to the second proximal transmitting optical fibre 6102 to transmit light from the second light source 616b to the second distal transmitting optical detector fibre 6202 in the distal optical gum detector transmission portion 620c in the distal oral insertion portion 1200c. Therefore, rather than the first proximal transmitting optical fibre 6101 and the second proximal transmitting optical fibre 6102 being coupled to a combiner, each fibre is routed independently to the distal oral insertion portion 1200c and may be coupled to the common transmitting coupler 605'.

Again, the plaque detection and signaling by controller 2251 to the user are the same as described previously.

Figure 44:
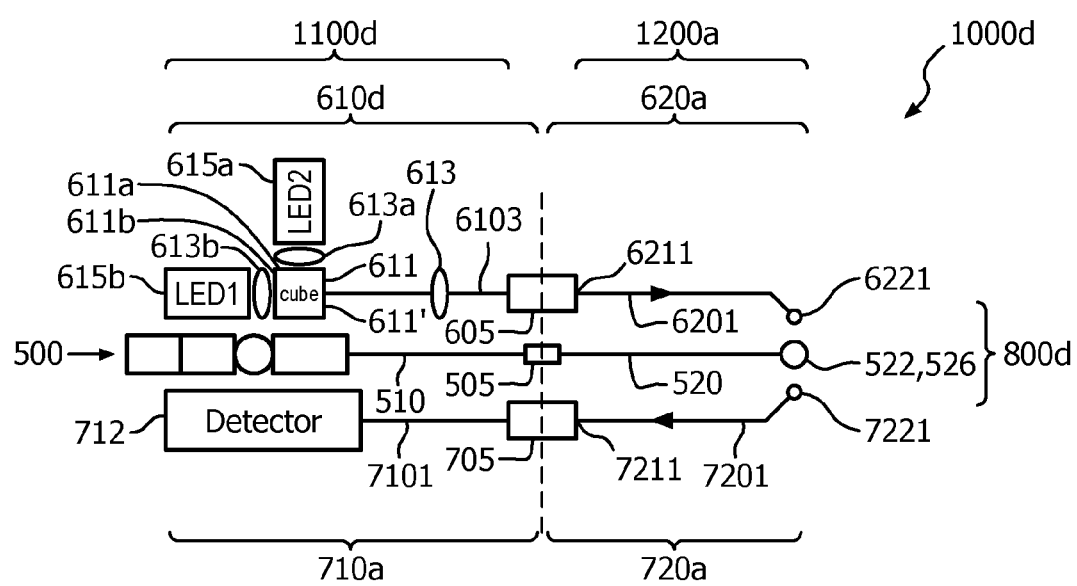
FIG. 44 illustrates another particular embodiment of the detection apparatus of FIG. 31 according to the present disclosure wherein the proximal body portion includes two light sources transmitting light to the proximal optical transmitting fibre through lenses and a dichroic cube.

FIG. 44 illustrates another particular exemplary embodiment of the detection apparatus of FIG. 31 according to the present disclosure wherein the proximal body portion includes two light sources transmitting light to the proximal optical transmitting fibre through lenses and a dichroic cube.

More particularly, referring to FIG. 44 in conjunction with FIG. 31 and the composite detection apparatus 1000 described with respect to FIG. 30, there is disclosed another exemplary embodiment of the present disclosure wherein detection apparatus 1000d includes composite plaque detection apparatus 500, as described above with respect to FIG. 30, and optical gum detector 800d each disposed partially on distal oral insertion portion 1200a. In the same manner as illustrated in FIG. 31, distal oral insertion portion 1200a includes distal optical detector transmitting portion 620a wherein first distal transmitting optical fibre 6201 has distal tip 6221.

Also in the same manner as illustrated in FIG. 31, distal oral insertion portion 1200a includes distal optical detector receiving portion 720a wherein distal receiving optical fibre 7201 may be optically coupled to the receiving coupler 705.

Also in the same manner as illustrated in FIG. 31, proximal body portion 1100d includes proximal optical gum detector reception portion 710a wherein first proximal receiving optical fibre 7101 may be optically coupled to the first distal receiving optical fibre 7201 via the receiving coupler 705. The proximal optical gum detector reception portion 710a further includes an optical detector 712 that is optically coupled to the first proximal receiving optical fibre 7101.

However, detection apparatus 1000d differs from the detection apparatus 1000a illustrated in FIG. 31 in that proximal optical gum detector transmission portion 610d includes a dichroic cube 611 defining a light transmitting surface 611' and optically coupled to a proximal transmitting fibre 6103 via an optical lens 613 disposed to focus light emitted from the light transmitting surface 611' of the dichroic cube 611 through the first proximal transmitting fibre 6103. The dichroic cube 611 further includes a first light receiving surface 611a and a second light receiving surface 611b.

The proximal optical gum detector transmission portion 610d further includes a first light emitting diode 615a and another optical lens 611a disposed between the first light emitting diode 615a and the first light receiving surface 611a to focus light emitted from the first light emitting diode 615a into the first light receiving surface 611a. The proximal optical gum detector transmission portion 610d further includes a second light emitting diode 615b and yet another optical lens 611b disposed between the second light emitting diode 615b and the second light receiving surface 611b to focus light emitted from the second light emitting diode 615b into the second light receiving surface 611b.

Yet again, the plaque detection and signaling by controller 2251 to the user are the same as described previously.

Figure 45:
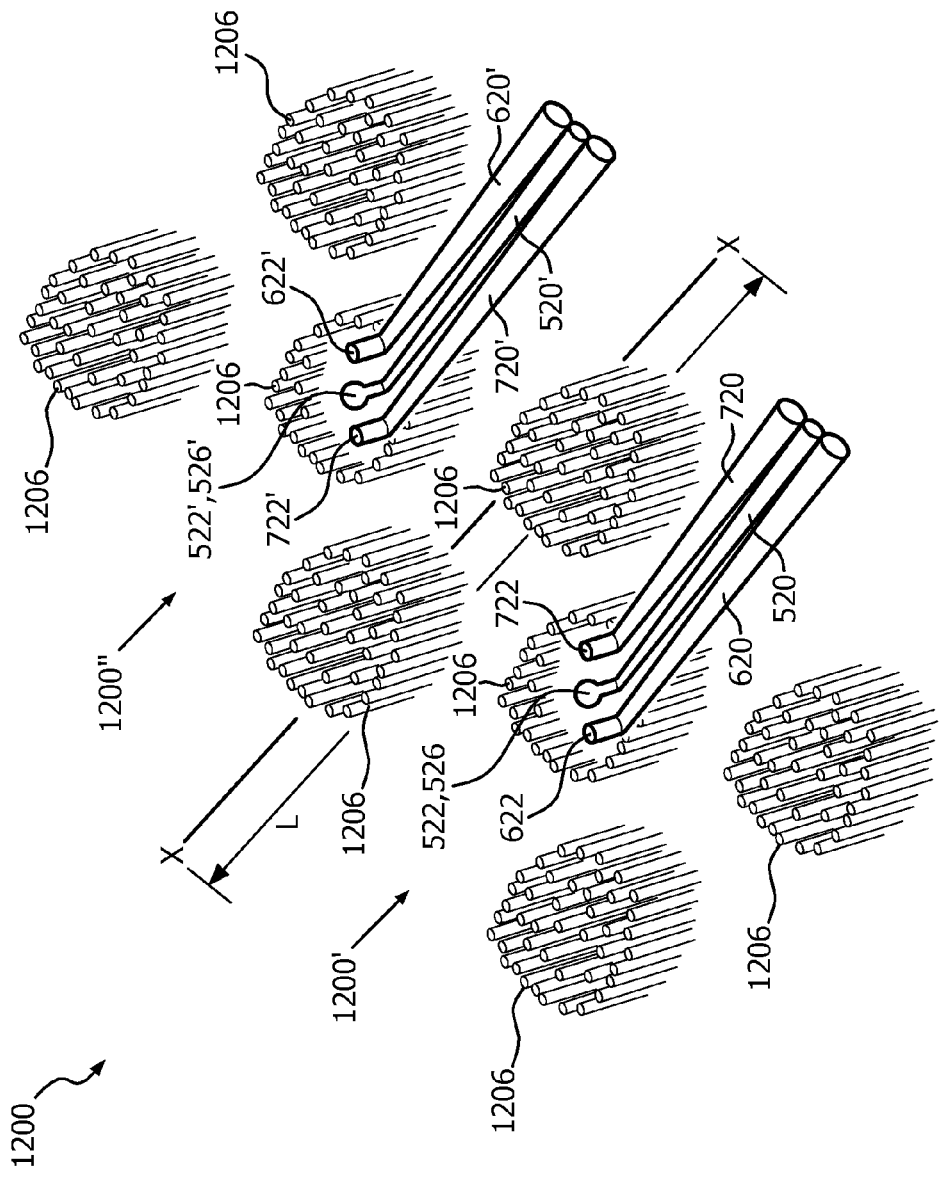
FIG. 45 illustrates a distal oral insertion portion of a detection apparatus according to one exemplary embodiment of the present disclosure wherein the distal oral insertion portion defines a longitudinal centerline along its length to define a first side and a second side wherein a first detection apparatus that includes a stream probe for plaque detection and an optical detector for gum detection is disposed on the first side and a second detection apparatus that includes a stream probe for plaque detection and an optical detector for gum detection is disposed on the second side.

FIG. 45 illustrates a distal oral insertion portion of a detection apparatus according to one exemplary embodiment of the present disclosure wherein the distal oral insertion portion defines a longitudinal centerline along its length to define a first side and a second side wherein a first detection apparatus that includes a stream probe for plaque detection and an optical detector for gum detection is disposed on the first side and a second detection apparatus that includes a stream probe for plaque detection and an optical detector for gum detection is disposed on the second side.

More particularly, as illustrated in FIG. 45, the distal oral insertion portion 1200 of the generic composite detection apparatus 1000 of FIG. 30 defines a longitudinal centerline X-X along length L of the distal oral insertion portion 1200 to define a first side 1200' of the distal oral insertion portion 1200 and a second side 1200" of the distal oral insertion portion 1200. The distal probe portion 520 is a first distal probe portion, the distal optical gum detector transmission portion 620 is a first distal optical gum detector portion, and the distal optical gum detector reception portion 720 is a first distal optical gum detector reception portion and each is disposed on the first side 1200' of the distal oral insertion portion 1200 defined by the longitudinal centerline X-X.

The distal oral insertion portion 1200 on second side 1200" further includes a second distal probe portion 520' of a second stream probe 500' that is configured to be immersed in the first fluid 11. The second distal probe portion 520' also defines a distal tip 522' having an open port 526' to enable passage of the second fluid 30, 35 therethrough. Again, the open port 526' of the distal tip 522' of the second distal probe portion 520' also has a cross-sectional area sufficient and a shape configured to detect substance 116 that may be present on surface 31, 33.

A second distal optical gum detector transmission portion 620' on second side 1200" defines a proximal end 621' and a distal tip 622'. The distal tip 622' of the second distal optical gum detector transmission portion 620' extends to the vicinity of the distal end 1202 of the distal oral insertion portion 1200.

A second distal optical gum detector reception portion 720' on second side 1200" defines a proximal end 721 and a distal tip 722'. The distal tip 722" of the second distal optical gum detector reception portion 720' extends to the vicinity of the distal end 1202 of the distal oral insertion portion 1200.

The detection apparatus 1000 is configured such that passage of the second fluid 30, 35 through the distal tip 522 of the first distal probe portion 520) enables detection of a substance 116 that may be present on the surface 31, 33 based on measurement of a signal correlating a substance 116 at least partially obstructing the passage of fluid 30, 35 through the open port 526 of the distal tip 522 of the distal probe portion 520. The detection apparatus 1000 is also configured such that the distal optical gum detector transmission portion 620 and the distal optical gum detector reception portion 720 are in a position to transmit and to receive, respectively, an optical signal that upon transmission of the optical signal and reception of the optical signal by controller 2251, which enables the controller 2251 to determine if the open port 526 of the distal tip 522 of the distal probe portion 520 is in contact with a substance 116 at least partially obstructing the passage of fluid 30, 35 through the open port 526 and not in contact with the gums of a subject or of a user of the detection apparatus 1000. The second distal probe portion 520' is positioned on the gums of a subject or of a user, respectively as part of guidance to the user to keep one on the gum, while the other one, i.e., first distal probe portion 520, is on the teeth, to ensure effective gum line brushing.

The detection apparatus 1000 is configured such that passage of the second fluid 30, 35 through the distal tip 522 of the first distal probe portion 520) enables detection of a substance 116 that may be present on the surface 31, 33 based on measurement of a signal correlating a substance 116 at least partially obstructing the passage of fluid 30, 35 through the open port 526 of the distal tip 522 of the distal probe portion 520. The detection apparatus 1000 is also configured such that the distal optical gum detector transmission portion 620 and the distal optical gum detector reception portion 720 are in a position to transmit and to receive, respectively, an optical signal that upon transmission of the optical signal and reception of the optical signal by controller 2251, which enables the controller 2251 to determine if the open port 526 of the distal tip 522 of the distal probe portion 520 is in contact with a substance 116 at least partially obstructing the passage of fluid 30, 35 through the open port 526 and not in contact with the gums of a subject or of a user of the detection apparatus 1000. The second distal probe portion 520' is positioned on the gums of a subject or of a user, respectively as part of guidance to the user to keep one on the gum, while the other one, i.e., first distal probe portion 520, is on the teeth, to ensure effective gum line brushing. Depending on where the distal oral insertion portion 1200 (e.g., the brush head) is in the mouth, either the distal probe portion 520, distal optical gum detector transmission portion 620 and distal optical gum detector reception portion 720 of first side 1200' or the distal probe portion 520', distal optical gum detector transmission portion 620' and distal optical gum detector reception portion 720' of second side 1200" will be on the teeth while the other side will be on the gums (depending on whether the user is right-handed or left-handed, whether the upper gums and teeth are being cleansed or the lower gums and teeth are being cleansed or whether the interior surfaces of the teeth and gums are being cleansed or whether the exterior surfaces of the teeth and gums are being cleansed). Thus, when moving about the mouth in a single brushing session, the relative positions of the stream probe on side 1200' and the stream probe on side 1200" on tooth or gums will be reversed periodically. Depending on where the brush head is in the mouth, one or the other will be on teeth or gums. The stream probe on the teeth should have the plaque detection probe, so both stream probes require plaque detection probes even though at any one time only one plaque detection probe is useful. Similarly, the stream probe on the gums should have the optical gum detector probes, even though at any one time only one optical gum detector probe is useful.

Figure 46:
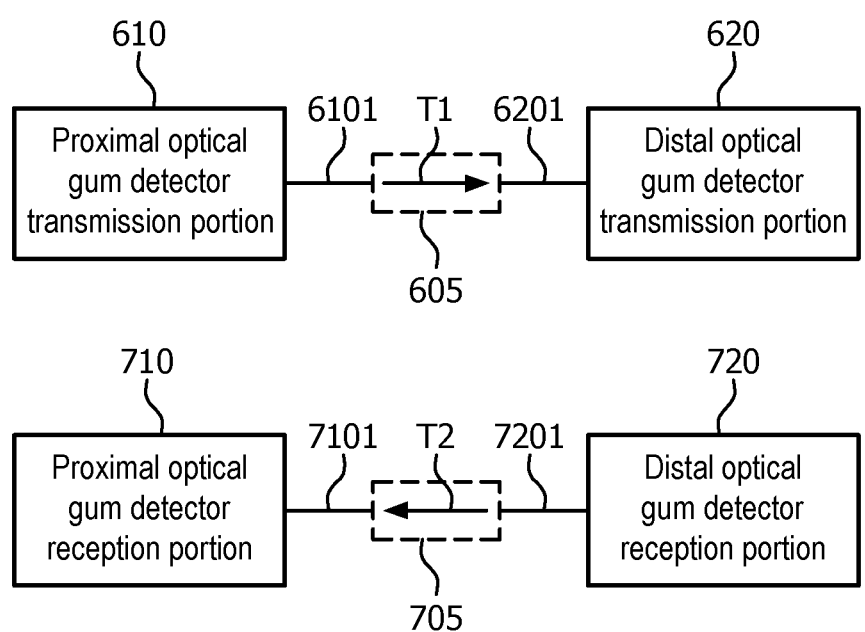
FIG. 46 illustrates optical coupling between the proximal optical gum detector transmission portion and distal optical gum detector transmission portion and between the distal optical gum detector reception portion and proximal optical gum detector reception portion of the detection apparatus of FIG. 30 wherein the coupling is affected by air transfers.

FIG. 46 illustrates optical coupling between the proximal optical gum detector transmission portion and distal optical gum detector transmission portion and between the distal optical gum detector reception portion and proximal optical gum detector reception portion of the detection apparatus of FIG. 30 wherein the coupling is effected by air transfers.

More particularly, FIG. 46 is a simplified partial depiction of the detection apparatus 1000 of FIG. 30 partially combined with, for example, the detection apparatus 1000*a* of FIG. 31. Proximal optical gum detector transmission portion 610 is represented by proximal transmitting optical fibre 6101 which transmits a light beam to distal transmitting optical fibre 6201 representing distal optical gum detector transmission portion 620. Instead of proximal transmitting optical fibre 6101 being optically coupled to distal transmitting optical fibre 6201 via the transmission coupler 605, the optical coupling is effected by an air transfer represented by arrow T1 between proximal transmitting optical fibre 6101 and distal transmitting optical fibre 6201.

Similarly, distal optical gum detector reception portion 720 is represented by distal receiving optical fibre 7201 which transmits a light beam to proximal receiving optical fibre 7101 representing proximal optical gum detector reception portion 710. Instead of distal receiving optical fibre 7201 being optically coupled to proximal receiving optical fibre 7101 via the reception coupler 705, the optical coupling is effected by an air transfer represented by arrow T2 between distal receiving optical fibre 7201 and proximal receiving optical fibre 7101.

The mechanical connection 505 for plaque detection apparatus 500 would remain as shown in FIG. 30.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope of the claims appended hereto.

In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention may be implemented by means of hardware comprising several distinct elements, and/or by means of a suitably programmed processor. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A dental hygiene detection apparatus for detecting the presence of a substance on a surface, the detection apparatus comprising:
   a distal oral insertion portion defining a proximal end and a distal end, the distal oral insertion portion including:
   a stream probe having distal probe portion, the distal probe portion of the stream probe configured to be immersed in a first fluid, the distal probe portion defining a distal tip having an open port to enable passage of a gas therethrough, the open port of the distal tip having a size and shape configured to detect a substance that may be present on a surface,
   a distal optical gum detector transmission portion defining a proximal end and a distal tip, the distal tip of the distal optical gum detector transmission portion extending to the vicinity of the distal end of the distal oral insertion portion; and
   a distal optical gum detector reception portion defining a proximal end and a distal tip, the distal optical gum detector reception portion extending to the vicinity of the distal end of the distal oral insertion portion,
   the apparatus configured such that passage of the gas through the distal tip of the distal probe portion of the stream probe enables detection of a substance that may be present on the surface based on measurement of a stream probe signal correlating a substance at least partially obstructing the passage of fluid through the open port of the distal tip of the distal probe portion of the stream probe, and configured such that the distal optical gum detector transmission portion and the distal optical gum detector reception portion are in a position to transmit and to receive, respectively, an optical signal that upon transmission of the optical signal and reception of the optical signal by a controller, the controller configured to determine, based on the stream probe signal and the optical signal, if the open port of the distal tip of the distal probe portion of the stream probe is in contact with a substance at least partially obstructing the passage of fluid through the open port and not in contact with the gums,
   wherein the optical signal is obtained using at least two wavelengths, with a first wavelength below 600 nm and a second wavelength above 600 nm.

2. The dental hygiene detection apparatus according to claim 1, wherein the distal optical gum detector transmission portion includes a first distal transmitting optical fiber defining a proximal end and a distal tip extending to the vicinity of the distal end of the distal oral insertion portion and
   wherein the distal optical gum detector transmission portion further includes a second distal transmitting optical fiber defining a proximal end and a distal tip, the distal tip of the second distal transmitting optical fiber extending to the vicinity of the distal end of the distal oral insertion portion.

3. The dental hygiene detection apparatus according to claim 1, wherein the distal optical detector transmitting portion comprises a first distal transmitting optical fiber having a distal tip, and
   wherein the distal optical detector receiving portion comprises a first distal receiving optical fiber having a distal tip that defines a distance with respect to the distal tip of the distal probe portion that is less than a distance defined by the distal tip of the first distal transmitting optical fiber with respect to the distal tip of the distal probe portion so as to define a broad optical illumination area.

4. The dental hygiene detection apparatus according to claim 1, wherein the distal optical detector transmitting portion comprises a first distal transmitting optical fiber having a distal tip extending to the vicinity of the distal end of the distal oral insertion portion, and wherein the distal optical detector receiving portion comprises a first distal receiving optical fiber having a distal tip, and wherein the distal tip of the first distal transmitting optical fiber defines a distance with respect to the distal tip of the distal probe portion that is less than a distance defined by the distal tip of the first distal receiving optical fiber with respect to the distal tip of the distal probe portion so as to define a broad optical collection area.

5. The dental hygiene detection apparatus according to claim 1, wherein the distal optical gum detector reception portion includes a first distal receiving optical fiber defining a proximal end and a distal tip, the distal tip of the first distal receiving optical fiber extending from the vicinity of the distal end of the distal oral insertion portion; and a second distal receiving optical fiber defining a proximal end and a distal tip, the second distal receiving optical fiber extending from the vicinity of the distal end of the distal oral insertion portion.

6. The dental hygiene detection apparatus according to claim 1, wherein the distal oral insertion portion defines a longitudinal centerline along the length of the distal oral insertion portion to define a first side of the distal oral insertion portion and a second side of the distal oral insertion portion, wherein the distal probe portion is a first distal probe portion, the distal optical gum detector transmission portion is a first distal optical gum detector portion, and the distal optical gum detector reception portion is a first distal optical gum detector reception portion, each disposed on the first side of the distal oral insertion portion defined by the longitudinal centerline, the distal oral insertion portion further comprising:

a second distal probe portion of a second stream probe configured to be immersed in the first fluid, the second distal probe portion defining a distal tip having an open port to enable passage of the gas therethrough, the open port of the distal tip of the second distal probe portion having a to detect substance that may be present on surface, a second distal optical gum detector transmission portion defining a proximal end and a distal tip, the distal tip of the second distal optical gum detector transmission portion extending to the vicinity of the distal end of the distal oral insertion portion; and a second distal optical gum detector reception portion defining a proximal end and a distal tip, the second distal optical gum detector reception portion extending from the vicinity of the distal end of the distal oral insertion portion, the apparatus configured such that passage of the gas through the distal tip of the first distal probe portion enables detection of a substance that may be present on the surface based on measurement of a signal correlating a substance at least partially obstructing the passage of fluid through the open port of the distal tip of the distal probe portion, and configured such that the distal optical gum detector transmission portion and the distal optical gum detector reception portion are in a position to transmit and to receive, respectively, an optical signal that upon transmission of the optical signal and reception of the optical signal by a controller, enables the controller to determine if the open port of the distal tip of the distal probe portion is in contact with a substance at least partially obstructing the passage of fluid through the open port and not in contact with the gums and wherein the second distal probe portion is positioned on the gums respectively.

7. The dental hygiene detection apparatus according to claim 1, wherein the dental hygiene detection apparatus further comprises a proximal body portion including:

a proximal optical gum detector transmission portion optically coupled to the distal optical gum detector transmitting portion.

8. The dental hygiene detection apparatus according to claim 7, wherein the proximal optical gum detector transmission portion comprises a first proximal optical transmitting fiber wherein the proximal body portion further comprises an optical combiner; and wherein the optical combiner is optically coupled to the first proximal optical transmitting fiber.

9. The dental hygiene detection apparatus according to claim 8, wherein the proximal optical gum detector transmission portion further comprises a first light emitting diode and a second light emitting diode, each diode optically coupled to the optical combiner to transmit light from the first and second light emitting diodes to the distal optical gum detector transmission portion in the distal oral insertion portion.

10. The dental hygiene detection apparatus according to claim 7, wherein the proximal optical gum detector transmission portion comprises a first proximal transmitting optical fiber and wherein the proximal optical gum detector transmission portion further comprises a light emitting diode optically coupled to the first proximal transmitting optical fiber.

11. The dental hygiene detection apparatus according to claim 7, wherein the proximal body portion further includes a proximal optical gum detector reception portion optically coupled to the distal optical gum detector receiving portion.

12. The dental hygiene detection apparatus according to claim 11, wherein the distal optical gum detector reception portion comprises a first distal receiving optical fiber, and wherein the proximal optical gum detector reception portion comprises a first proximal receiving fiber optically coupled to the first distal receiving optical fiber.

13. The dental hygiene detection apparatus according to claim 12, wherein the proximal optical gum detector reception portion further comprises an optical detector optically coupled to the first proximal receiving optical fiber.

14. The dental hygiene detection apparatus according to claim 13, wherein the proximal optical gum detector reception portion further comprises a second optical detector optically coupled to the first proximal receiving optical fiber.

15. The dental hygiene detection apparatus according to claim 14, wherein the proximal optical gum detector transmission portion comprises a first proximal optical transmitting fiber and a light emitting diode optically coupled to the first proximal transmitting optical fiber.

16. The dental hygiene detection apparatus according to claim 15, wherein the proximal optical gum detector transmission portion further comprises a second proximal optical transmitting fiber and a light emitting diode optically coupled to the second proximal transmitting optical fiber.

17. The dental hygiene detection apparatus according to claim 7, wherein the proximal optical gum detector transmission portion comprises:
   a first proximal transmitting optical fiber optically coupled to the distal optical gum detector transmission portion; and
   a second proximal transmitting optical fiber optically coupled to the distal optical gum detector transmission portion.

18. The dental hygiene detection apparatus according to claim 17, wherein the proximal body portion further comprises:
   a first light emitting diode optically coupled to the first proximal transmitting optical fiber; and
   a second light emitting diode optically coupled to the second proximal transmitting optical fiber.

19. The dental hygiene detection apparatus according to claim 17, wherein the proximal optical gum detector reception portion comprises;
   a first proximal receiving optical fiber optically coupled to the first distal receiving fiber; and
   a second proximal receiving optical fiber optically coupled to the second distal receiving fiber.

20. The dental hygiene detection apparatus according to claim 19, wherein the proximal body portion further comprises;
   a first optical detector optically coupled to the first proximal receiving optical fiber; and
   a second optical detector optically coupled to the second proximal receiving optical fiber.

21. The dental hygiene detection apparatus according to claim 7, wherein the proximal optical gum detector transmission portion comprises:
   a dichroic cube defining a light transmitting surface and optically coupled to the first proximal transmitting fiber via an optical lens disposed to focus light emitted from the light transmitting surface of the dichroic cube through the first proximal transmitting fiber.

22. The dental hygiene detection apparatus according to claim 21, wherein the dichroic cube further comprises a first light receiving surface and a second light receiving surface, the proximal optical gum detector transmission portion further comprises:
   a first light emitting diode and another optical lens disposed between the first light emitting diode and the first light receiving surface to focus light emitted from the first light emitting diode into the first light receiving surface; and
   a second light emitting diode and yet another optical lens disposed between the second light emitting diode and the second light receiving surface to focus light emitted from the second light emitting diode into the second light receiving surface.

23. The dental hygiene detection apparatus according to claim 7, wherein the stream probe signal is a pressure signal, the detection apparatus further comprising:
   a pressure sensor configured and disposed to detect the pressure signal in the proximal probe portion of the stream probe.

24. The dental hygiene detection apparatus according to claim 23, further comprising a controller, the controller processing pressure readings sensed by the pressure sensor and determining whether the pressure readings are indicative of detection of a substance that may be present on the surface based on measurement of a signal, correlating to a substance at least partially obstructing the passage of gas through the open port of the distal tip of the distal probe portion of the stream probe and confirmation via the distal optical gum detector transmission portion and the distal optical gum detector reception portion transmitting and receiving, respectively, an optical signal that upon transmission of the optical signal and reception of the optical signal by the controller, enables the controller to determine if the open port of the distal tip of the distal probe portion is in contact with a substance at least partially obstructing the passage of fluid through the open port of the distal tip of the distal probe portion and not in contact with gums.

25. The dental hygiene detection apparatus according to claim 1, wherein the distal oral insertion portion further comprises a transmitting coupler positioned at the proximal end of the distal oral insertion portion, wherein the distal optical gum detector transmission portion is coupled to the transmitting coupler.

26. The dental hygiene detection apparatus according to claim 25, further comprising a receiving coupler positioned at the proximal end of the distal oral insertion portion, wherein the distal optical gum detector reception portion is coupled to the receiving coupler.

27. The dental hygiene detection apparatus according to claim 26, wherein the proximal body portion is removably attachable to the distal oral insertion portion via the transmitting coupler and the receiving coupler.

28. The dental hygiene detection apparatus according to claim 27, wherein the proximal body portion is integrally formed with the distal oral insertion portion.

* * * * *